US006110889A

United States Patent [19]
Miller et al.

[11] Patent Number: 6,110,889
[45] Date of Patent: Aug. 29, 2000

[54] PEPTIDE TUMOR CELL GROWTH INHIBITORS

[75] Inventors: Edmund J. Miller, Flint, Tex.; Shinichiro Hayashi, Saga, Japan

[73] Assignee: Board of Regents, The University of Texas System, Austin, Tex.

[21] Appl. No.: 08/865,472

[22] Filed: May 29, 1997

Related U.S. Application Data

[63] Continuation-in-part of application No. 08/666,564, Jun. 14, 1996, Pat. No. 5,965,536.

[51] Int. Cl.$^7$ .................................................. A61K 38/00
[52] U.S. Cl. ............................ 514/0.17; 514/2; 530/300; 530/329; 530/351; 424/85.1; 424/85.2; 424/184.1; 424/185.1; 424/277.1
[58] Field of Search ........................ 514/2, 17; 530/300, 530/329, 351; 424/85.1, 85.2, 184.1, 185.1, 277.1

[56] References Cited

U.S. PATENT DOCUMENTS

| | | | |
|---|---|---|---|
| 5,079,228 | 1/1992 | Cohen et al. | ............................. 514/12 |
| 5,504,190 | 4/1996 | Houghter et al. | . |

FOREIGN PATENT DOCUMENTS

| | | |
|---|---|---|
| WO91/05799 | 5/1991 | WIPO . |
| WO92/09300 | 6/1992 | WIPO . |
| 9854210 | 12/1998 | WIPO . |

OTHER PUBLICATIONS

Hayashi et al., *J. Clin. Invest.*, (1997) vol. 99 No. 11, pp 2581–2587.
Miller et al., *Inflamm. Res.*, vol. 45, pp 393–397, (1996).
International Search Report Mailed Aug. 31, 1994.
Cassatellas et al., "Studies on the Regulatory Mechanisms of Interleukin–8 Gene Expression in Resting and IFN–y– Treated Neutrophils: Evidence on the Capability of Staurosporine of Inducing the Production of Interleukin–8 by Human Neutrophils," *Biochem. and Biophys. Research Comm.*, 190(2):660–667, 1993.
Cassatella et al., "Interferon–gamma Inhibits Interleukin–8 Production by Human Polymorphonuclear Leucocytes," *Immun.*, 78:177–184, 1993.
Cerretti et al., "Molecular Characterization of Receptors fro Human Interleukin–8, Gro/Melanoma Growth–Stimulatory Activity and Neutrophil Activating Peptide–2," *Mol. Immun.*, 30:359–367, 1993.
Clark–Lewis et al., "Structure–Activity Relationships of Interleukin–8 Determined Using Chemically Synthesized Analogs," *J Biol. Chem.*, 266(34):23128–23134, 1991.
Corbi et al., "cDNA Cloning and Complete Primary Structure of the α Subunit of a Leukocyte Adhesion Glycoprotein, p150,95," *EMBO J.* , 6(13):4023–4028, 1987.
Gayle III et al., Importance of the Amino Terminus of the Interleukin–8 Receptor in Ligand Interactions, *J. Biol. Chem.*, 268(10):7283–7289, 1993.
Goodman et al., "A Pentapeptide Domain Within the N–Terminus of Interleukin–8 Inhibits Neutrophil Chemotaxis," *FASEB J.*, 5(4):A892, Abstract 3032.
Hayashi et al., "Synthetic Hexa– and Heptapeptides that Inhibit IL–8 from Binding to and Activating Human Blood Neutrophils," *J. Immun.*, 154:814–824, 1995.
Kurdowska et al., "An Anti–Interleukin 8 Monoclonal Antibody that Interferes with the Binding of Interleukin 8 to Cellular Receptors and the Activation of Human Blood Neutrophils," *Hybridoma* 14(3):225–233, 1995.
Kurdowska et al., "Anti–Interleukin–8 Autoantibodies in Alveolar Fluid from Patients with the Acute Respiratory Distress Syndrome (ARDS)," *Am. J. Resp. And Critical Care Medicine*, 153(4,2):Abstract, 1996.
Kurdowska et al., "The Fate of Interleukin–8 (IL–8) in the Lung. Only IL–8–α–2–Macroglobulin Complexes are Taken–up by Human Alveolar Macrophages," Presented at the AAI meeting, 1997.
Kurdowska et al., "Preliminary Studies on the Interaction of Interleukin–8 (IL–8) with α–2–Macroglobulin (α–2–M)," Experimental Biology 95™, Atlanta, Georgia, Apr. 9–13, 1995, Abstract 3110.
Kurdowska et al., "Anti–IL–8 Autoantibodies in Alveolar Fluid from Patients with the Adult Respiratory Distress Syndrome," *J. Immun.*, 157:2699–2706, 1996.
Kurdowska et al., "Studies on the Interactin of IL–8 with Human Plasma α$_2$–Macroglobulin," *J. Immun.*, 158:1930–1940, 1997.
Lam et al., "Differential Effects of Protein Kinase C Inhibitors on Interleukin 8 Induced Exocytosis in Human Neutrophils," In: *Chemotactic Cytokines. Biology of the Inflammatory Peptide Supergene Family*, (Westwick et al., eds.), 175–176, Plenum Press Inc., New York, 1990.
Miller et al., Elevated Interleukin–8 Levels in the Pulmonary Edema Fluid of Patients with ARDS from Sepsis, *Critical Care Medicine*, 24(9):1448–1454, 1996.
Miller et al., "High Yields of Interleukin–8 Produced by a Synthetic Gene Expressed in *Escherichia coli* and Purified with a Single Antibody Affinity Column," *Protein Expression and Purification*, 6:357–362, 1995.

(List continued on next page.)

*Primary Examiner*—Avis M. Davenport
*Attorney, Agent, or Firm*—Arnold White & Durkee

[57] ABSTRACT

Disclosed are peptide-based compositions and methods for inhibiting and modulating the actions of CXC intercrine molecules. The antileukinate peptides described inhibit IL-8, GRO and MIP2β binding to neutrophils and neutrophil activation. The peptides are particularly advantageous as they inhibit IL-8-induced enzyme release at a 25 fold lower concentration than is required to inhibit chemotaxis, which makes them ideal for treating various inflammatory diseases and disorders including, amongst others, Adult Respiratory Distress Syndrome (ARDS), cystic fibrosis and chronic bronchitis. The invention further includes methods for inhibiting tumor cell growth by employing selected members of the disclosed group of peptides to inhibit α-chemokine binding to the tumor cell.

14 Claims, 23 Drawing Sheets

OTHER PUBLICATIONS

Miller et al., "Interleukin–8 (IL–8)–Induced Neutrophil Chemotaxis is Inhibited by Synthetic Peptides," *Endocytosis/Phacogytosis, FASEB J.,* 4(5):A2117, Abstract 2452, 1990.

Miller et al., "Peptide Inhibitor of Interleukin–8 (IL–8) Reduces Staphylococcal Enterotoxin–A (SEA) Induced Neutrophil Trafficking to the Lung," *Am. J. Resp. Critical Care Med,* 153(4):A285, Abstract. Apr. 1996.

Miller et al., "Peptide Inhibitor of Interleukin–8 (IL–8) Reduces Staphylococcal Enterotoxin–A (SEA) Induced Neutrophhil Trafficking to the Lung," *Inflamm. Res.,* 45:393–397, 1996.

Miller et al., "Interleukin–8 (IL–8) is a Major Neutrophil Chemotaxin from Human Alveolar Macrophages Stimulated with Staphylococcal Enterotoxin A (SEA)," *Inflamm. Res.,* 45:386–392, 1996.

Miller et al., "Elevated Levels of NAP–1/Interleukin–8 are Present in the Airspaces of Patients with the Adult Respiratory Distress Syndrome and are Associated with Increased Mortality," *Am. Rev. Respir. Dis.,* 146:427–432, 1992.

Miller and Idell, "Interleukin–8: An Important Neutrophil Chemotaxin in Some Cases of Exudative Pleural Effusions," *Experimental Lung Research,* 19:589–601, 1993.

Miller et al., "A Synthetic Peptide Which Specifically Inhibits Heat–Treated Interleukin–8 Binding and Chemotaxis for Neutrophils," *Agents Actions,* 40:200–208, 1993.

Miller and Brelsford, "Interleukin 8: The Major Neutrophil Chemotaxin in a Case of Pseudogout," *J. Rheumatology,* 20(7):1250–1252, 1993.

Moser et al., "Interleukin–8 Antagonists Generated by N–Terminal Modification," *J. Biol. Chem.,* 268(10):7125–7128, 1993.

Mulligan et al., "Inhibition of Lung Inflammatory Reactions in Rats by an Anti–Human IL–8 Antibody," *J. Immun.,* 150(12):5585–5595, 1993.

Murphy and Tiffany, "Cloning of Complementary DNA Encoding a Functional Human Interleukin–8 Receptor," *Science,* 253:1280–1283, 1991.

Nakamura et al., "Neutrophil Elastase in Respiratory Epithelial Lining Fluid of Individuals with Cystic Fibrosis Induces Interleukin–8 Gene Expression in a Human Bronchial Epithelial Cell Line," *J. Clin. Invest.,* 89:1478–1484, 1992.

Peterson et al., "Salmeterol Prevents Influx of Neutrophils at Proximal Sites in Rabbit Airways," *Am. J. Resp. And Critical Care Med.,* 153(4):A444, Abstract, 1996.

Peterson et al., "Salmeterol Prevents Influx of Neutrophils into the Lungs, but not by β–Adrenergic Stimulation," *FASEB J.,* 10(3):A639, Abstract 3691, 1996.

Richman–Eisenstat et al., "Interleukin–8: An Important Chemoattractant in Sputum of Patients with Chronic Inflammatory Airway Diseases," *Am. J. Physiol. (Lung Cell Mol. Physiol.),* 264:L413–L418, 1993.

Standiford et al., "Disparate Regulation of Interleukin 8 Gene Expression from Blood Monocytes, Endothelial Cells, and Fibroblasts by Interleukin 4," 171(2):531–536, 1990.

Standiford et al., "Regulation of Human Alveolar Macrophage– and Blood Monocyte–Derived Interleukin–8 by Prostaglandin $E_2$ and Dexamethasone," *Am. J. Respir. Cell Mol. Biol.,* 6:75–81, 1992.

Wu et al., "G Protein–Coupled Signal Transduction Pathways for Interleukin–8," *Science,* 261:101–103, 1993.

Clore and Gronenborn, "NMR and X–Ray Analysis of the Three–Dimensional Structure of Interleukin–8," *In: Cytokines: Interleukin 8 (NAP–1) and Related Chemotactic Cytokines,* (Baggiolini, M. and Sorg, C., eds) Karger, Basel, pp. 18–40, 1992.

Corbi et al., "Genomic Structure of an Integrin α Subunit, the Leukocyte p150,95 Molecule," *J. Biol. Chem.,* 265:2782–2788, Feb. 1990.

DeForge et al., "Oxygen Radical Scavengers Selectively Inhibit Interleukin 8 Production in Human Whole Blood," *J. Clin. Invest.,* 90:2123–2129, Nov. 1992.

Hayashi et al., "Characterization of the binding of epithelial neutrophil activating peptide–78 (ENA78) to interleukin–8 receptors," *FASEB J.,* 9:A247, Apr. 9–13, 1995.

Horuk et al., "Purification, Receptor Binding Analysis, and Biological Characterization of Human Melanoma Growth Stimulating Activity (MGSA)," *J. Biol. Chem.,* 268:541–546, Jan. 1993.

Houghten et al., "Generation and use of synthetic peptide combinatorial libraries for basic research and drug discovery," *Nature,* 354:84–86, Nov. 1991.

Lee et al., "Characterization of Two High Affinity Human Interleukin–8 Receptors," *J. Biol. Chem.,* 267:16283–16287, Aug. 1992.

McElvaney et al., "Modulation of Airway Inflammation in Cystic Fibrosis: In Vivo Suppression of Interleukin–8 Levels on teh Respiratory Epithelial Surface by Aerosolization of Recombinant Secretory Leukoprotease Inhibitor," *J. Clin. Invest.,* 90:1296–1301, Oct. 1992.

McGuire et al., "Studies on the Pathogenesis of the Adult Respiratory Distress Syndrome," *J. Clin, Invest.,* 69:543–553, Mar. 1982.

Mueller et al., "Melanoma Growth Stimulatory Activity Enhances the Phosphorylation of the Class II Interleukin–8 Receptor in Non–hematopoietic Cells," *J. Biol. Chem.,* 269:1973–1980, Jan. 1994.

Norgauer et al., "Expression and Growth–Promoting Function of the IL–8 Receptor β in Human Melanoma Cells," *J. Immunol.,* 156:1132–1137, 1996.

Ovchinnikov et al., "Cyclic GMP phosphodiesterase from bovine retina: Amino acid sequence of the α–subunit and nucleotide sequence of the corresponding cDNA," *FEBS Lett.,* 223:169–173, Oct. 1987.

Schumacher et al., "High– and low–affinity binding of GROα and neutrophil–activating peptide 2 to interleukin 8 receptors on human neutrophils," *Proc. Natl. Acad. Sci.,* 89:10542–10546, Nov. 1992.

Togo et al., "D–Phe[7]–Substituted Peptide Bradykinin Antagonists are not Substrates for Kininase II," *Peptides,* 10:109–112, 1989.

```
SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
         (A) LENGTH: 6 amino acids
         (B) TYPE: amino acid
         (C) STRANDEDNESS:
         (D) TOPOLOGY: linear (xi) SEQUENCE DESCRIPTION: SEQ ID NO:1:

Arg Arg Trp Trp Cys Arg
1               5

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS:
         (D) TOPOLOGY: linear (xi) SEQUENCE DESCRIPTION: SEQ ID NO:2:

Arg Arg Trp Trp Cys Arg Xaa
1               5

(2) INFORMATION FOR SEQ ID NO:3:

(i) SEQUENCE CHARACTERISTICS:
         (A) LENGTH: 7 amino acids
         (B) TYPE: amino acid
         (C) STRANDEDNESS:
         (D) TOPOLOGY: linear (xi) SEQUENCE DESCRIPTION: SEQ ID NO:3:

Arg Arg Trp Trp Cys Arg Ala
1               5

(2) INFORMATION FOR SEQ ID NO:4:

(i) SEQUENCE CHARACTERISTICS:
         (A) LENGTH: 7 amino acids
         (B) TYPE: amino acid
         (C) STRANDEDNESS:
         (D) TOPOLOGY: linear (xi) SEQUENCE DESCRIPTION: SEQ ID NO:4:

Arg Arg Trp Trp Cys Arg Cys
1               5

(2) INFORMATION FOR SEQ ID NO:5:

(i) SEQUENCE CHARACTERISTICS:
         (A) LENGTH: 7 amino acids
         (B) TYPE: amino acid
```

```
        (C) STRANDEDNESS:
        (D) TOPOLOGY: linear (xi) SEQUENCE DESCRIPTION: SEQ ID NO:5:

Arg Arg Trp Trp Cys Arg Asp
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:6:

Arg Arg Trp Trp Cys Arg Glu
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:7:

Arg Arg Trp Trp Cys Arg Phe
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:8:

Arg Arg Trp Trp Cys Arg Gly
1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:9:

Arg Arg Trp Trp Cys Arg His
1               5

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:10:

Arg Arg Trp Trp Cys Arg Ile
1               5
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:11:

Arg Arg Trp Trp Cys Arg Lys
1               5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:12:

Arg Arg Trp Trp Cys Arg Leu
1               5

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:13:

Arg Arg Trp Trp Cys Arg Met
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:14:

Arg Arg Trp Trp Cys Arg Asn
1               5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:15:

Arg Arg Trp Trp Cys Arg Pro
1               5

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:16:

```
Arg Arg Trp Trp Cys Arg Gln
1               5
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:17:

```
Arg Arg Trp Trp Cys Arg Arg
1               5
```

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:18:

```
Arg Arg Trp Trp Cys Arg Ser
1               5
```

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:19:

```
Arg Arg Trp Trp Cys Arg Thr
1               5
```

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:20:

```
Arg Arg Trp Trp Cys Arg Val
1               5
```

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:21:

```
Arg Arg Trp Trp Cys Arg Trp
1               5
```

(2) INFORMATION FOR SEQ ID NO:22:

(i) SEQUENCE CHARACTERISTICS:
        (A) LENGTH: 7 amino acids

```
            (B) TYPE: amino acid
            (C) STRANDEDNESS:
            (D) TOPOLOGY: linear (xi) SEQUENCE DESCRIPTION: SEQ ID NO:22:

Arg Arg Trp Trp Cys Arg Tyr
1               5

(2) INFORMATION FOR SEQ ID NO:23:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:23:

Arg Arg Trp Trp Cys Xaa
1               5

(2) INFORMATION FOR SEQ ID NO:24:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:24:

Arg Arg Trp Trp Cys Ala
1               5

(2) INFORMATION FOR SEQ ID NO:25:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:25:

Arg Arg Trp Trp Cys Cys
1               5

(2) INFORMATION FOR SEQ ID NO:26:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:26:

Arg Arg Trp Trp Cys Asp
1               5

(2) INFORMATION FOR SEQ ID NO:27:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:27:

Arg Arg Trp Trp Cys Glu
1               5
```

(2) INFORMATION FOR SEQ ID NO:28:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:28:

Arg Arg Trp Trp Cys Phe
1               5

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:29:

Arg Arg Trp Trp Cys Gly
1               5

(2) INFORMATION FOR SEQ ID NO:30:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:30:

Arg Arg Trp Trp Cys His
1               5

(2) INFORMATION FOR SEQ ID NO:31:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:31:

Arg Arg Trp Trp Cys Ile
1               5

(2) INFORMATION FOR SEQ ID NO:32:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:32:

Arg Arg Trp Trp Cys Lys
1               5

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:33:

Arg Arg Trp Trp Cys Leu
1               5

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:34:

Arg Arg Trp Trp Cys Met
1               5

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:35:

Arg Arg Trp Trp Cys Asn
1               5

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:36:

Arg Arg Trp Trp Cys Pro
1               5

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:37:

Arg Arg Trp Trp Cys Gln
1               5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:38:

Arg Arg Trp Trp Cys Ser
1               5

(2) INFORMATION FOR SEQ ID NO:39:

(i) SEQUENCE CHARACTERISTICS:

```
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:39:

Arg Arg Trp Trp Cys Thr
1               5

(2) INFORMATION FOR SEQ ID NO:40:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:40:

Arg Arg Trp Trp Cys Val
1               5

(2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:41:

Arg Arg Trp Trp Cys Trp
1               5

(2) INFORMATION FOR SEQ ID NO:42:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:42:

Arg Arg Trp Trp Cys Tyr
1               5

(2) INFORMATION FOR SEQ ID NO:43:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:43:

Arg Xaa Xaa Xaa Xaa Xaa
1               5

(2) INFORMATION FOR SEQ ID NO:44:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:44:

Xaa Xaa Xaa Xaa Xaa Arg
1               5
```

(2) INFORMATION FOR SEQ ID NO:45:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:45:

Xaa Arg Xaa Xaa Xaa Xaa
1               5

(2) INFORMATION FOR SEQ ID NO:46:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:46:

Xaa Xaa Trp Xaa Xaa Xaa
1               5

(2) INFORMATION FOR SEQ ID NO:47:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:47:

Xaa Xaa Xaa Trp Xaa Xaa
1               5

(2) INFORMATION FOR SEQ ID NO:48:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:48:

Xaa Xaa Xaa Xaa Cys Xaa
1               5

(2) INFORMATION FOR SEQ ID NO:49:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:49:

Glu Leu Arg Cys Gln Cys Ile Lys Thr Tyr
1               5                   10

(2) INFORMATION FOR SEQ ID NO:50:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:50:

Glu Leu Arg Ser Gln Ser Ile Lys Thr Tyr
1               5                   10

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS:
        (D) TOPOLOGY: linear (xi) SEQUENCE DESCRIPTION: SEQ ID NO:51:

Glu Leu Arg Met Gln Met Ile Lys Thr Tyr
1               5                   10

(2) INFORMATION FOR SEQ ID NO:52:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:52:

Gln Ile Pro Arg Arg Ser Trp Cys Arg Phe Leu Phe
1               5                   10

(2) INFORMATION FOR SEQ ID NO:53:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:53:

Gly Trp Arg Arg Trp Trp Cys Asp Ala Val Leu Tyr
1               5                   10

(2) INFORMATION FOR SEQ ID NO:54:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:54:

Lys Glu Leu Arg Cys Gln
1               5

(2) INFORMATION FOR SEQ ID NO:55:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:55:

Ser Tyr Ser Met Glu His Phe Arg Trp Gly Lys Pro Val
1               5                   10

(2) INFORMATION FOR SEQ ID NO:56:

```
        (i) SEQUENCE CHARACTERISTICS:
            (A) LENGTH: 5 amino acids
            (B) TYPE: amino acid
            (C) STRANDEDNESS:
            (D) TOPOLOGY: linear (xi) SEQUENCE DESCRIPTION: SEQ ID NO:56:

Arg Arg Trp Trp Cys
1               5

(2) INFORMATION FOR SEQ ID NO:57:

(i) SEQUENCE CHARACTERISTICS:
            (A) LENGTH: 7 amino acids
            (B) TYPE: amino acid
            (C) STRANDEDNESS:
            (D) TOPOLOGY: linear (xi) SEQUENCE DESCRIPTION: SEQ ID NO:57:

Arg Arg Trp Trp Cys Xaa Xaa
1               5

(2) INFORMATION FOR SEQ ID NO:58:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:58:

Arg Arg Xaa Trp Cys Xaa
1               5
```

PEPTIDE TUMOR CELL GROWTH INHIBITORS

This application is a continuation-in-part of U.S. application Ser. No. 08/666,564 filed Jun. 14, 1996 U.S. Pat. No. 5,965,536.

The U.S. government owns rights in the present invention pursuant to grant number ROI-HL 403650 from NHLBI.

BACKGROUND OF THE INVENTION

1. Field of the Invention

The present invention relates generally to the field of cytokine actions and more particularly concerns methods and compositions for inhibiting and modulating the actions of CXC intercrine molecules. Disclosed are peptide compositions which inhibit interleukin 8 (IL-8) and, particularly, which preferentially inhibit IL-8-induced release of degradative enzymes by neutrophils. These compositions may be employed to treat various inflammatory diseases and disorders including the Adult Respiratory Distress Syndrome (ARDS) and cystic fibrosis.

2. Description of the Related Art

IL-8 is a member of the CXC intercrine family of cytokines, so named due to elements of their N-terminal sequences. This family also includes, amongst others, peptide molecules known as growth related oncogene (GRO, or GRO/MGSA) and macrophage inflammatory protein 2β (MIP2β). IL-8 is a peptide of approximately 8 kD, and is about 72 amino acids in length, with this length varying according to the post-translational processing in different cell types (Yoshimura et al., 1989; Hebert et al., 1990; Strieter et al., 1989). The IL-8 gene was first identified by analyzing the genes transcribed by human blood mononuclear cells stimulated with Staphylococcal enterotoxin A (Schmid and Weissman, 1987). IL-8 production is known to be induced by tumor necrosis factor and interleukin 1 (Strieter et al., 1990).

MGSA/GROα is a peptide which was first identified as an autostimulatory growth factor of Hs 294T melanoma cells (Richmond et al., 1983; 1985; Richmond and Thomas, 1986). Further studies indicated that it was produced by diverse melanoma cell lines (Lawson et al., 1987) and played an important role in the tumorigenesis and growth of malignant melanoma cells (Mintz and Silvers, 1993). Sequence analysis demonstrated that MSGA/GROα is a member of the superfamily called "α-chemokines" (Oppenheim et al., 1991). This family of proteins were chemotactic for neutrophils and had substantial sequence homology, a C-X-C motif near the amino-terminal end, and two additional Cys residues closer to the carboxyl-terminal end. The functions of a chemokines were mediated by receptors on the cell surface membrane (Murphy and Tiffany, 1991; Holmes et al., 1991; Mueller et al., 1994). Recent studies showed the presence of some types of chemokine receptors on melanoma cells. Some melanoma cells possess interleukin-8 (IL-8) receptors similar to those on neutrophils (Holmes et al., 1991; Mueller et al., 1994; Moser et al., 1993; Norgauer et al., 1996).

MGSA/GROα is a 73 amino acid peptide which shares sequence characteristics of a superfamily of peptides called α-chemokines. Richmond and colleagues initially discovered that melanoma cells secreted autostimulatory (autocrine) growth factors (Richmond et al., 1983; 1985; Richmond and Thomas, 1986; Richmond et al., 1982). It was found that most of the activity was caused by a single acid stable protein of about 15 kDa and designated it melanoma growth stimulatory activity (MGSA) (Richmond et al., 1983; 1985). MGSA was found to be a mitogen for the melanoma cell line Hs 294T which produces this factor. MGSA was secreted by diverse melanoma cell lines but not by benign nevus cell lines (Lawson et al., 1987), while immunoreactive MGSA was shown in both types of cells (Richmond et al., 1986). cDNA for MGSA isolated from Hs 294T cells was later found to be identical to oncogene growth-related peptide (GROα) gene (Richmond et al., 1988). The formal name for this protein was then designated as MGSA/GROα.

Recently, a second chemokine was found to be important for melanoma cell growth and metastasis in some melanoma cell lines. Schadendorf and colleagues determined that some melanoma cell lines tested secreted IL-8 (Schadendorf et al., 1993). Both of two IL-8 secreting cell lines studied in more detail were dependent on IL-8 for growth. Antisense oligonucleotides targeted against human IL-8 mRNA inhibited cell proliferation, colony formation in soft agar, and secretion of IL-8 into culture supernatants. In an analysis of 13 different human melanoma cell lines, it was shown that expression of IL-8 correlates with the metastatic potential of melanoma cells in BALB/c nude mice (Singh et al., 1994).

Other studies further indicate a role of these chemokines in melanoma growth and tumorigenesis. Mintz and Silvers developed a method of producing melanomas by grafting skin from Tyr-SV40E transgenic mice which are highly susceptible to melanoma to Tyr-SV40E hosts of a low susceptibility of the same inbred strain (Mintz and Silvers, 1993). It was suggested that growth factors and cytokines known to be produced in wound repair may trigger the growth and malignant conversion of melanocytes. Nanney and colleague showed that MGSA/GROα and its receptors are present in human burn wounds and may act as a mediator for wound repair (Nanney et al., 1995). MGSA/GROα and I11-8 was induced by ultraviolet B radiation in human keratinocyte cell lines (Venner et al., 1995) IL-8 interacts with at least two distinct receptors on neutrophils (Holmes et al., 1991; Murphy and Tiffany, 1991). The receptors are coupled to GTP-binding proteins, allowing transmission of the IL-8 signal into the cell (Wu et al., 1993). While most of the members of the intercrine family, such as GRO and MIP2β, bind to one of the receptors, IL-8 binds to both of the IL-8 receptors (LaRosa et al., 1992; Cerretti et al., 1993). The three dimensional structure of IL-8 has been elucidated by NMR (Clore et al., 1990) and by X-ray crystallography (Clore and Gronenbom, 1992; Baldwin et al., 1991). A freely movable amino terminal end is followed by three beta pleated sheets and an alpha helix is located at the carboxyl-terminal end (Oppenheim et al., 1991). Several lines of evidence suggest that both the amino- and carboxyl-terminal ends are involved in binding to its receptors (Clore et al., 1990; Clark-Lewis et al., 1991; Moser et al., 1993).

Certain functions of the CXC intercrines have been elucidated by several laboratories (Yoshimura et al., 1989; Schroder et al., 1988; Peveri et al., 1988). For example, the major functions of the IL-8 peptide appear to be related to its ability to stimulate neutrophil chemotaxis and activation (Larsen et al., 1989; Schroder et al., 1988; Peveri et al., 1988; Yoshimura et al., 1987) and to promote angiogenesis (Koch et al., 1992). If neutrophils are 'primed', e.g., by agents such as surface adherence or E. coli endotoxin (also known as lipopolysaccharide or LPS), IL-8 also stimulates the release of neutrophil enzymes such as elastase and myeloperoxidase.

Although the neutrophil inflammatory response is essential for the destruction of bacteria which are invading the body, inappropriate neutrophil activation causes several problems. For example, if the neutrophils are properly primed when attracted to the lungs, they release destructive enzymes into the lung tissue. This can lead to the development of adult respiratory distress syndrome (ARDS) (Weiland et al., 1986; Idell et al., 1985). ARDS attacks between 150,000 and 200,000 Americans per year, with a mortality rate of 50–80% in the best clinical facilities (Balk and Bone, 1983). ARDS is initiated by bacterial infections, sudden severe dropping of the blood pressure (shock), and many other insults to the body. Recent studies have demonstrated that IL-8 is the major neutrophil activator in the lungs of patients with ARDS (Miller et al., 1992), and primate models of endotoxin shock also implicate IL-8 as a causative agent (Van Zee et al., 1991).

High concentrations of IL-8 have also been found in inflammatory exudates in other disorders and pathological conditions in which IL-8 is thought to play an important pathogenic role (Brennan et al., 1990; Miller and Idell, 1993; Miller et al., 1992). For example, IL-8 has also been implicated as a possible mediator of inflammation in rheumatoid arthritis (Brennan et al., 1990; Seitz et al., 1991) and pseudogout (Miller and Brelsford, 1993); and to have a role in cystic fibrosis (McElvaney et al., 1992; Nakamura et al., 1992; Bedard et al., 1993). Therefore, modulation of IL-8 function appears to be good strategy to control a variety of pathological conditions.

Some progress has recently been made in identifying compounds capable of reducing IL-8 synthesis. Such compounds include IL-4, oxygen radical scavengers, secretory leukoprotease inhibitor and interferon gamma (Standiford et al., 1990; DeForge et al., 1992; McElvaney et al., 1992; Cassatella et al., 1993a; 1993b), however, such studies do not concern IL-8 inhibitors. Other diverse compositions, including protein kinase C inhibitors, IL-4, and anti-IL-8 antibodies, have also been reported to modulate IL-8 actions (Lam et al., 1990; Standiford et al., 1992; Mulligan et al., 1993). Unfortunately, these compounds are far from ideal as candidates for use as IL-8 inhibitors in a clinical setting.

Certain progress has also been made in identifying peptide IL-8 inhibitors, however, most of such work has focused on portions of the IL-8 molecule itself (Miller et al., 1990; Gayle et al., 1993). For example, the present inventors have shown that synthetic peptides, and particularly, IL-8 amino terminal peptides, inhibit IL-8 binding to neutrophils and neutrophil chemotaxis (Miller et al., 1990; Miller et al., 1993). An N-terminal pentapeptide IL-8 inhibitor has also been reported (Goodman et al., 1991). Unfortunately, to date, the inhibitory function of IL-8 derived peptides has proven incomplete and insufficient.

As particularly effective peptide inhibitors of CXC intercrines such as IL-8 have yet to be identified, it seems to be clear that compositions other than the IL-8 molecule itself now need to be investigated. The identification of peptide inhibitors capable of preferentially inhibiting neutrophil enzyme release in comparison to chemotaxis would be a particularly advantageous discovery as this would enable neutrophils to enter the lungs and defend against bacterial invasion and yet not cause tissue damage.

SUMMARY OF THE INVENTION

The present invention seeks to overcome the drawbacks inherent in the prior art by providing new methods and compositions for modulating and inhibiting the actions of CXC intercrine molecules such as IL-8, GRO (GRO/MGSA) and MIP2β. The peptides and pharmacological compositions disclosed reduce IL-8, GRO and MIP2β binding to neutrophils and inhibit IL-8-induced neutrophil activation. These peptide formulations are particularly advantageous as they are capable of inhibiting IL-8-induced enzyme release at significantly lower concentrations than is required to inhibit neutrophil chemotaxis. Also provided are methods for treating various diseases and disorders, particularly inflammatory diseases, in which the unrestrained actions of CXC intercrines play a role. Additionally, certain peptides have been found to affect melanoma cell growth. In particular, a novel hexapeptide, Antileukinate (Ac-RRWWCR-NH$_2$), has been found to be a potent inhibitor of binding of α-chemokines to the receptors. The effect of Antileukinate on MGSA/GROα binding to melanoma cells in several cell lines, including Hs 294T, RMPI-7951, A375P, A375SM, C8161 and WM115. suppresses the growth of the melanoma cells. Additionally, the hexapeptide also inhibits growth in lung adenocarcinoma cell lines A549, NCI-H441 and KS-LU-1 as well as in squamous cell lung cancer NCI-H292 and adenocarcinomas from stomach AGS and Hs746T, breast tissue MCF-7, prostate DU145 and colon Caco-2.

A hexapeptide, termed Antileukinate, has been identified as a potent inhibitor of binding of α-chemokines to their receptors on neutrophils. When Antileukinate was added to melanoma cells, it inhibited the binding of MGSA/GROα. The growth of cells from several melanoma cell lines was suppressed completely in the presence of 100 μM peptide. The cell growth inhibition was reversed by the removal of the peptide from the culture media or by the addition of an excess amount of MGSA/GROα. The viability of Hs 294T cells in the presence of 100 μM peptide was greater than 92%. These findings support the view that MGSA/GROα is an essential autostimulatory growth factor for melanoma cells. Antileukinate thus appears to inhibit tumor cell growth by preventing binding of the natural ligand to its receptors.

The invention is generally based upon the inventors surprising discovery that relatively small peptides including the amino acid sequence Arg Arg Trp Trp Cys Xaa$_1$ (RRWWCX; SEQ ID NO:23), wherein Xaa$_1$ is any amino acid residue, are potent inhibitors of CXC intercrine molecules such as IL-8. As used herein, the terms "CXC intercrine family molecules" and "CXC intercrines" are used collectively to refer to the group of peptide intercrines which include the CXC sequence motif in their N-terminal regions. CXC intercrines are known to include IL-8, GRO, MIP2α, MIP2β and ENA78, all of which molecules, and any other intercrine polypeptides that include the CXC motif, will be understood to fall within this term as used in the present application.

The inhibitory peptides of the present invention may be termed "antileukinates". Certain hexamer peptides of the sequence RRWWCX (SEQ ID NO:23) have been previously shown to have anti-bacterial activity against *Staphylococcal aureus* (Houghten et al., 1991). However, there was no previously documented information to suggest that any such peptides would have the advantageous anti-cytokine/intercrine, anti-neutrophil and anti-inflammatory activities disclosed herein. The anti-tumor activity is particularly unexpected, particularly since the peptides are effective against a wide range of tumor cell types. It is believed that this broad activity arises because the so-called antileukin peptides herein disclosed inhibit binding of several different cytokines that affect cell growth.

In certain aspects, the present invention therefore concerns methods for inhibiting CXC intercrines, such as GRO and MIP2α or MIP2β, and most particularly, methods for inhibiting IL-8. As used herein, the term "inhibiting CXC intercrines" refers to the processes by which the biological actions of the CXC intercrines are reduced. This may be particularly assessed by inhibiting their binding to one of the IL-8 receptors on their target cells, such as neutrophils, although any mode of determining CXC intercrine inhibition may be employed.

The term IL-8 is used to refer to the cytokine compositions previously known as neutrophil-activating factor, monocyte-derived neutrophil-activating peptide, monocyte-derived neutrophil-chemotactic factor and neutrophil-activating peptide-1. As used herein, the term "inhibiting IL-8" generally refers to the processes by which the biological actions of IL-8 are reduced or lessened. This includes the inhibition of any or all of the known actions of IL-8. These actions include modulating sub-cellular effects, such as receptor binding or altering cytosolic calcium levels; modulating cellular effects such as granulocyte recruitment and activation; and also affecting physiological effects, such as inflammation and angiogenesis.

In preferred embodiments, the inhibition of IL-8 function referred to in this application is the inhibition of IL-8 action on granulocytes such as neutrophils (polymorphonuclear neutrophils, PMN). This may be determined in many cellular and physiological ways, as disclosed herein. For example, by measuring inhibition of IL-8 binding to purified receptor compositions or neutrophils; by determining the inhibition of IL-8-induced neutrophil chemotaxis or diapedesis; by measuring the inhibition of IL-8-stimulated neutrophil enzyme release (e.g., myeloperoxidase, β-glucuronidase or elastase release) or superoxide production; or by assaying for anti-inflammatory effects in vivo, e.g., using a rabbit model of dermal inflammation.

The preferred manner of determining IL-8 inhibition, or indeed GRO or MIP2β inhibition, is to assay for a reduction in the intercrine binding to neutrophils, which is the most simple and straightforward method. In addition, binding of the particular intercrine to its receptor(s) must precede any other action that it has on neutrophils or other cell types. "Inhibition" of intercrines, as exemplified by the inhibition of IL-8, GRO or MIP2α or MIP2β binding to neutrophils, refers to the capacity of a given peptide or composition to inhibit intercrine binding to any detectable degree, i.e., to reduce binding below the levels observed in the absence of the peptide or composition.

The inhibition of CXC intercrine binding to neutrophils may be expressed as a % Binding Inhibition value, with the higher figures representing the more effective inhibitors. The preferred peptides will generally have the higher % binding inhibition figures. Naturally, the % binding inhibition calculated will depend upon the precise assay conditions, such as the concentration of CXC intercrine and the concentration of the given peptide or composition. Conditions such as those used to generate the data of Table 1A, Table 1B, Table 5A and Table 5B, may be employed to determine whether a given peptide has any inhibitory activity. However, one may choose to employ more discriminatory conditions, such as those using lower peptide concentrations, e.g., on the order of about 20 μM (as used to generate the data of FIG. 1 and FIG. 9), where one desires to obtain particularly accurate quantitative or comparative data. In any event, the determination of whether a peptide or analogue is capable of inhibiting a CXC intercrine, such as IL-8, is a straightforward matter readily achieved using assays such as those disclosed herein.

Although an understanding of the mechanism of action of the CXC intercrine inhibitors is not relevant in terms of their practical utility, it is, however, important to note that the peptide inhibitors of this invention are capable of preferentially inhibiting IL-8-induced neutrophil enzyme release at lower concentrations than IL-8-induced chemotaxis. In this sense, the term "inhibiting", when used in connection with this invention, also means "modulating" in that certain neutrophil functions are more significantly inhibited than others.

The ability of the peptides to inhibit IL-8-induced neutrophil degradative enzyme release at about a 25 times lower concentration than is required to inhibit IL-8-induced neutrophil chemotaxis is an important discovery that could not have been predicted from prior studies. This means that neutrophils may still be recruited to a site of injury, but that the detrimental effects of the enzymes that they would normally release will be significantly reduced. This property, coupled with their small size, renders these type of peptides ideal for use in various treatment protocols and especially in the treatment of lung injury.

To achieve CXC intercrine inhibition, such as IL-8, GRO or MIP2 inhibition, or to preferentially reduce neutrophil enzyme release in comparison to neutrophil chemotaxis, in accordance with this invention one would generally contact the CXC intercrine family molecule or intercrine target cells, such as granulocytes or neutrophils, with a biologically effective amount of a composition comprising a peptide of the family disclosed herein. The "contact" process is the process by which the active peptide or peptides from within the composition contact either the CXC intercrine peptide or one of their receptors present on a target cell, or both, and reduce or inhibit their functional interaction. Although of scientific interest, the mechanisms by which the CXC intercrine signals transmitted to a given cell are reduced are not relevant to the practice of the invention.

To contact a CXC intercrine or intercrine target cell with a peptide-containing composition one may simply add the peptide or composition to target cells, such as neutrophils, and intercrines in vitro. Alternatively, one may administer a biologically effective amount of a pharmacologically acceptable form of the peptide or composition to an animal, where it will contact, e.g., neutrophils or macrophages and intercrines in a biological fluid in vivo. In this context, "contact" is achieved simply by administering the composition to the animal. Virtually any pharmaceutical peptide formulation may be used, including, but not limited to, formulations for parenteral administration, such as for intravenous, intramuscular and subcutaneous administration; inhalants, aerosols and spray formulations; formulations of peptides for topical use, such as in creams, ointments and gels; and other formulations such as peptides with lipid tails, peptides encapsulated in micelles or liposomes and drug release capsules including the active peptides incorporated within a biocompatible coating designed for slow-release.

Increased levels of IL-8 are known to be present in lung edema fluids in patients with ARDS (Miller et al., 1992) and in the sputum of patients with cystic fibrosis (Richman-Eisenstat et al., 1993); in pleural spaces of patients with pleural effusions (Miller and Idell, 1993); in joint fluids from patients with several kinds of joint disease (Brennan et al., 1990; Miller and Brelsford, 1993), in psoriatic plaques and in synovial fluid from arthritic patients (Lam et al., 1990). Inappropriate neutrophil activation is connected with all such disorders and with ischemic and reperfusion injuries (DeForge et al., 1992). As the inhibition of IL-8 neutrophil recruitment has been shown to reduce lung inflammation in vivo (Mulligan et al., 1993), and as the type of in vitro studies employed herein are accepted as being predictive of in vivo activity (see U.S. Pat. No. 5,079,228, incorporated herein by reference), the highly successful inhibition of IL-8-induced neutrophil activation disclosed in the application supports the broad clinical utility of these peptides.

The present invention therefore also provides methods for treating a wide variety of diseases and disorders in which CXC intercrines, particularly IL-8, play a role, especially those which have an inflammatory component. This includes treating subjects with lung injuries and disorders, including bronchial inflammation, such as chronic bronchitis, cystic fibrosis, pleural effusions, asthma, and ARDS; skin disorders such as psoriasis and dermatitis; diseases of the joints, including rheumatoid arthritis; and generally reducing inflammation in other clinical settings, such as in the treatment of pseudogout, inflammatory bowel disease or reperfusion cardiac damage after myocardial infarction. These peptides could even be used as anti-proliferative agents to downregulate lymphocyte proliferation, for example, in the treatment of cancer and other diseases and disorders associated with increased cellular proliferation.

To treat any one of the above conditions, or any other disorder influenced by neutrophil activity and characterized by inflammation, one would identify a patient having the particular inflammatory or IL-8-linked disease and then administer to the patient, preferably parenterally, a biologically effective amount of a pharmaceutical composition which includes one or more peptides of the family disclosed herein.

Naturally, one would generally tailor the particular pharmaceutical formulation according to the disease or disorder being treated. For example, in methods to treat skin disorders, a topical cream or gel formulation would be used, whereas in methods to treat pulmonary disorders, injectable formulations, or even a spray, aerosol or inhalant, may be employed. In methods to reduce inflammation in other areas of the body, one may use peptides formulated for parenteral administration or peptides incorporated in a biocompatible coating designed for slow-release. Liposome-encapsulation may be employed, which is known to increase the efficacy and significantly prolong the half-life of administered compounds, particularly those of lower molecular weight such as the peptides disclosed herein. Various compositions and techniques for preparing all such pharmaceutical formulations will generally be known to those of skill in the art in light of the present disclosure. For a detailed listing of suitable pharmacological compositions and associated administrative techniques one may wish to refer to *Remington's Pharmaceutical Sciences*, 16th ed., 1980, Mack Publishing Co., incorporated herein by reference.

IL-8 or CXC intercrine inhibition is achieved by using a biologically effective amount of the inhibitory peptide or peptides. As used herein, a "biologically effective amount" of a peptide or composition refers to an amount effective to inhibit the actions of IL-8 or the particular intercrine. For example, in regard to IL-8 inhibition, an appropriate amount would be that effective to reduce neutrophil enzyme release, particularly in comparison to chemotaxis. As disclosed herein, a variety of different peptide concentrations are very effective in vitro, such as those between about 100 μM and about 20 μM. Clinical doses which result in similar a local concentration of peptides are therefore contemplated to be particularly useful.

Naturally, in a clinical context, the quantity and volume of the peptide composition administered will depend on the host animal and condition to be treated and the route of administration. The precise amounts of active peptide required to be administered will depend on the judgment of the practitioner and may be peculiar to each individual. However, in light of the data presented herein, the determination of a suitable dosage range for use in humans will be straightforward. For example, in treating ARDS or cystic fibrosis, doses in the order of about 0.83 mg/kg body weight/hour (mg/kg/hr) to about 16.56 mg/kg/hr, preferably about 0.83 mg/kg/hr to about 4.14 mg/kg/hr, and more preferably about 1.66 mg/kg/hr of active ingredient peptide per individual are contemplated.

The compositions for use in inhibiting CXC intercrines, such as IL-8, GRO and MIP2α or MIPβ, in accordance with the present invention will be compositions that contain a relatively small peptide, generally of from 6 to about 14 residues in length, which includes within its sequence the amino acid sequence RRWWCX (SEQ ID NO:23). The term "a peptide" in this sense means at least one peptide, and may refer to one or more such peptides which include a sequence in compliance with the general formula RRWWCX (SEQ ID NO:23).

The relatively small peptides encompassed by the present invention may be any length between six residues and about 14 or 15 or so residues in length, with the precise length not being an important feature of the invention. There are many advantages to using smaller peptides, for example, the cost and relative ease of large scale synthesis, and their improved pharmacological properties, such as the ease with which they can penetrate tissues and their low immunogenicity.

In addition to including an amino sequence in accordance with the sequence RRWWCX (SEQ ID NO:23), the peptides may include other short peptidyl sequences of various amino acids. For example, in certain embodiments, the peptides may include a repeat of the sequence RRWWCX (SEQ ID NO:23) or RRWWCXX (SEQ ID NO:57). They may also contain additional sequences including, e.g, short targeting sequences, tags, labeled residues, amino acids contemplated to increase the half life or stability of the peptide, or indeed, any additional residue desired for any purpose, so long as they still function to inhibit intercrines such as IL-8—which can be readily determined by a simple assay such as those described herein.

Amino acids which may incorporated into the peptides include all of the commonly occurring amino acids. Two designations for amino acids are used interchangeably throughout this application, as is common practice in the art: Alanine=Ala (A); Arginine=Arg (R); Aspartic Acid=Asp (D); Asparagine=Asn (N); Cysteine=Cys (C); Glutamic Acid=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

Any of the so-called rare or modified amino acids may also be incorporated into a peptide of the invention, including the following: 2-Aminoadipic acid, 3-Aminoadipic acid, beta-Alanine (beta-Aminopropionic acid), 2-Aminobutyric acid, 4-Aminobutyric acid (piperidinic acid), 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylglycine, N-Ethylasparagine, Hydroxylysine, allo-Hydroxylysine, 3-Hydroxyproline, 4-Hydroxyproline, Isodesmosine, allo-Isoleucine, N-Methylglycine (sarcosine), N-Methylisoleucine, N-Methylvaline, Norvaline, Norleucine and Ornithine.

The inhibitory compositions of the invention may include a peptide modified to render it biologically protected. Biologically protected peptides have certain advantages over unprotected peptides when administered to human subjects and, as disclosed in U.S. Pat. No. 5,028,592 (incorporated herein by reference), protected peptides often exhibit increased pharmacological activity, as was found to be true in the present case.

The present invention therefore encompasses compositions comprising an acylated peptide or peptides, and preferably, a peptide acylated at the N-terminus. Although virtually any acyl group may be employed in this context, the inventors have found that the addition of an acetyl group to the N-terminus of a given peptide also renders the resultant peptide surprisingly effective at inhibiting intercrines such as IL-8. The inhibitory peptide compositions may also include a peptide(s) which is amidated at the C-terminus, i.e., to which an $NH_2$ group has been added. In particularly preferred embodiments, peptides which have both an acylated N-terminal and an amidated C-terminal residue are preferred as they are believed to most closely mimic natural protein and peptide structure.

Compositions for use in the present invention may also comprise peptides which include all L-amino acids, all D-amino acids or a mixture thereof. The finding that peptides composed entirely of D-amino acids have potent inhibitory activity is particularly important as such peptides are known to be resistant to proteases naturally found within the human body and are less immunogenic and can therefore be expected to have longer biological half lives.

The anti-intercrine and anti-IL-8 compositions of the present invention will generally comprise one or more peptides which include an amino acid sequence in accordance with those set forth in SEQ ID NO:1 or SEQ ID NOs:24 through 42. In certain embodiments, short hexamer peptides may be preferred. In such cases, the inhibitory compositions will generally comprise one or more peptides which have an amino acid sequence in accordance with those set forth in SEQ ID NO:1 or SEQ ID NOs:24 through 42, presented below:

| | |
|---|---|
| Arg Arg Trp Trp Cys Arg | (SEQ ID NO:1) |
| Arg Arg Trp Trp Cys Ala | (SEQ ID NO:24) |
| Arg Arg Trp Trp Cys Cys | (SEQ ID NO:25) |
| Arg Arg Trp Trp Cys Asp | (SEQ ID NO:26) |
| Arg Arg Trp Trp Cys Glu | (SEQ ID NO:27) |
| Arg Arg Trp Trp Cys Phe | (SEQ ID NO:28) |
| Arg Arg Trp Trp Cys Gly | (SEQ ID NO:29) |
| Arg Arg Trp Trp Cys His | (SEQ ID NO:30) |
| Arg Arg Trp Trp Cys Ile | (SEQ ID NO:31) |
| Arg Arg Trp Trp Cys Lys | (SEQ ID NO:32) |
| Arg Arg Trp Trp Cys Leu | (SEQ ID NO:33) |
| Arg Arg Trp Trp Cys Met | (SEQ ID NO:34) |
| Arg Arg Trp Trp Cys Asn | (SEQ ID NO:35) |
| Arg Arg Trp Trp Cys Pro | (SEQ ID NO:36) |
| Arg Arg Trp Trp Cys Gln | (SEQ ID NO:37) |
| Arg Arg Trp Trp Cys Ser | (SEQ ID NO:38) |
| Arg Arg Trp Trp Cys Thr | (SEQ ID NO:39) |
| Arg Arg Trp Trp Cys Val | (SEQ ID NO:40) |
| Arg Arg Trp Trp Cys Trp | (SEQ ID NO:41) |
| Arg Arg Trp Trp Cys Tyr | (SEQ ID NO:42) |

In other embodiments, the inhibitory compositions of the invention may include one or more peptides which include a sequence in accordance with the amino acid sequence Arg Arg Trp Trp Cys Arg $Xaa_2$ (SEQ ID NO:2). In these cases one of the variable positions has been defined as arginine and the remaining $Xaa_2$ may be any amino acid residue. Such sequences are exemplified by those set forth in SEQ ID NOs:3 through 22. Where short heptamer peptides are preferred, the compositions will generally comprise one or more peptides which have an amino acid sequence in accordance with those set forth below:

| | |
|---|---|
| Arg Arg Trp Trp Cys Arg Ala | (SEQ ID NO:3) |
| Arg Arg Trp Trp Cys Arg Cys | (SEQ ID NO:4) |
| Arg Arg Trp Trp Cys Arg Asp | (SEQ ID NO:5) |
| Arg Arg Trp Trp Cys Arg Glu | (SEQ ID NO:6) |
| Arg Arg Trp Trp Cys Arg Phe | (SEQ ID NO:7) |
| Arg Arg Trp Trp Cys Arg Gly | (SEQ ID NO:8) |
| Arg Arg Trp Trp Cys Arg His | (SEQ ID NO:9) |
| Arg Arg Trp Trp Cys Arg Ile | (SEQ ID NO:10) |
| Arg Arg Trp Trp Cys Arg Lys | (SEQ ID NO:11) |
| Arg Arg Trp Trp Cys Arg Leu | (SEQ ID NO:12) |
| Arg Arg Trp Trp Cys Arg Met | (SEQ ID NO:13) |
| Arg Arg Trp Trp Cys Arg Asn | (SEQ ID NO:14) |
| Arg Arg Trp Trp Cys Arg Pro | (SEQ ID NO:15) |
| Arg Arg Trp Trp Cys Arg Gln | (SEQ ID NO:16) |
| Arg Arg Trp Trp Cys Arg Arg | (SEQ ID NO:17) |
| Arg Arg Trp Trp Cys Arg Ser | (SEQ ID NO:18) |
| Arg Arg Trp Trp Cys Arg Thr | (SEQ ID NO:19) |
| Arg Arg Trp Trp Cys Arg Val | (SEQ ID NO:20) |
| Arg Arg Trp Trp Cys Arg Trp | (SEQ ID NO:21) |
| Arg Arg Trp Trp Cys Arg Tyr | (SEQ ID NO:22) |

The invention also contemplates the use of peptides having the amino acid sequence Gln Ile Pro Arg Arg Ser Trp Cys Arg Phe Leu Phe (SEQ ID NO:52), either alone, or more preferably, in combination with one or more of the other peptides described above. The successful use of this dodecamer illustrates both the fact that longer peptides are successful and that certain biologically functional equivalent peptides are active. All such active equivalents therefore fall under the scope of the present invention.

The compositions for use in the inhibitory methods described herein may contain only a single active peptidyl species. Alternatively, they may contain more than one peptide, up to and including about 40 or 45 or so distinct peptides. Any and all of the various combinations are contemplated, such as compositions comprising 2, 3, 5, 10, 15, 20, 30 or 45 or so distinct peptides.

Compositions comprising peptides having the amino acid sequence Arg Arg Trp Trp Cys Arg (SEQ ID NO:1) and/or the amino acid sequence Arg Arg Trp Trp Cys Arg Cys (SEQ ID NO:4) are contemplated to be particularly useful, although the invention is not limited to these peptides in any way. In this regard, it is important to note that considerations other than in vitro activity, such as plasma half life and stability, may be considered in ultimately choosing peptides which are preferred for clinical embodiments. The effects of different amino acid substitutions on these parameters may be readily determined and the results used to design the optimum peptide or combination of peptides for use in vivo.

The RRWWCX (SEQ ID NO:23) sequence element is an important feature of the peptides of this invention. However, this does not exclude certain biological functional equivalents from falling within the scope of the invention. For example, the inventors have discovered that the first tryptophan in RRWWCX (SEQ ID NO:23) can be exchanged, e.g., by replacing with serine, with only modest loss of activation. Therefore, one example of equivalents encompassed by the invention are peptides of the sequence RRX-WCX (SEQ ID NO:58). "Equivalent amino acids" may be defined as amino acids whose hydrophilic or hydropathic index are within ±2, more preferably, within ±1, and most preferably, within ±0.5 of each other. Of course, to be a "functional equivalent", a peptide must still retain its intercrine or IL-8 inhibitory activity, as may be easily determined using assays such as those disclosed herein.

In addition to the peptidyl compounds described herein, the inventors also contemplate that other sterically similar compounds, called peptidomimetics, may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

The peptides and compositions for use in the invention may be prepared by any one of a variety of different methods. One preferred method for preparing peptides in accordance with the present invention is contemplated to be via automated peptide synthesis. A synthetic peptide may be straightforwardly prepared using an automated peptide synthesizer, the operation of which will be generally known to those of skill in the art. This method is one of those generally preferred for preparing large quantities of a given peptide, e.g., once a particular peptide has been chosen for therapeutic use.

Another preferred method for preparing inhibitory peptides, and the biological functional equivalents thereof, is to use a combinatorial peptide library method, as described by Houghten et al. (1991) and disclosed in International Patent Application PCT WO 92/09300, the entire disclosure of which is specifically incorporated herein by reference. These methods are particularly useful for preparing and analyzing a plurality of peptides having a substantially predetermined sequence, such as RRWWC, to which is appended a variety of different amino acids at one or more positions. These methods may be used to synthesize a peptide mixture for direct use in the formulation of a composition in accordance with the invention or to identify a particularly active peptide for subsequent individual synthesis.

If desired, peptides may also by prepared by molecular biological means and the "recombinant" peptide obtained from recombinant host cells which express the peptide. To achieve this, one would prepare a specific oligonucleotide, based upon the sequence of the desired peptide, as is known to those of skill in the art, and then insert the oligonucleotide into an expression vector, such as any one of the many expression vectors currently available commercially. One would then transform a prokaryotic or eukaryotic host cell with the vector, where it will direct the expression of the so-called recombinant version of the peptide, which may then be purified from the recombinant host cell. This methodology is standard practice in the art (see e.g., Sambrook et al., 1989).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

$$\% \text{ binding inhibition} = 1 - \frac{B - NSP}{T - NSP} \times 100$$

where B is bound radioactivity in the presence of the peptide, T is bound radioactivity in the absence of the peptide, and NSP is bound radioactivity in the presence of excess nonlabeled ligand.

Figure 11A:
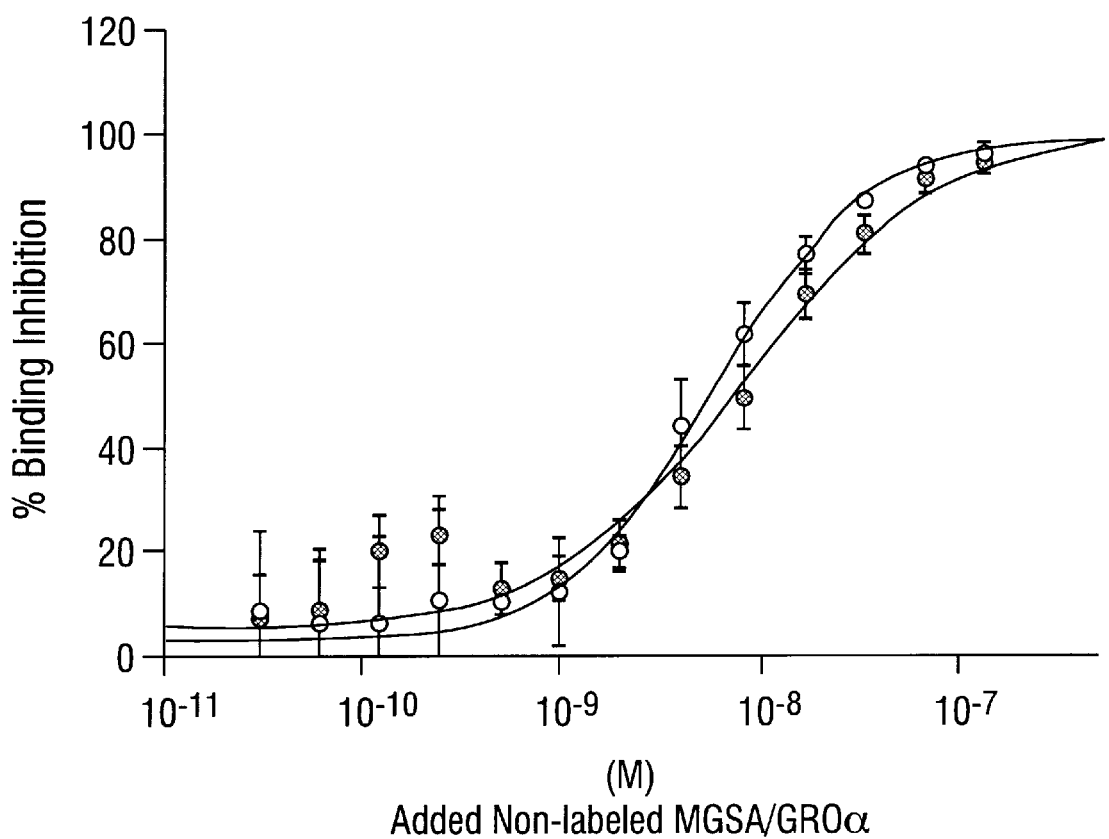

FIG. 11A. The binding of $^{125}$I-labeled MGSA/GROα to melanoma cell lines, Hs 294T and RPMI-7951. The melanoma cells, 1×10$^5$ were incubated with 1 nM I-MGSA/GROα in the presence of various concentrations of unlabeled MGSA/GROα. Binding inhibition curve with Hs 294T (closed circles) and RPMI-7951 (open circles). The lines shown in the graph are the best fit curves calculated using the London II computer program.

Figure 1:
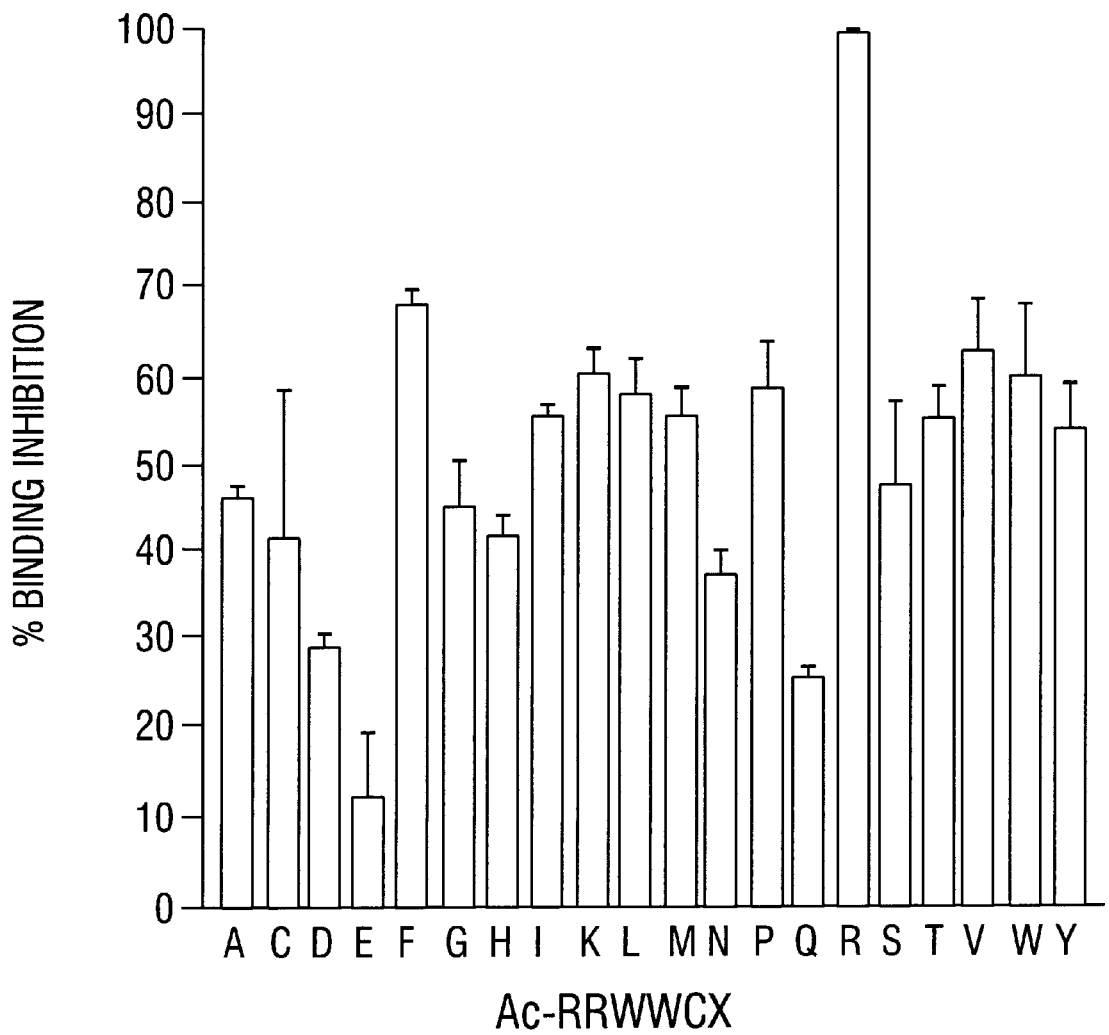
FIG. 1. Binding Inhibition by Ac-RRWWCX (SEQ ID NO:23) Series. Twenty peptides which have structure of Ac-RRWWC (SEQ ID NO:56) plus one of the 20 standard protein amino acids in the sixth position were tested. The notation on the x axis indicates the residue at the carboxy-terminal position (SEQ ID NO:1 and 24 through 42). In this study, neutrophils were incubated with 1 pM $^{125}$I-labeled IL-8 and 20 μM of each peptides.
Figure 11B:
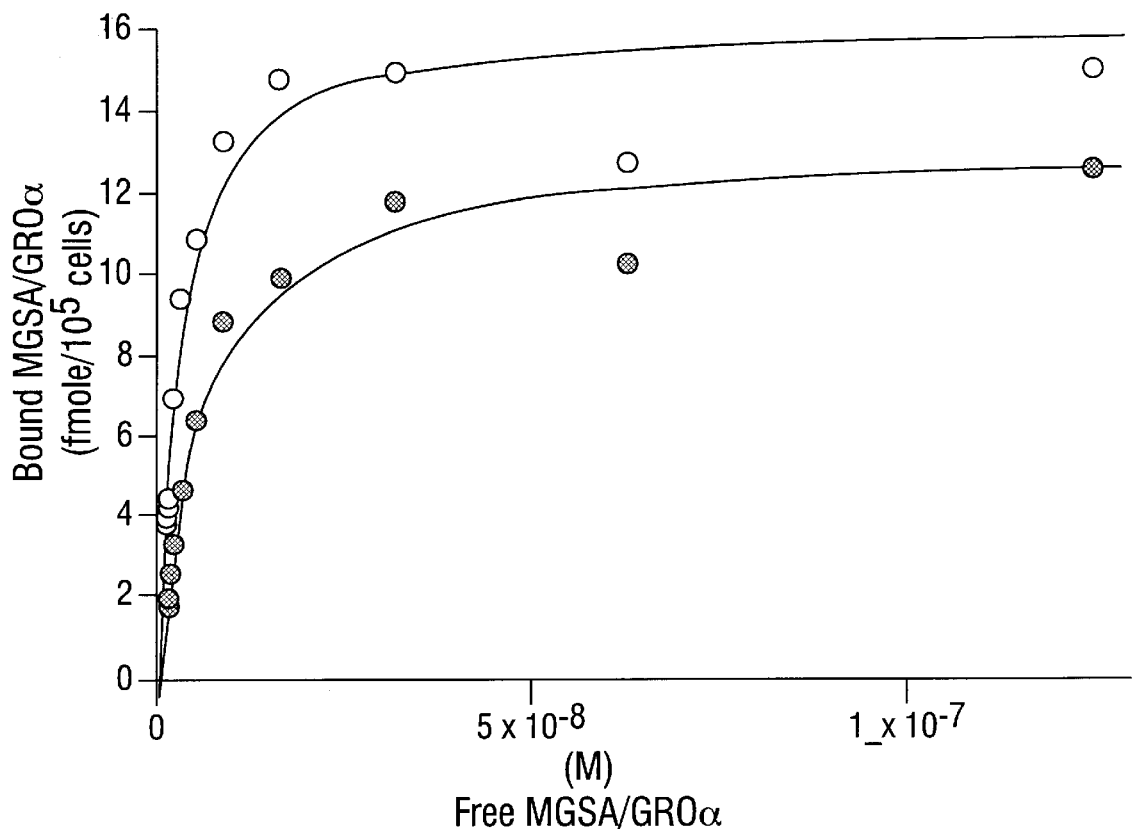

FIG. 11B. The binding of $^{125}$I-labeled MGSA/GROα to melanoma cell lines, Hs 294T and RPMI-7951. The melanoma cells, 1×10$^5$, were incubated with 1 nM $^{125}$I-MGSA/GROα in the presence of various concentrations of unlabeled MGSA/GROα. Binding isotherm transformation. The total amount of labeled and unlabeled MGSA/GROα bound to the cells were calculated. Scatchard plots were shown (FIG. 11B-1).

Figure 12:
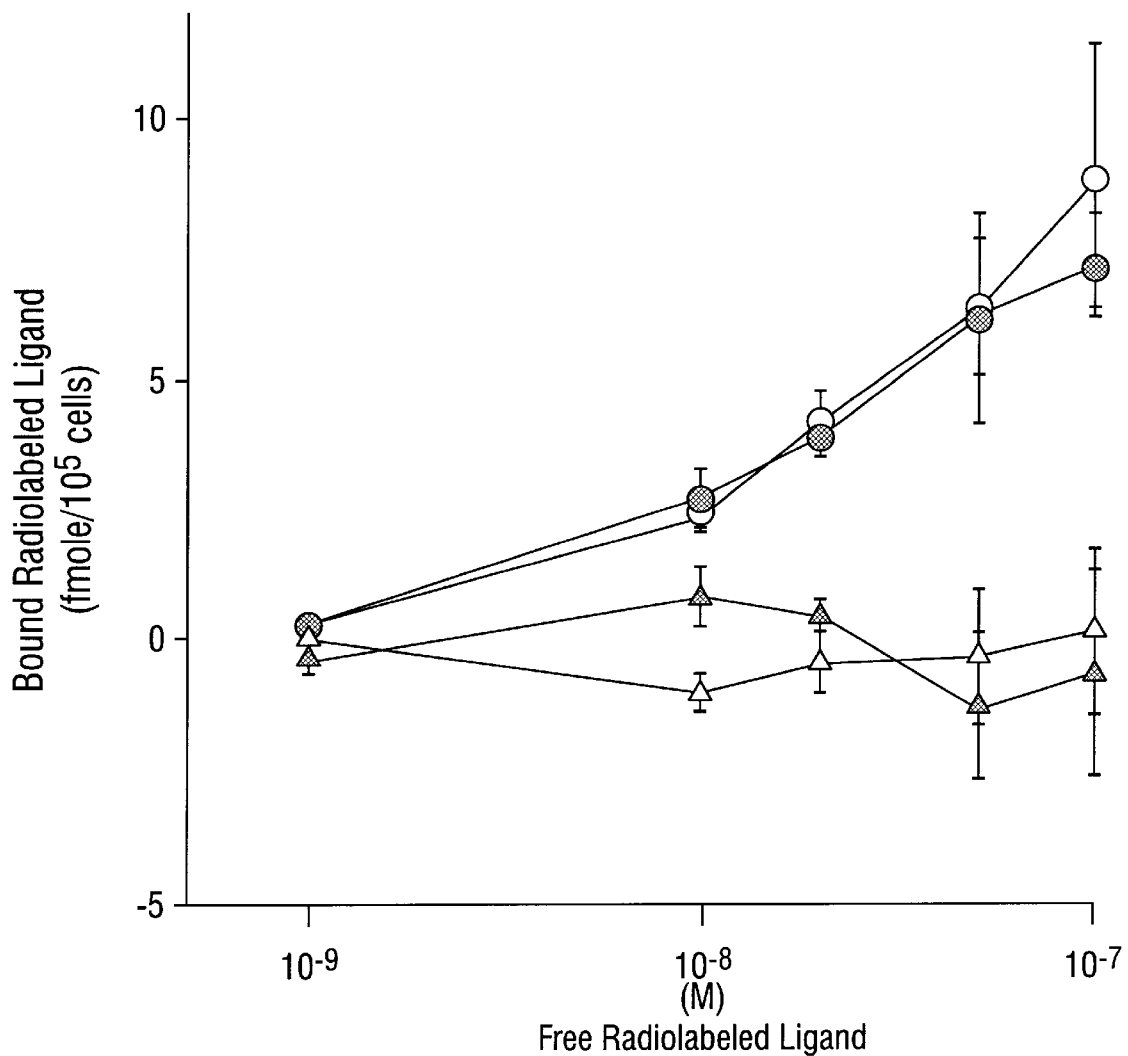

FIG. 12. The specificity of the receptor binding. The melanoma cells, Hs 294T (closed symbols) and RPMI-7951 (open symbols), were incubated with indicated concentrations of radiolabeled MGSA/GROα (circles) or IL-8 (triangles). The non-specific binding was estimated by the binding in the presence of 100 fold excess of unlabeled material. Specific binding which is calculated by subtracting non-specific binding from total binding is shown in this figure. IL-8 did not bind specifically to the melanoma cells.

Figure 13:
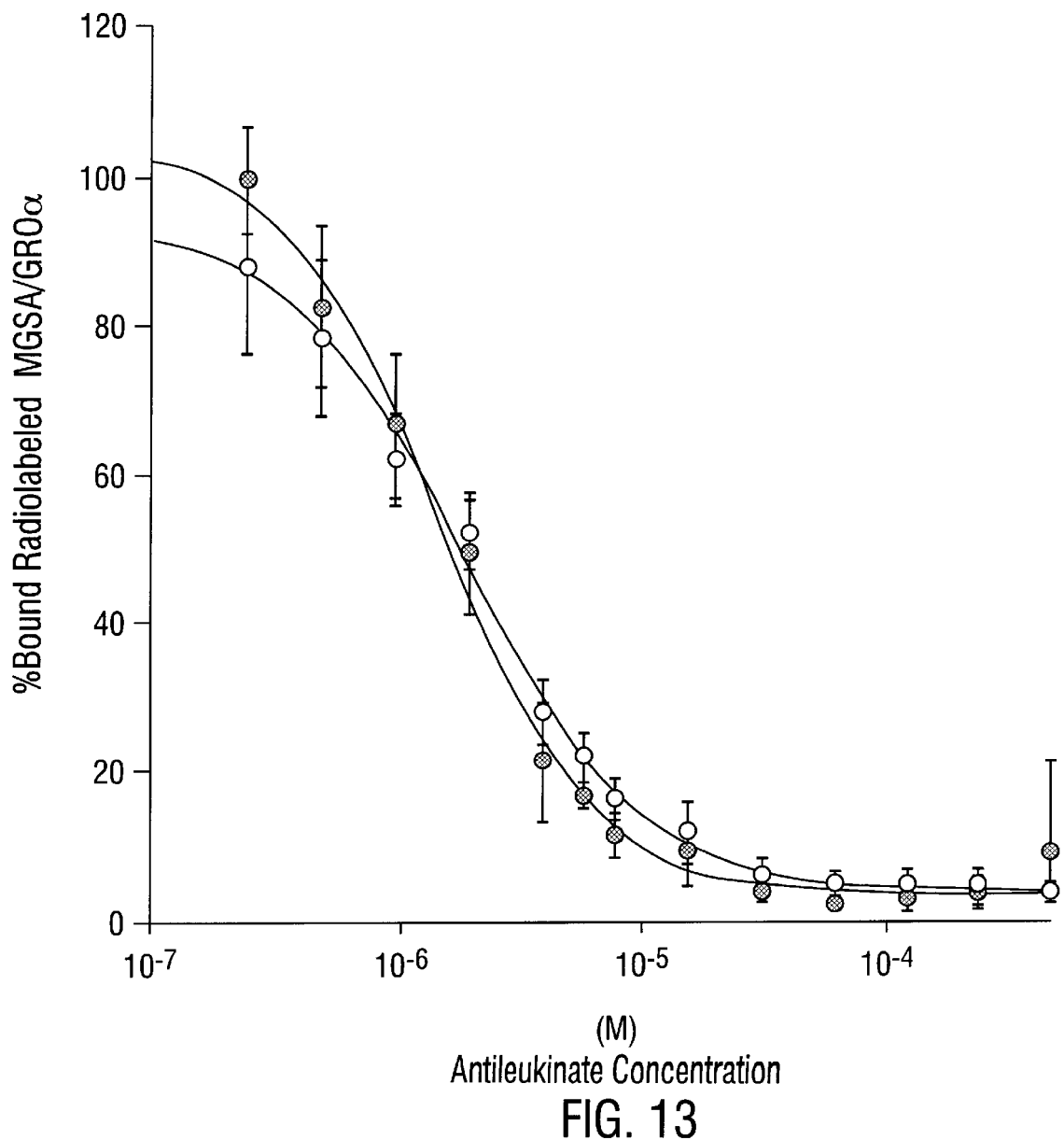

FIG. 13. The effect of Antileukinate on the binding of radiolabeled MGSA/GROα to the melanoma cell lines. The melanoma cells, Hs 294T (closed circles) and RPMI-7951 (open circles), were incubated with 1 nM $^{125}$I-MGSA/GROα in the presence of different concentrations of Antileukinate. The lines shown in the graph are the best fit curves calculated using the London II computer program.

Figure 14A:
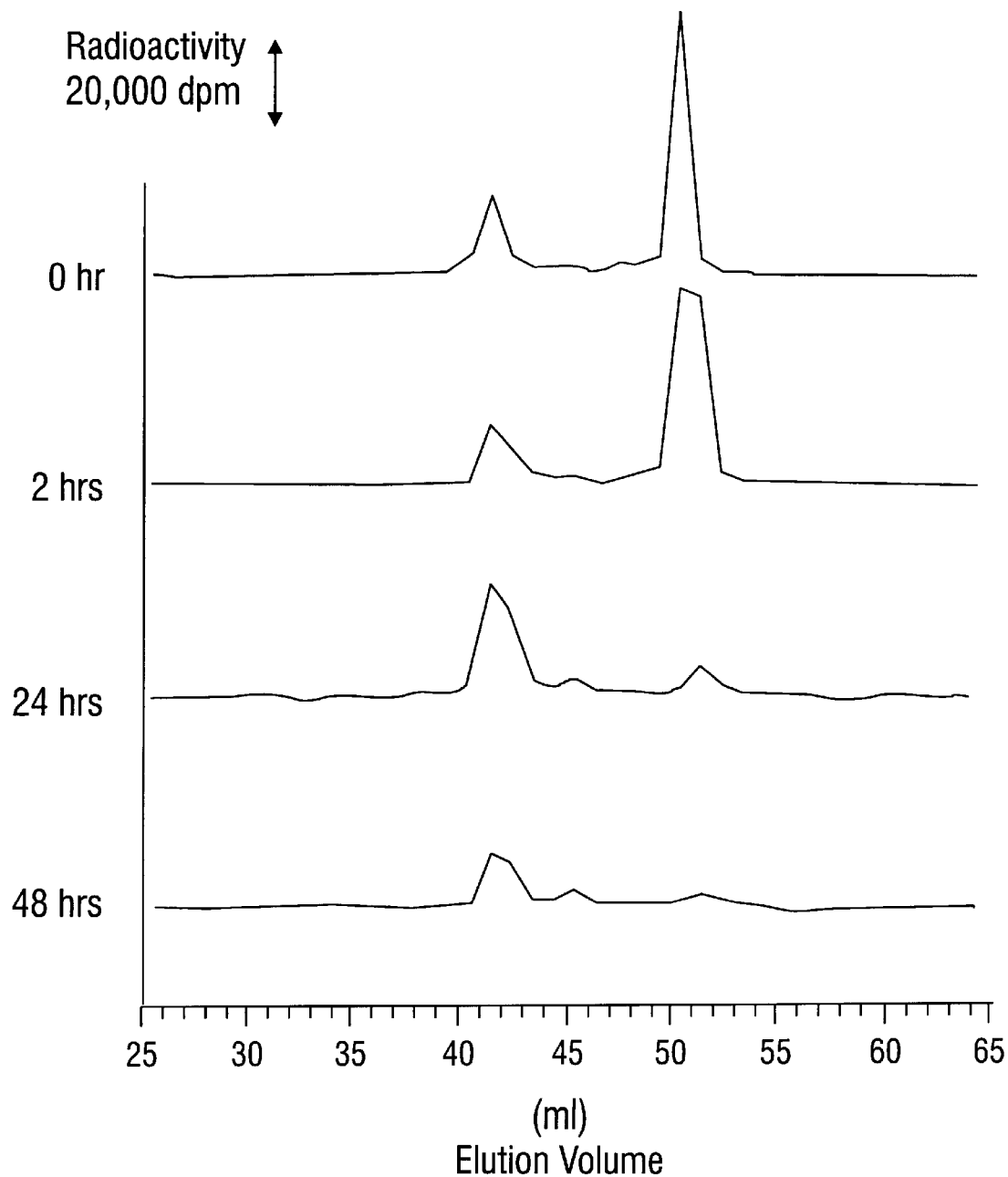

FIG. 14A. Analysis for the breakdown of Antileukinate in the culture of Hs 294T cells. A total concentration of tritium labeled and unlabeled Antileukinate of 100 μM, was added to the culture of Hs 294T cells. Aliquots of medium were removed at different times and chromatographed on an HPLC Bondapak C 18 reversed phase column. The peptides were eluted using a gradient from 0.1% TFA to 80% acetonitrile in 0.1% TFA. One milliliter fractions were collected and measured for their radioactivity using a liquid scintillation counter. The chromatographs show the elution volume of the radioactivity at different times after addition to the cells. The peptide is substantially eliminated from the culture within 24 hr.

Figure 14B:
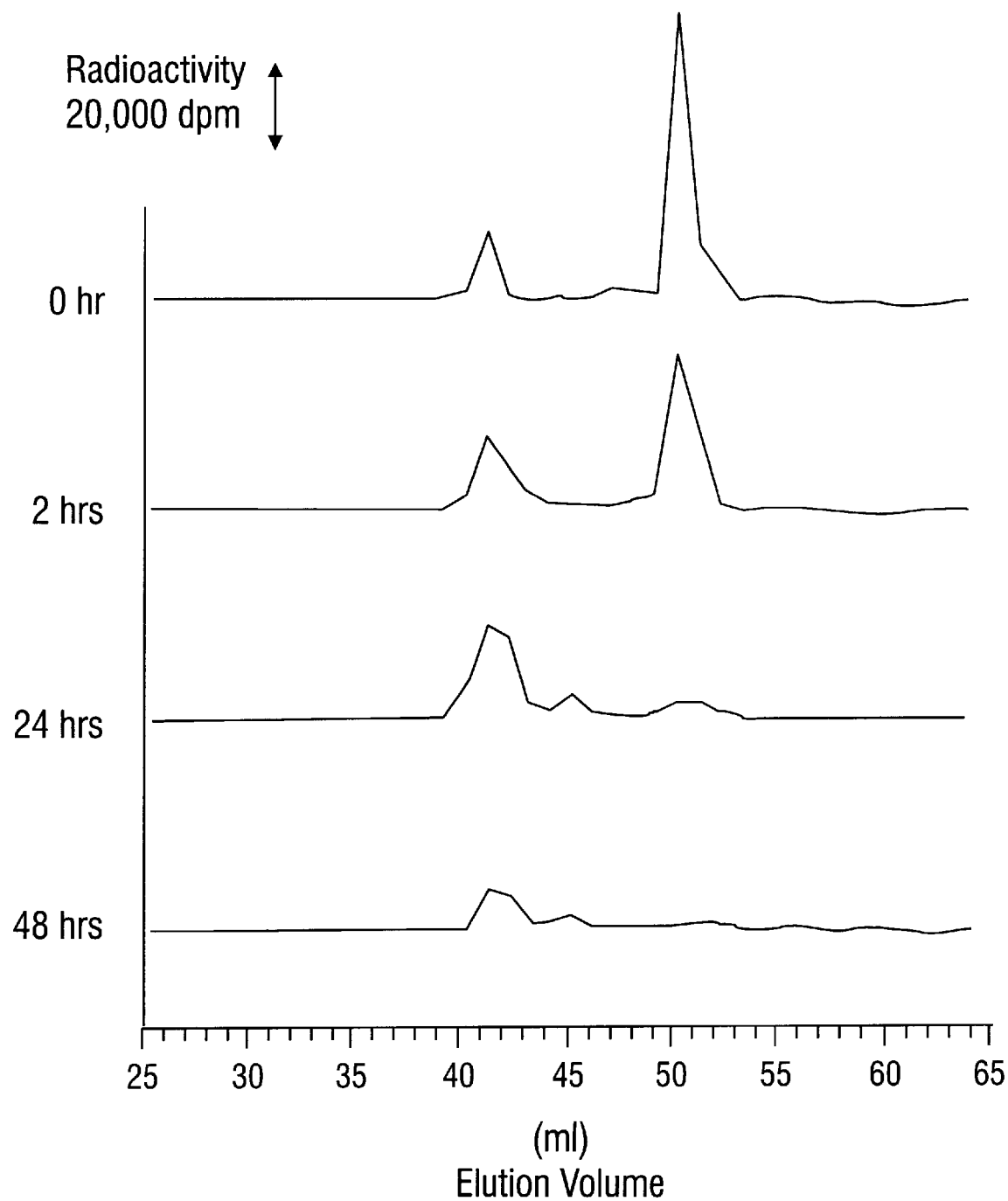

FIG. 14B. Analysis for the breakdown of Antileukinate in the culture of Hep G2 cells. A total concentration of tritium labeled and unlabeled Antileukinate of 100 μM, was added to the culture of Hep G2 cells. Aliquots of medium were removed at different times and chromatographed on an HPLC Bondapak C18 reversed phase column. The peptides were eluted using a gradient from 0.1% TFA to 80% acetonitrile in 0.1% TFA. One milliliter fractions were collected and measured for their radioactivity using a liquid scintillation counter. The chromatographs show the elution volume of the radioactivity at different times after addition to the cells. The peptide is substantially eliminated from the culture within 24 hr.

Figure 15A:
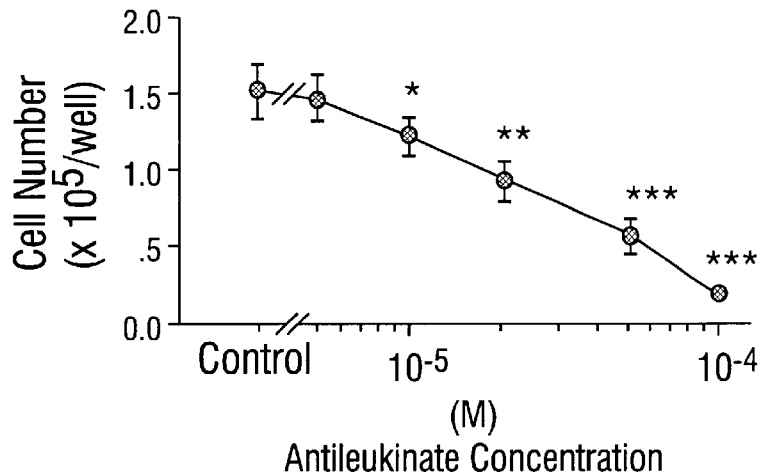

FIG. 15A. The effect of Antileukinate on the growth of melanoma cells. Melanoma cell lines and a control liver cancer cell line (2×10$^4$ cells/well) in 500 μl were cultured in a 24 well tissue culture plate in the presence of various concentrations of Antileukinate for 3 d. The culture media were changed to fresh media containing the same concentration of Antileukinate every 24 hr during the incubation period. After incubation, the cells were collected and the cell number was counted using a hemocytometer. Hs 294 T cell line. Analysis of variance was used for multiple comparison. When there was significant difference, the differences between the number of cell without the peptide and those with peptide were tested using The Sheffe's Test; *,p<0.05, ,p<0.01, *,p<0.001.

Figure 15B:
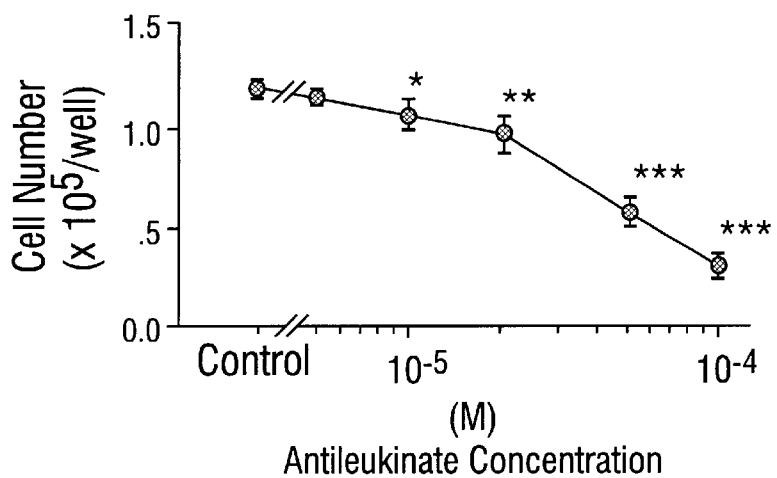

FIG. 15B. The effect of Antileukinate on the growth of melanoma cells. Melanoma cell lines and a control liver cancer cell line (2×10$^4$ cells/well) in 500 μl were cultured in a 24 well tissue culture plate in the presence of various concentrations of Antileukinate for 3 d. The culture media were changed to fresh media containing the same concentration of Antileukinate every 24 hr during the incubation period. After incubation, the cells were collected and the cell number was counted using a hemocytometer. RPMI-7951 cell line. Analysis of variance was used for multiple comparison. When there was significant difference, the differences between the number of cell without the peptide and those with peptide were tested using The Sheffe's Test; *,p<0.05, ,p<0.01, *,p<0.001.

Figure 15C:
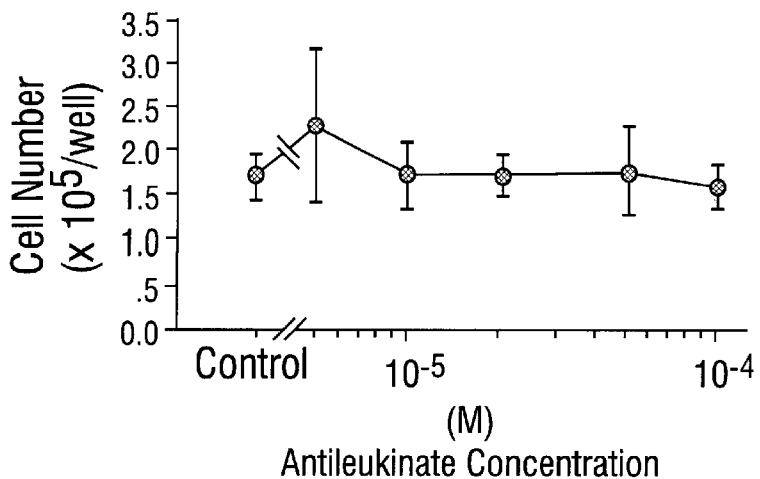

FIG. 15C. The effect of Antileukinate on the growth of melanoma cells. Melanoma cell lines and a control liver cancer cell line ($2 \times 10^4$ cells/well) in 500 $\mu$l were cultured in a 24 well tissue culture plate in the presence of various concentrations of Antileukinate for 3 d. The culture media were changed to fresh media containing the same concentration of Antileukinate every 24 hr during the incubation period. After incubation, the cells were collected and the cell number was counted using a hemocytometer. Liver cancer cell line, Hep G2. Analysis of variance was used for multiple comparison. When there was significant difference, the differences between the number of cell without the peptide and those with peptide were tested using The Sheffe's Test; *,p<0.05, ,p<0.01, *,p<0.001.

Figure 16A:
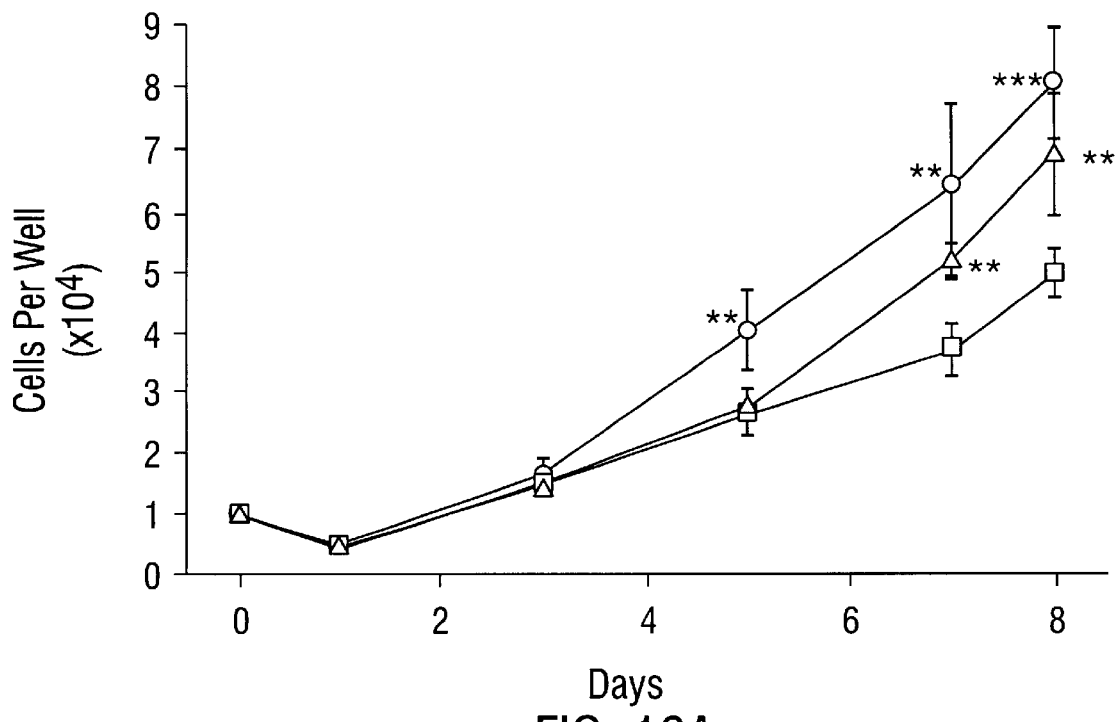

FIG. 16A. Restoration of Hs 294T cell growth inhibition by removal of Antileukinate or the addition of excess MGSA/GROα. Melanoma cell lines Hs 294T ($2 \times 10^4$ cells/well) were cultured in a 24 well tissue culture plate for 1 to 8 d, and the cell number was counted using a hemocytometer. The effect of removal of Antileukinate from the cell culture. The cell culture was started in the presence of 50 $\mu$M Antileukiante. 24 hr later, the culture media was replaced using media with Antileukinate and the culture was continued in the absence of the peptide (open triangles). The cell numbers were compared with those measured when the cells were cultured in the presence (open squares) or the absence (open circles) of the peptide throughout the culture periods. When there was significant difference, the Scheffe's Test was performed to establish the significance between two groups. The data significantly different from those with Antileukinate (+) were marked; *,p<0.05, ,p<0.01, *, p<0.001.

Figure 16B:
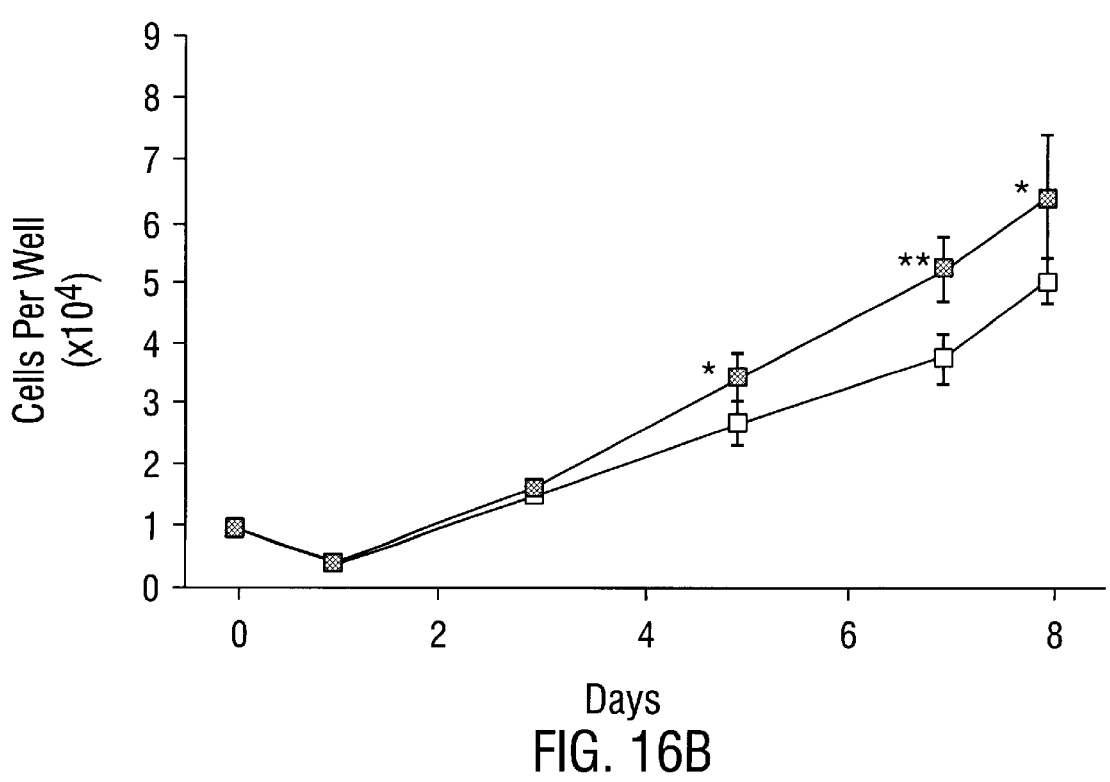

FIG. 16B. Restoration of Hs 294T cell growth inhibition by removal of Antileukinate or the addition of excess MGSA/GROα. Melanoma cell lines Hs 294T ($2 \times 10^4$ cells/well) were cultured in a 24 well tissue culture plate for 1 to 8 d, and the cell number was counted using a hemocytometer. The effect of addition of excess MGSA/GROα from the cell culture. The cell culture was started in the presence of 50 $\mu$M Antileukinate. 24 hr later, the culture media was replaced using media containing Antileukinate and 50 nM MGSA/GROα (closed squares). The cell numbers were compared with those measured when the cells were cultured in the presence of Antileukinate alone (open squares). Analysis of variance was used for multiple comparisons of the cell numbers obtained at each culture period. When there was significant difference, the Scheffe's Test was performed to establish the significance between two groups. The data significantly different from those with Antileukinate (+) were marked; *,p<0.05, ,p<0.01, *,p<0.001.

Figure 17:
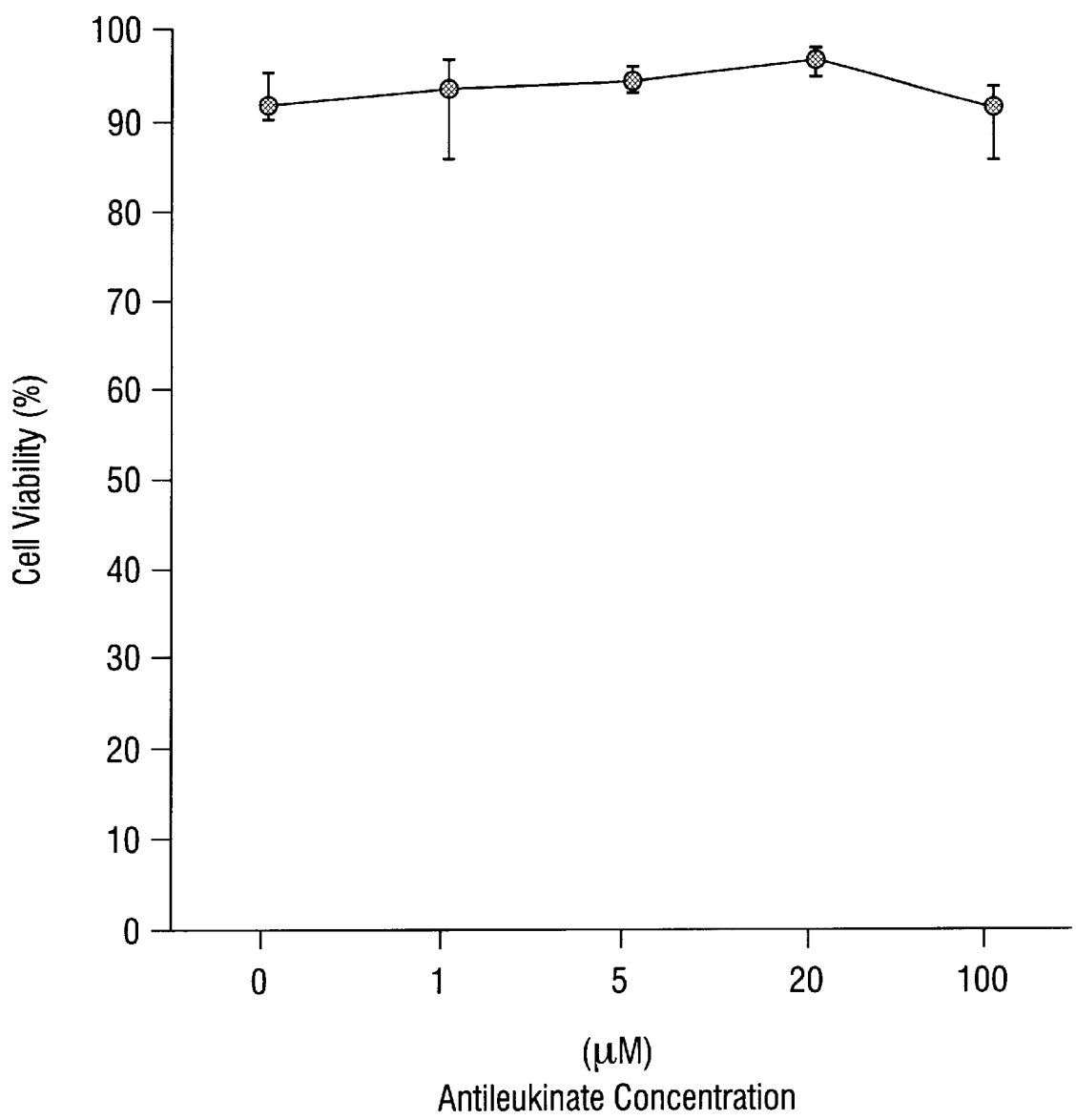

FIG. 17. The viability of Hs 294T cells after the culture for 72 hr in the presence of Antileukinate. Melanoma cell line Hs 294T was cultured in the presence of various concentrations of Antileukinate for 72 hr. The viability of the cells was measured by means of trypan blue dye exclusion. Median ±25% percentile range of the data are shown.

Figure 18:
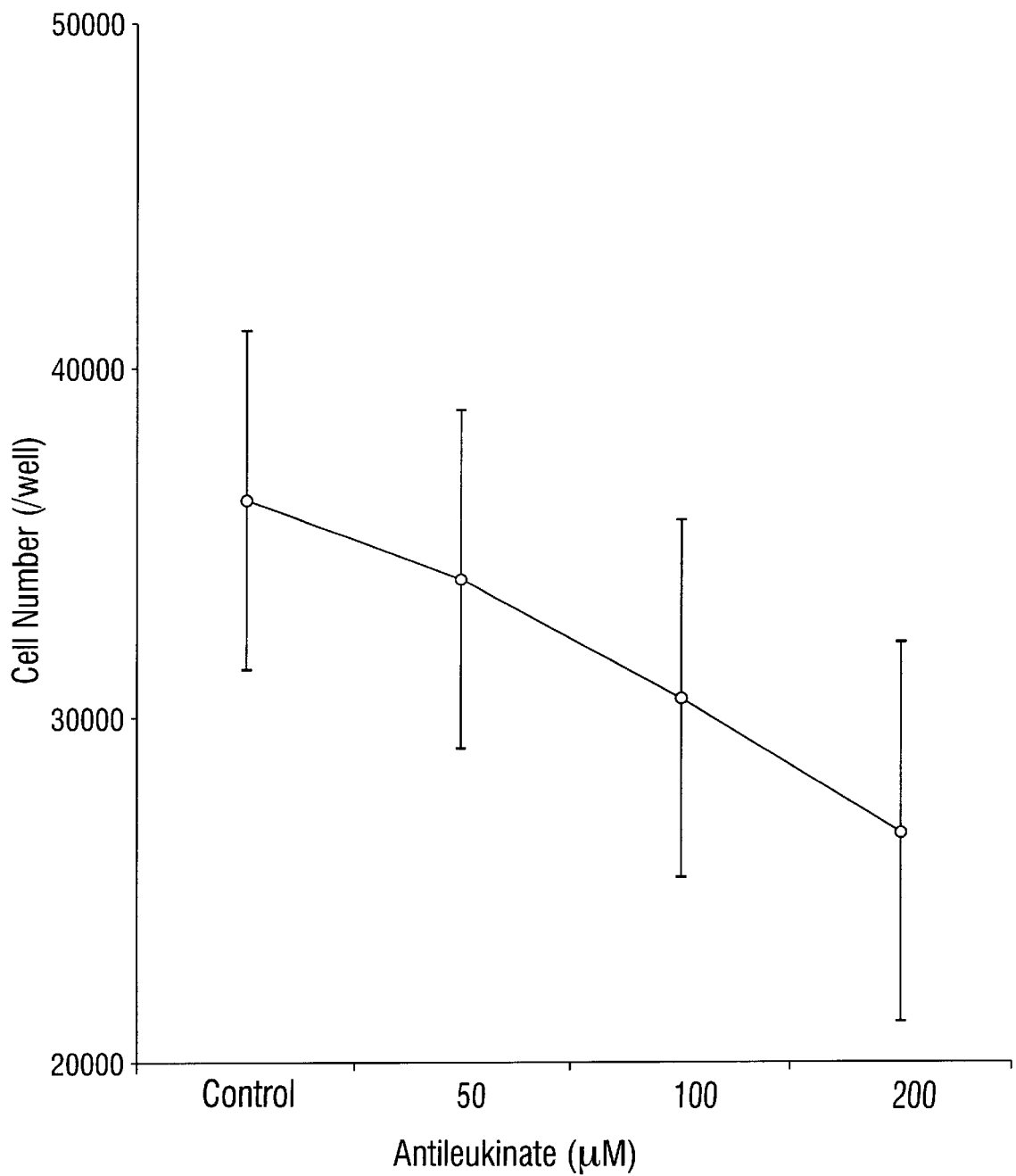

FIG. 18. The effect of Antileukinate on growth of DU145 (adenocarcinoma of prostate) cell line. Serum-starved DU145 were incubated with the indicated concentrations of Antileukinate for 24 hours. MTT assay was then performed. Cell number was decreased in a dose-dependent manner and there are significant differences from controls at concentrations greater than, or equal to 100 $\mu$M of Antileukinate (p<0.05).

Figure 19:
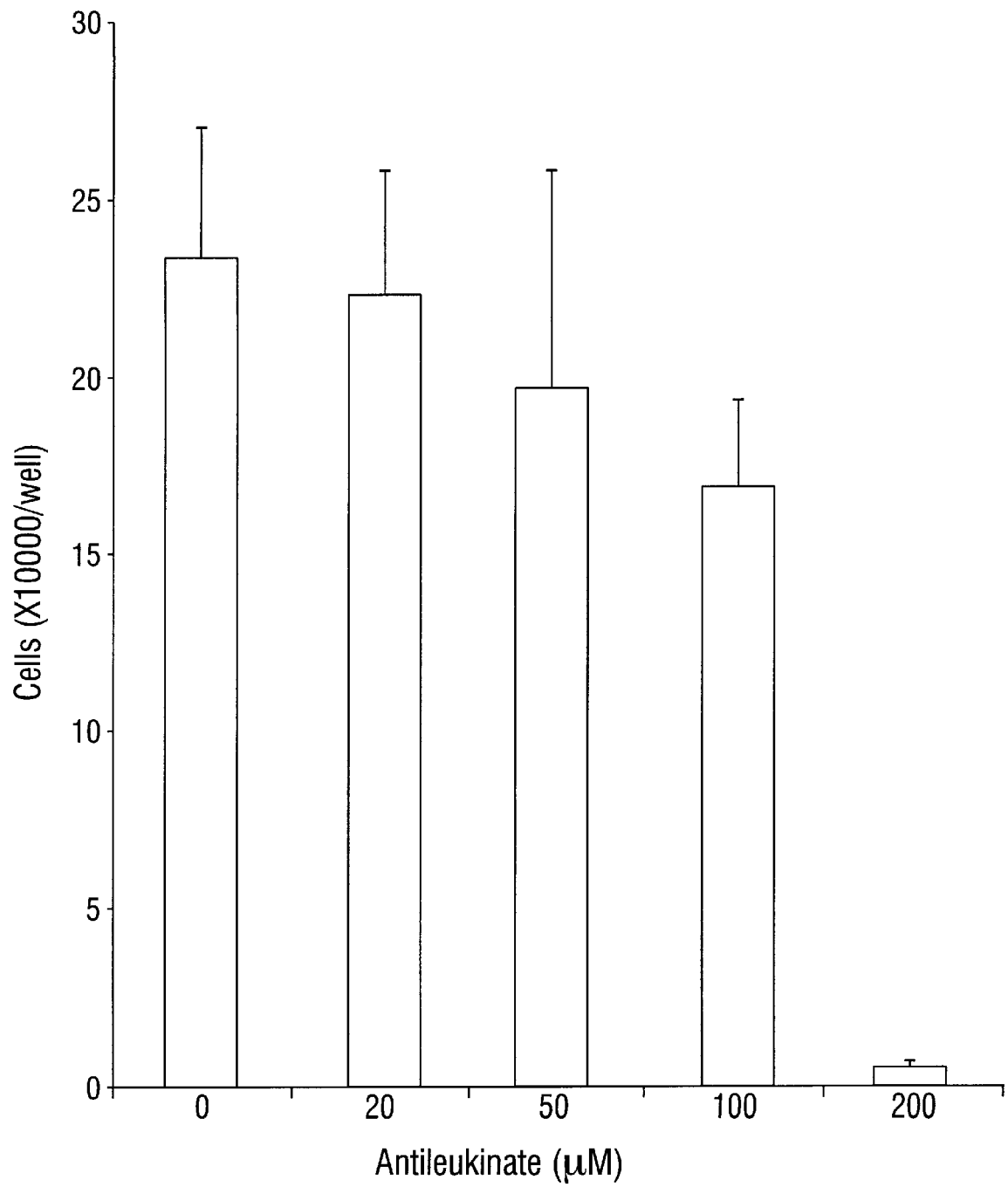

FIG. 19. The effect of Antileukinate on growth of NCI-H292 (squamous cell carcinoma of lung). NCI-H292 cells were plated at a density of $5 \times 10^3$ cells in 24-well plate with growth medium. After the cells adhered to the plate, supernatants were aspirated and culture media containing various concentrations of Antileukinate were added to the wells. The media was replaced every 24 hour and the cells were cultured for 7 days. After incubation, cells were detatched with trypsin-EDTA and the cell number was counted using a hemocytometer. Cell number was decreased in a dose-dependent manner and there are significant differences from control at concentrations greater than, or equal to 50 $\mu$M of Antileukinate (p<0.05).

Figure 20:
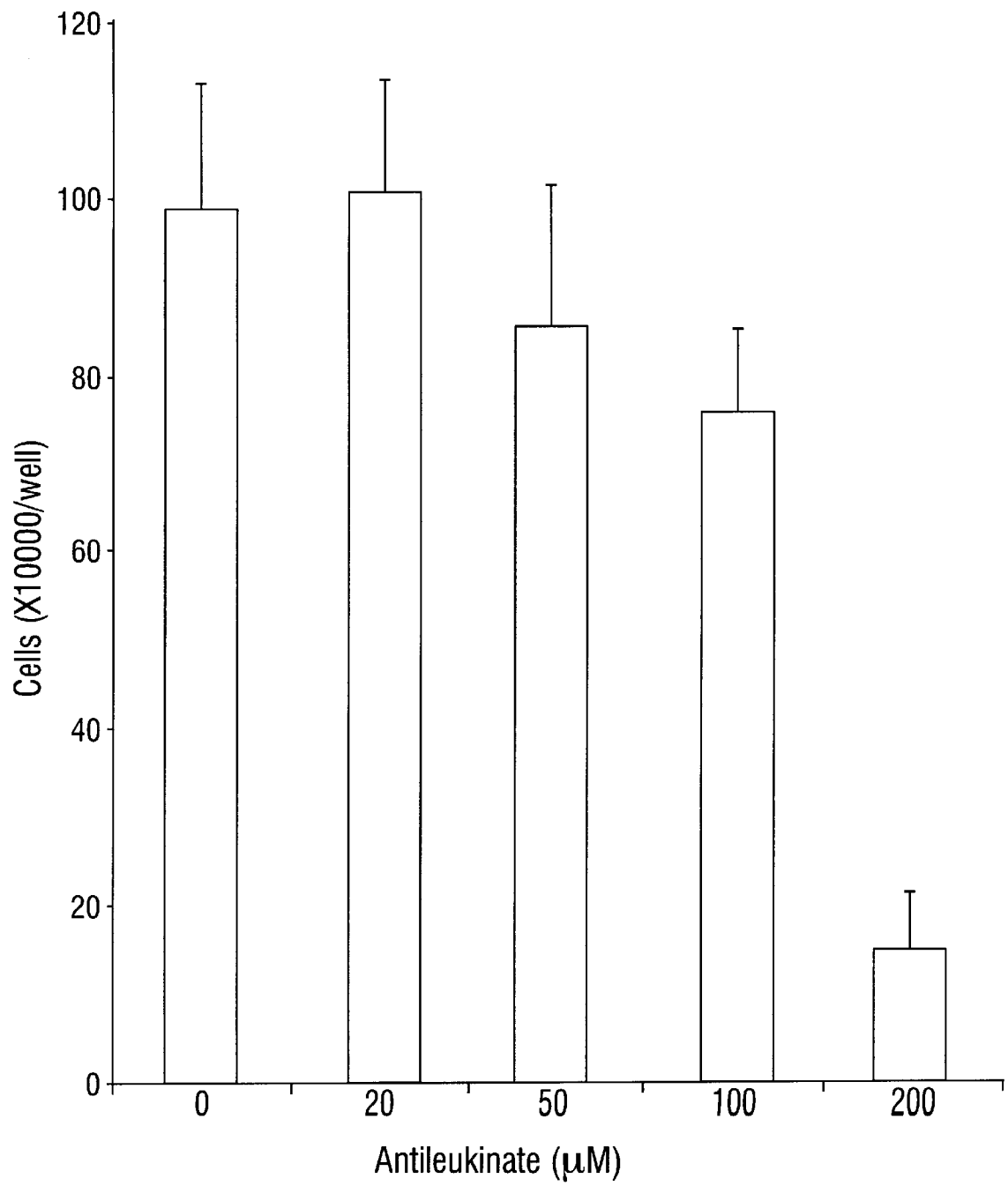

FIG. 20 The effect of Antileukinate on growth of A549 (adenocarcinoma of lung). A549 cells were plated at a density of $5 \times 10^3$ cells in 24-well plate with growth medium. After the cells adhered to the plate, supernatants were aspirated and culture media containing various concentrations of Antileukinate were added to the wells. The media was replaced every 24 hours and the cells were cultured for 7 days. After incubation, cells were detatched with trypsin-EDTA and the cell number was counted using a hemocytometer. Cell number was decreased in a dose-dependent manner and there are significant differences from control at concentrations greater than, or equal to 50 $\mu$M of Antileukinate (p<0.05).

DETAILED DESCRIPTION OF THE PREFERRED EMBODIMENTS

CXC Intercrines, IL-8 Actions and Inhibitory Peptides

IL-8 has been identified as a neutrophil activating molecule (Schroder et al., 1988; Peveri et al., 1988; Yoshimura et al., 1987). It is produced mainly by monocyte-macrophage and endothelial cell by the stimuli such as bacterial lipopolysaccharide (LPS), tumor necrosis factor or interleukin 1, and shares common neutrophil activating properties with chemotactic agonists, such as fMLP, C5a or leukotriene $B_4$ (Baggiolini et al., 1992). IL-8 can stimulate chemotaxis of neutrophils as well as enzyme release and respiratory burst. IL-8 is one member of the family of peptide molecules termed CXC intercrines, which all have the CXC sequence motif in their N-terminal region. The CXC intercrines also include GRO, MIP2α or MIP2β and, more recently, ENA78.

The functions of IL-8 are mediated by IL-8 receptors on the neutrophil surface membrane. Recent studies showed that IL-8 binds to at least two distinct receptors, whereas most of the other members of the intercrine family, e.g., GRO and MIP2β, bind to one of the receptors with high affinity (Holmes et al., 1991; Murphy and Tiffany, 1991; LaRosa et al., 1992; Cerretti et al., 1993). These receptors are different from the receptors for other chemotactic agonists (Dohlman et al., 1987).

IL-8 has been found in high concentrations in joint fluids from patients with several kinds of joint disease (Brennan et al., 1990), in pleural spaces of some patients with pleural effusions (Miller and Idell, 1993), and lung edema fluids from patients with the adult respiratory distress syndrome (ARDS) (Miller et al., 1992). Increased IL-8 levels have also been clearly documented in various recent studies of patients with cystic fibrosis (Richman-Eisenstat et al., 1993; McElvaney et al., 1992; Nakamura et al., 1992; Bedard et al., 1993).

IL-8 activates neutrophils and, although they are powerful antimicrobial cells, neutrophils can also cause considerable tissue damage through the release of certain enzymes. IL-8 is therefore believed to be important in pathogenesis of these and other inflammatory disorders. The inventors therefore hypothesized that modulation of IL-8 function would be a good strategy to control various diseases and pathological conditions, particularly ARDS and cystic fibrosis.

Recently, results from various studies attempting to modify IL-8 function have been reported. These include studies showing some success in inhibiting IL-8 synthesis (Standiford et al., 1992; Lam et al., 1990). Also, anti-human IL-8 has been reported to ameliorate lung inflammation in rats suffering from an immunologic injury (Mulligan et al., 1993). IL-8 secretion in airways of patients with cystic fibrosis was reportedly reduced with the secretory leukoprotease inhibitor of neutrophil elastase (McElvaney et al., 1992). In addition, IL-8 production has been shown to be suppressed in LPS-stimulated whole human blood by oxygen radical scavengers (DeForge et al., 1992). Finally, two cytokines, interferon gamma (Cassatella et al., 1993a; 1993b) and interleukin 4 (Standiford et al., 1990) inhibited the synthesis of IL-8. However, such work has yet to yield a particularly effective IL-8 inhibitor, or an inhibitor capable of preferentially inhibiting certain neutrophil responses over others.

Studies have also been conducted on the interaction of IL-8 with its receptors. This has led to the identification of certain peptide inhibitors with structures corresponding to portions of the IL-8 molecule. For example, Gayle and colleagues found that the 44 amino acids at the amino-terminal end of the rabbit IL-8 receptor was a moderately good inhibitor of IL-8 binding and function (Gayle et al., 1993). The present inventors have shown that synthetic peptides, and particularly, IL-8 amino terminal peptides, inhibit IL-8 binding to neutrophils and neutrophil chemotaxis (Miller et al., 1990; Miller et al., 1993). An N-terminal pentapeptide IL-8 inhibitor has also been reported (Goodman et al., 1991).

Nonetheless, effective peptide inhibitors have not yet been developed from a knowledge of the structure of the IL-8 molecule. Therefore, in pursuing this aim, the present inventors assayed various other peptide compositions for IL-8 inhibitory activity by screening a library of 400 groups of hexapeptides. In these screening assays, $^{125}$I-labeled interleukin-8 ($10^{-12}$M) was mixed with 100 μM peptide, then added to neutrophils and incubated at 4° C. for 90 min. The bound radioactivity was separated from unbound by centrifugation through a dense cushion of a mixture of paraffin and silicon oils and the $^{125}$I bound to neutrophils was counted in a gamma radiation spectrometer, allowing the results to be expressed as the percent of IL-8 binding which was inhibited.

In these studies, hexamers of the sequence RRWWCX (SEQ ID NO:23), where the terminal position may be any amino acid, were found to be effective IL-8 inhibitors. Although certain RRWWCX-type peptides had previously been found to exhibit anti-Staphylococcal properties (Houghten et al., 1991), no other functional properties have been reported which would suggest these peptides to have either anti-cytokine or anti-inflammatory activities. The present inventors also showed that RRWWCR effectively inhibits other CXC intercrines, such as GRO and MIP2, as evidenced by reducing GRO and MIP2β binding to human neutrophils.

Although all RRWWCX (SEQ ID NO:23) series peptides have anti-IL-8 activity (Table 1 A and Table 1 B), the peptide RRWWCR (SEQ ID NO:1) was found to be particularly effective. A form of this peptide with an amino-terminus acetyl group and a carboxy-terminus amino group (Ac-RRWWCR-NH$_2$; SEQ ID NO:1), thus modified in order to resemble peptides present among longer sequence of protein, became one of the focal points of these studies.

Ac-RRWWCR-NH$_2$ (SEQ ID NO:1) was found to inhibit the specific binding of $^{125}$I-labeled IL-8 to neutrophils with an apparent K, of approximately 10 μM, and to be almost twice as effective as the non-acetylated form of the same peptide. A precise K$_I$ value could not be obtained due to the presence of positive cooperativity. The binding isotherm of IL-8 in the absence of the peptide fitted one-site model best, when it was analyzed using the computer program Lundon I. One possible explanation of the lower IL-8 concentration data in the Scatchard plots is that cooperativity masked the high affinity binding at low IL-8 concentrations. Recent studies, however, have shown that IL-8 bound to two distinct classes of IL-8 receptors with almost similar affinity (Lee et al., 1982; Schumacher et al., 1992). Therefore, it is more likely that the estimated Bmax for this binding site as one-site model represents the total Bmax of two class of receptors and that the estimated Kd is common for these receptors.

The binding isotherms in the presence of the peptide fit two-site model best. The analysis of binding isotherms in the presence of Ac-RRWWCR-NH$_2$ showed that this peptide suppressed the binding of IL-8 to two classes of receptors differently. The estimated values of binding parameters showed that affinity of one class of receptors was suppressed by 10 μM peptide, which suggested competitive inhibition. Higher concentration of peptide is needed to inhibit the other class of receptor non-competitively.

The activity of the present inhibitory peptides is specific for IL-8. Ac-RRWWCR-NH$_2$ does not inhibit the binding of C5a or leukotriene B$_4$ to neutrophils, chemotaxis induced by formyl-L-Met-L-Leu-L-Phe (fMLP), or β-glucuronidase release induced by fMLP, C5a or leukotriene B$_4$. It also has no intrinsic ability to cause neutrophil chemotaxis or enzyme release. These observations suggest that peptides such as Ac-RRWWCR-NH$_2$ can strongly inhibit human neutrophil activations induced by IL-8 as a result of modulation of its receptor binding.

Ac-RRWWCR-NH$_2$ (Antileukinate) is a potent inhibitor of binding of α-chemokines to the receptors on the neutrophils. Antileukinate inhibited the binding of radiolabeled IL-8 with an IC$_{50}$ of 13.7 μM. The activity of the peptide was specific for α-chemokines. Antileukinate also suppressed the binding of radiolabeled macrophage inflammatory peptide-2β (MIP-2β) to human neutrophils, while it did not affect the binding of radiolabeled MIP-1α, leukotriene B$_4$ or C5a. Antileukinate inhibited the enzyme release from neutrophils stimulated by IL-8 with an EC$_{50}$ of 0.8 μM. The peptide binds to human neutrophils, while it does not interact with IL-8. Together with the finding that some part of IL-8 binding to human neutrophil is competitively inhibited by Antileukinate, these findings suggest that Antileukinate interacts with α-chemokine receptors rather than with the ligand.

Furthermore, hexamer and heptamer peptides based upon the Ac-RRWWCR-NH$_2$ structure are contemplated to preferentially inhibit enzyme release over chemotaxis. Indeed, Ac-RRWWCR-NH$_2$ is herein shown to significantly suppress neutrophil chemotaxis induced by 10 nM IL-8 at a concentration of 50 μM and β-glucuronidase release at 2

μM, even though 10 times more IL-8 is required to cause enzyme release. This preferential inhibition of enzyme release at lower concentrations than chemotaxis is a particularly important and surprising discovery that makes these types of peptides ideal for the treatment of lung injury in patients with the adult respiratory distress syndrome.

The above findings also suggest that distinct neutrophil functions may require IL-8 binding to different classes of receptors. Although not important to the utility of the invention per se, this also makes the present peptides suitable for use as investigational tools to further elucidate IL-8 receptor and neutrophil functions.

The inventors next examined the inhibitory activity of a second set of peptides which contained Ac-rrwwcrx-NH$_2$ (SEQ ID NO:2), with all D-amino acids. Again, all RRW-WCRX (SEQ ID NO:2) series peptides were found to have anti-IL-8 activity (Table 5A and Table 5B). However, the peptide Ac-rrwwcrc-NH$_2$ (SEQ ID NO:4) was found to be the best inhibitor, being almost four times as potent an inhibitor as Ac-rrwwcr-NH$_2$ (SEQ ID NO:1). This observation is potentially of great significance as mammalian proteases cannot degrade D-amino acid peptides and proteins (Togo et al., 1989). Therefore, D-amino acid peptide inhibitors are expected to have a longer half life in vivo.

Various other synthetic peptides were also tested for their ability to inhibit IL-8 binding to neutrophils in the standard assay. These peptides were either homologues of the amino-terminal end of IL-8, or were segments of proteins found in the protein data bases (PIR or Swiss-Prot) which had five of the six residues in RRWWCR (SEQ ID NO:2). The latter peptides were identified by searching the PIR and Swiss-Prot databases for RRWWCR (SEQ ID NO:1), using the IGSUITE program to search the databases present on the CRAY computer at the Center for High Performance Computing in Austin Texas. None of the proteins in the data bases contained all six of the amino acids.

Previous studies have shown that the residues Glu, Leu and Arg at the 4, 5, and 6 positions of the 72 amino acid of IL-8 are critical for the binding to neutrophils (Clore et al., 1992; Clark-Lewis et al., 1991), and that the amino terminal peptide of IL-8 inhibits IL-8 binding to neutrophils and chemotaxis (Miller et al., 1993). The inventors therefore examined the IL-8 homologues Ac-KELRCQ-NH$_2$ (SEQ ID NO:54) and ELRCQCIKTY (SEQ ID NO:49, including the C-X-C motif characteristic of intercrine peptides), along with its two non-Cys-containing analogues, ELRSQSKTY (SEQ ID NO:50) and ELRMQMKTY (SEQ ID NO:51). None of these peptides had the ability to inhibit IL-8 binding to neutrophils.

The inventors next searched the protein databases to determine if RRWWCR (SEQ ID NO:1) might occur in other peptides which might have relevant physiologic functions in relation to IL-8. Two peptides were identified and chosen for investigation because they contained five of the six residues in RRWWCR (SEQ ID NO:1) and were contained in known proteins. They were GW<u>RRWWC</u>DAVLY (SEQ ID NO:53) and QIP<u>RRSWCR</u>FLF (SEQ ID NO:52). The former peptide is contained in "cell surface glycoprotein CD11c precursor—human leukocyte adhesion receptor p150,95 alpha chain" (Corbi et al., 1990; Accession number, A36534\A35543\S00864) and the latter is 3',5'-cyclic GMP phosphodiesterase beta chain—bovine (Ovchinnikov et al., 1987; Accession Number, S00251).

Although one of these homologues, namely QIPRR-SWCRFLF (SEQ ID NO:52), inhibited IL-8 binding to neutrophils by about 60%, this activity is less than Ac-RRWWCR-NH$_2$ (SEQ ID NO:1). It is not thought likely that the protein from which this sequence was extracted, bovine retinal 3'5'-cyclic GMP phosphodiesterase, has a physiological role in IL-8 function, but this cannot be totally ruled out. The most important data from this study suggest that the first tryptophan in RRWWCR (SEQ ID NO:1) can be modified with only modest loss of activation. The lack of activity of the other peptide, GRRWWCDAVLY (SEQ ID NO:53), suggests that changing the last Arg in RRWWCR (SEQ ID NO:1) to Asp significantly reduces its ability to inhibit IL-8 binding to neutrophils, as supported by the observation that Ac-rrwwcd (SEQ ID NO:26) is only minimally active.

Thus, the examples set forth herein detail the identification of a new series of peptide inhibitors capable of inhibiting IL-8 binding to neutrophils and neutrophil activation. The peptide inhibitors of the RRWWCX (SEQ ID NO:23) and RRWWCRX (SEQ ID NO:2) types have the distinct advantage over previously described inhibitors that they are only six or seven residues long and that the D-amino acid analogues are also active. It is contemplated that this class of inhibitors will be useful in the therapy of diseases caused by the unrestrained action IL-8, such as the adult respiratory distress syndrome. These inhibitors have the distinct advantage that they will likely permit neutrophils to enter the lungs, via chemotaxis which is not readily inhibited, but that they will then preferentially prevent the detrimental enzyme release (McGuire et al., 1982).

In addition to their many and varied therapeutic uses, the peptides and compositions of the present invention have utility in other embodiments. These include, for example, their use in various bioassays, e.g., as positive controls in assays of IL-8 inhibitors or neutrophil inhibitors; uses in further delineating IL-8 receptor interactions and functions; generating antibodies, and the like.

Biological Functional Equivalents

Certain biological functional equivalents of the RRWWCXX-type peptides are contemplated within the scope of this invention. The concept of biologically functional equivalent amino acids is well known to those of skill in the art, and is embodied in the knowledge that modifications and changes may be made in the structure of a protein or peptide and still obtain a molecule having like or otherwise desirable characteristics.

However, it is also well understood by skilled artisans that, inherent in the definition of a biologically functional equivalent protein or peptide, is the concept that there is a limit to the number of changes that may be made within a defined portion of the molecule and still result in a molecule with an acceptable level of equivalent biological activity and that key active site or structurally vital residues cannot be exchanged. Biologically functional equivalent peptides are therefore defined herein as those peptides in which certain, not most or all, of the amino acids may be substituted. In particular, where hexamer or heptamer peptides are concerned, it is contemplated that only about two, or more preferably, a single amino acid change would be made within a given peptide. Of course, a plurality of distinct peptides with different substitutions may easily be made and used in accordance with the invention.

In regard to changing a limited number of residues within a peptide, it is known that certain amino acids may be substituted for other amino acids without appreciable loss of function, as may be measured by the interactive binding capacity for structures such as receptors and cells, or the ability to compete with other molecules for binding to these sites. Since it is the interactive and competitive capacity of a protein or peptide that defines its biological functional activity, certain amino acid substitutions can be made in a peptide sequence (or, of course, its underlying DNA coding sequence) and nevertheless obtain a peptide with like, or even improved properties.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (glutamic acid) (−3.5); glutamine (−3.5); aspartate (aspartic acid) (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, as disclosed in U.S. Pat. No. 4,554,101, incorporated herein by reference. In U.S. Pat. No. 4,554,101, the following hydrophilicity values are assigned to amino acid residues: arginine (+3.0); lysine (+3.0); aspartate (aspartic acid) (+3.0±1); glutamate (glutamic acid) (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is well understood that an amino acid can be substituted for another having a similar hydrophilicity value and still obtain a biologically functional equivalent protein or peptide. In making changes based upon similar hydrophilicity values, the substitution of amino acids whose hydrophilicity values are within ±2 is preferred, those which are within ±1 are particularly preferred, and those within ±0.5 are even more particularly preferred.

Pharmaceutical Formulations

The peptides and compositions of the invention may be used for treating a variety of diseases and disorders in which CXC intercrines, such as IL-8, or neutrophils are involved or in which there is an inappropriate or increased inflammatory response. The invention is particularly suitable for the treatment of lung inflammation such as that connected with asthma, bronchitis, cystic fibrosis and ARDS. To treat disorders such as ARDS and cystic fibrosis, parenteral administration, such as intravenous, intramuscular or subcutaneous injection is contemplated to be the most preferred route, although one may also use aerosols or inhalants. Sprays, aerosols and inhalants, are only effective if the droplets are sufficiently fine and uniform in size so that the mist reaches the bronchioles. Particle size is of major importance in the administration of therapeutic agents via aerosols or inhalants. The optimum particle size for penetration into the pulmonary cavity is of the order of 0.5 to 7 μm. As fine mists are produced by pressurized aerosols, their use is considered advantageous. Such treatment strategies and therapeutic formulations are described in detail herein below in Example VIII.

As the invention may be employed to treat inflammation in various clinical settings, many types of pharmaceutical peptide formulations are contemplated. Therapeutic or pharmacological compositions of the present invention, whether for pulmonary or other treatments, will generally comprise an effective amount of a relatively small intercrine- or IL-8-inhibiting peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can also be incorporated into the therapeutic compositions of the present invention. For example, the intercrine-, IL-8- and neutrophil-inhibiting peptides may also be combined with other agents such as IL-8-derived N-terminal peptides, IFN-γ, oxygen radical scavengers and the like, to create peptide cocktails for treatment.

The preparation of pharmaceutical or pharmacological compositions containing an intercrine-, IL-8- and neutrophil-inhibiting peptide or peptides, including dextrorotatory peptides, as an active ingredients will be known to those of skill in the art in light of the present disclosure. If desired, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions and mouthwashes, and the inhalants and aerosols of Example VIII.

Solutions of the active peptides and compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for injection are contemplated to be useful in treating various diseases and may be administered into the blood stream or into the precise site of the inflammation. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A peptide or peptides can be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active peptide, peptides or agents to a small area.

The formulation of peptides for topical use, such as in creams, ointments and gels is also contemplated. The preparation of oleaginous or water-soluble ointment bases is also well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates. Even delivery through the skin may be employed if desired, e.g., by using transdermal patches, iontophoresis or electrotransport.

Buffered ophthalmic solutions also fall within the scope of the invention. These may be used in connection with patients suffering from disorders connected with increased retinal angiogenesis. The buffering is necessary due to pH changes the peptide may cause. Ophthalmic preparations may be created in accordance with conventional pharmaceutical practice, see for example "Remington's Pharmaceutical Sciences" 15th Edition, pages 1488 to 1501 (Mack Publishing Co., Easton, Pa.).

Suitable ophthalmic preparations will generally contain a novel dipeptide, peptide or agent as disclosed herein in a concentration from about 0.01 to about 1% by weight, and preferably from about 0.05 to about 0.5%, in a pharmaceutically acceptable solution, suspension or ointment. The ophthalmic preparation will preferably be in the form of a sterile buffered solution containing, if desired, additional ingredients, for example preservatives, buffers, tonicity agents, antioxidants and stabilizers, nonanoic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include dextrorotatory peptides; chemically designed or modified agents; and peptide and liposomal formulations in time release capsules to avoid peptidase and lipase degradation.

Oral formulations may include compounds in combination with an inert diluent or an assimilable edible carrier;

those enclosed in hard or soft shell gelatin capsules; those compressed into tablets; or those incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should generally contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Hexamer Peptide Inhibitors of IL-8

A series of studies was first carried out to determine whether hexamer peptides of the sequence RRWWCX (SEQ ID NO:23), where X may be any amino acid, would act as inhibitors of IL-8. The assays of the initial screen are based upon determining the ability of a given peptide to inhibit the binding of IL-8 to human neutrophils.

A. Preparation of Human Neutrophils

The use of human subjects for acquisition of neutrophils was approved by the Institutional Review Board for human experimentation. For the preparation of neutrophils, human blood was anticoagulated with heparin for enzyme release studies and with 0.33% sodium citrate for other studies. For chemotactic and enzyme release studies neutrophils were separated by dextran sedimentation and erythrocyte lysis by the method of Boyum (Kohler and Milstein, 1975). For binding studies and cytotoxic studies, the neutrophils were further purified in gradients of Percoll (Pharmacia Fine Chemicals, Piscataway, N.J.) to a purity of 90–93% (Kohler and Milstein, 1975).

B. IL-8 Binding Assays

Recombinant human IL-8 (72 amino acids; Pepro Tech Inc., Rocky Hill, N.J.) was radioactively labeled with $^{125}$I by the chloramine T method of Hunter and Greenwood (Hunter and Greenwood, 1962). Binding studies were performed according to Besemer et al. (1989), as follows: Neutrophils in phosphate buffered saline pH 7.4 (PBS) containing 0.1% bovine serum albumin (BSA) were incubated with labeled ligand in the presence or absence of the peptide being tested for 90 min at 4° C. to reach equilibrium and then centrifuged at 12,000×g for 3 min in Beckman B microfuge (Beckman Instruments, Fullerton, Calif.), through a cushion consisting of a mixture of paraffin oil (Fisher Scientific, Fair Lawn, N.J.) and silicon oil (Serva Co., N.Y., N.Y.). The pellet and supernatant were then counted in a gamma radiation spectrometer. The non-specific binding was estimated to measure the binding in the presence of 1 00-fold excess of nonlabeled ligand. The binding constants were calculated using the computer programs Lundon I and Lundon II.

C. Peptides

The RRWWCR-type peptides were synthesized by Houghten Pharmaceutical Company in San Diego using tBOC for protection of the α-amino group (Stewart and Young, 1969). All synthetic peptides were purified on high performance liquid chromatography (HPLC) using a preparative C18 reverse phase column (Waters Co., New Bedford, Mass.). Peptides were eluted using a gradient from 0.1% trifluoroacetic acid (TFA) to 80% acetonitrile in 0.1% TFA. The composition of the peptides was confirmed by amino acid analysis and sequencing.

D. Statistics

In this and all of the following examples, the data are expressed as the mean and the variation as the standard deviation (S.D.). Significance was determined by the Sheffés test when the variances were equal and the populations were normally distributed and only 2 groups were compared. Multiple comparisons were made using the analysis of variance and Sheffe's test.

E. Results

In these studies, a screening for inhibition was carried out at 100 μM concentration of the peptide being tested, with a $10^{-12}$M concentration of IL-8. In the first series of studies, twenty peptides were synthesized with the carboxyl-terminal residue of RRWWCX (SEQ ID NO:23) being changed to each of the standard protein amino acids in turn. In the first set of studies, several of the peptides totally inhibited IL-8 binding, as shown in Table 1A and Table 1B. The information presented in Table 1A and Table 1B is the same data, with Table 1A being listed in order of % inhibition and Table 1B being listed in order of SEQ ID NO, to enable straightforward comparisons. It can be clearly seen that all hexamer peptides other than RRWWCD (SEQ ID NO:26); RRWWCE (SEQ ID NO:27); RRWWCN (SEQ ID NO:35) and RRWWCQ (SEQ ID NO:37), have very significant inhibitory activity. It should also be noted that even though the preliminary data in Table 1 shows RRWWCN (SEQ ID NO:35) not to have inhibitory activity, subsequent studies showed this peptide did indeed exhibit certain inhibitory properties (FIG. 1).

TABLE 1A

| PEPTIDE | SEQ ID NO: | % INHIB. |
|---------|------------|----------|
| RRWWCR  | 1          | 112.2    |
| RRWWCK  | 32         | 110.3    |
| RRWWCT  | 39         | 88.4     |

TABLE 1A-continued

| PEPTIDE | SEQ ID NO: | % INHIB. |
|---|---|---|
| RRWWCP | 36 | 88.3 |
| RRWWCH | 30 | 87.9 |
| RRWWCL | 33 | 86.9 |
| RRWWCG | 29 | 86.8 |
| RRWWCV | 40 | 81.1 |
| RRWWCF | 28 | 80.2 |
| RRWWCS | 38 | 79.3 |
| RRWWCY | 42 | 77.9 |
| RRWWCC | 25 | 75.1 |
| RRWWCM | 34 | 69.0 |
| RRWWCW | 41 | 66.4 |
| RRWWCA | 24 | 51.9 |
| RRWWCI | 31 | 45.8 |
| RRWWCQ | 37 | 19.2 |
| RRWWCE | 27 | 17.1 |
| RRWWCD | 26 | 11.8 |
| RRWWCN | 35 | −12.0 |

TABLE 1B

| PEPTIDE | SEQ ID NO: | % INHIB. |
|---|---|---|
| RRWWCR | 1 | 112.2 |
| RRWWCA | 24 | 51.9 |
| RRWWCC | 25 | 75.1 |
| RRWWCD | 26 | 11.8 |
| RRWWCE | 27 | 17.1 |
| RRWWCF | 28 | 80.2 |
| RRWWCG | 29 | 86.8 |
| RRWWCH | 30 | 87.9 |
| RRWWCI | 31 | 45.8 |
| RRWWCK | 32 | 110.3 |
| RRWWCL | 33 | 86.9 |
| RRWWCM | 34 | 69.0 |
| RRWWCN | 35 | −12.0 |
| RRWWCP | 36 | 88.3 |
| RRWWCQ | 37 | 19.2 |
| RRWWCS | 38 | 79.3 |
| RRWWCT | 39 | 88.4 |
| RRWWCV | 40 | 81.1 |
| RRWWCW | 41 | 66.4 |
| RRWWCY | 42 | 77.9 |

As shown in Table 1A and Table 1B, several of the peptides totally inhibited IL-8 binding in the first studies. To assess relative effectiveness, the group was therefore re-evaluated with lower concentrations of the peptides. In these studies, Ac-RRWWCR-NH$_2$ (SEQ ID NO:1) was found to be the most potent inhibitor of binding of IL-8 to neutrophils (FIG. 1). The data presented in FIG. 1 shows RRWWCR (SEQ ID NO:1) to be significantly better than the other peptides under these conditions.

In another initial study, the acetylated derivative of RRWWCR (SEQ ID NO:1; Ac-RRWWCR-NH$_2$) emerged to be almost twice as effective as the non-acetylated peptide in inhibiting IL-8 binding to neutrophils.

EXAMPLE II

Kinetics of RRWWCR IL-8 Binding Inhibition

Figure 2:
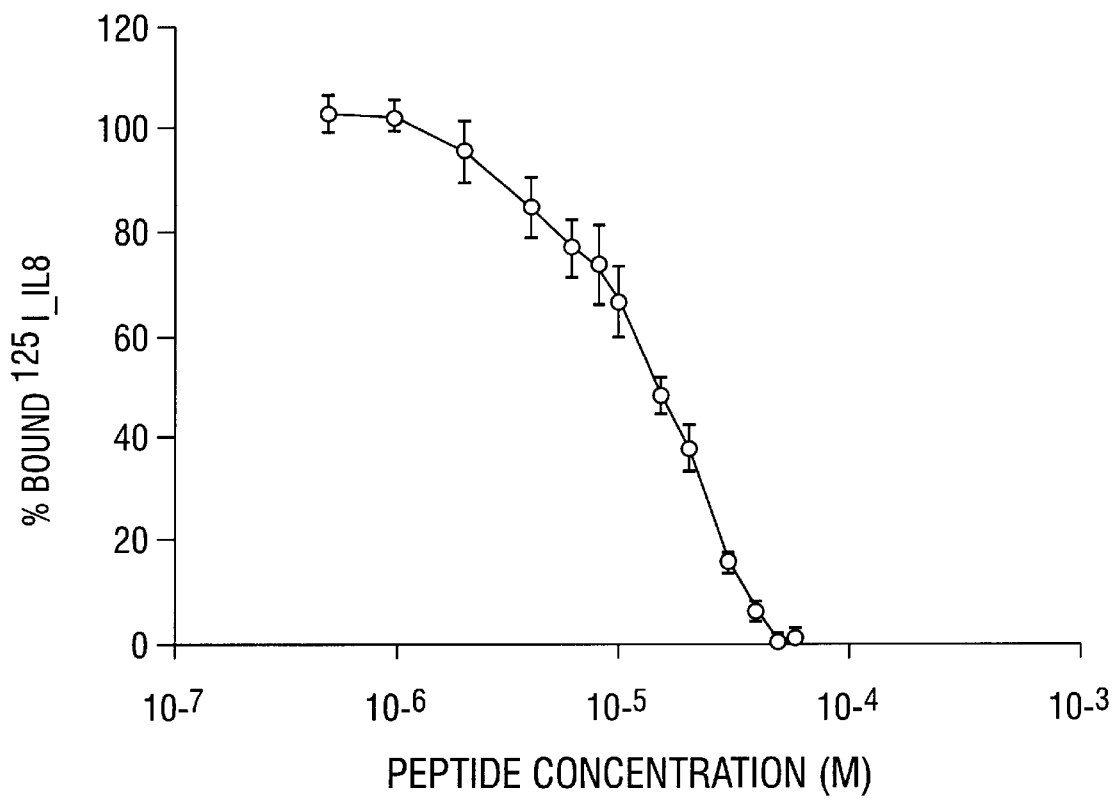
FIG. 2. IL-8 Binding Inhibition by Ac-RRWWCR-NH$_2$ (SEQ ID NO:1). Neutrophils (1×10$^6$) in 0.2 ml of PBS containing 0.1% BSA were incubated with 1 nM $^{125}$I-labeled IL-8 and increasing concentrations of Ac-RRWWCR-NH$_2$ (SEQ ID NO:1) for 90 min at 4° C. These data are representative of four studies.

In the studies described in this Example, the same methodology as that detailed in Example I was employed. An average EC$_{50}$ was determined from multiple replicates of the binding inhibition curve to be 13.7±0.6 µM (a representative curve from these assays is shown in FIG. 2). If the mechanism of inhibition were purely competitive with a single site model, the estimated K$_I$ was approximately 10 µM. However, the mechanism was more complicated. A steeper binding inhibition curve than usual single site model as well as high Hill coefficient value (1.5–1.7) suggested the presence of positive cooperativity. The curve did not fit either one-, two- or three-site model well when it was analyzed using the Lundon II computer program, although IL-8 is known to react with at least two distinct receptors on neutrophils. Therefore, it was difficult to estimate individual K, values for each class of receptor.

Figure 3A:
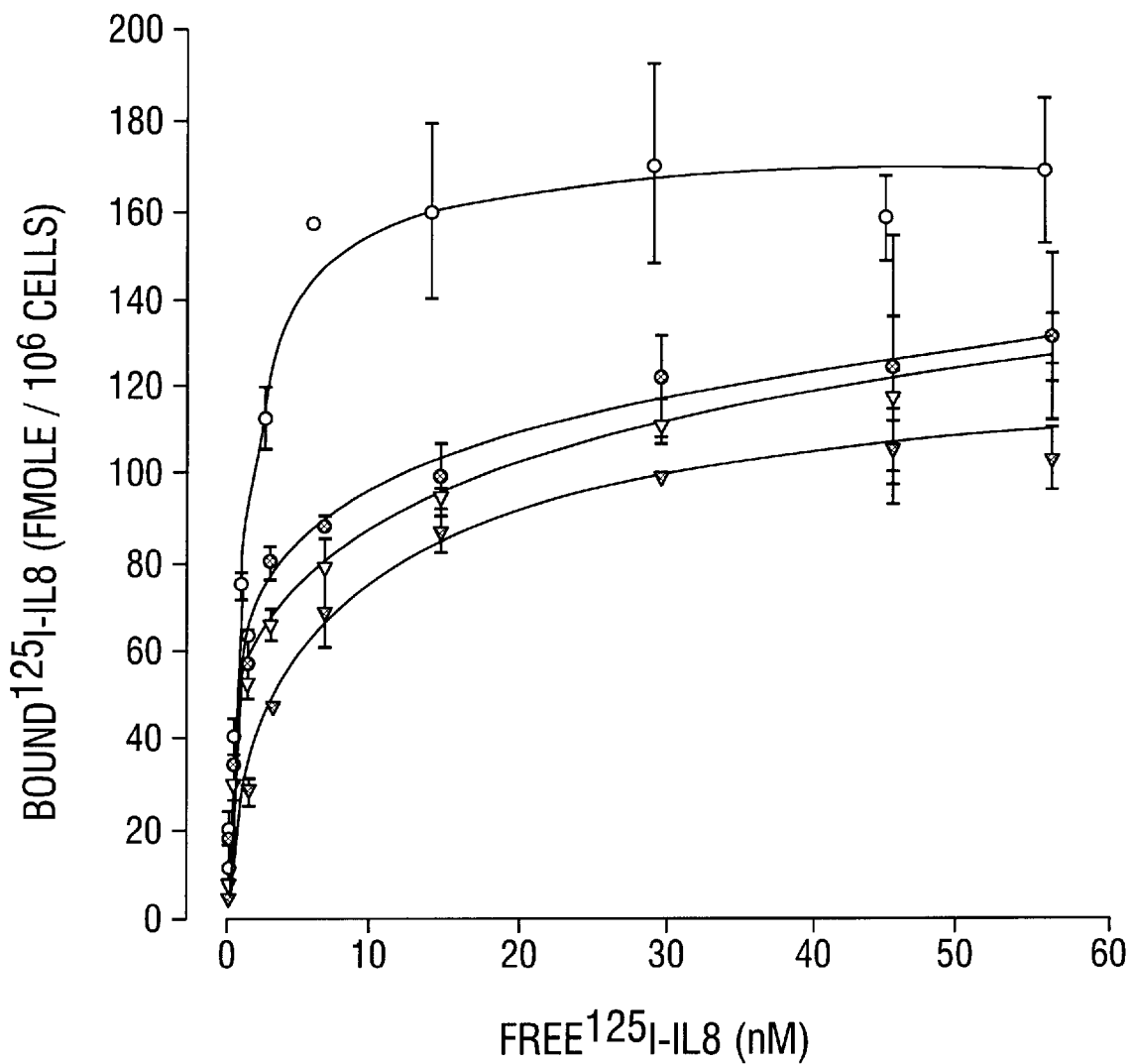
FIG. 3A. Saturation Studies in the Presence of Ac-RRWWCR-NH$_2$ (SEQ ID NO:1), Binding Isotherms with Best Fit Curve Calculated Using Lundon I. Binding assays were performed in the absence of the peptide (○) and in the presence of 10 μM (●), 20 μM (_), or 40 μM (▼) peptide with increasing concentrations of $^{125}$I-labeled IL-8. Each data point represent specific binding which was computed by subtracting nonspecific binding in the presence of excess unlabeled IL-8 from total binding.
Figure 3B:
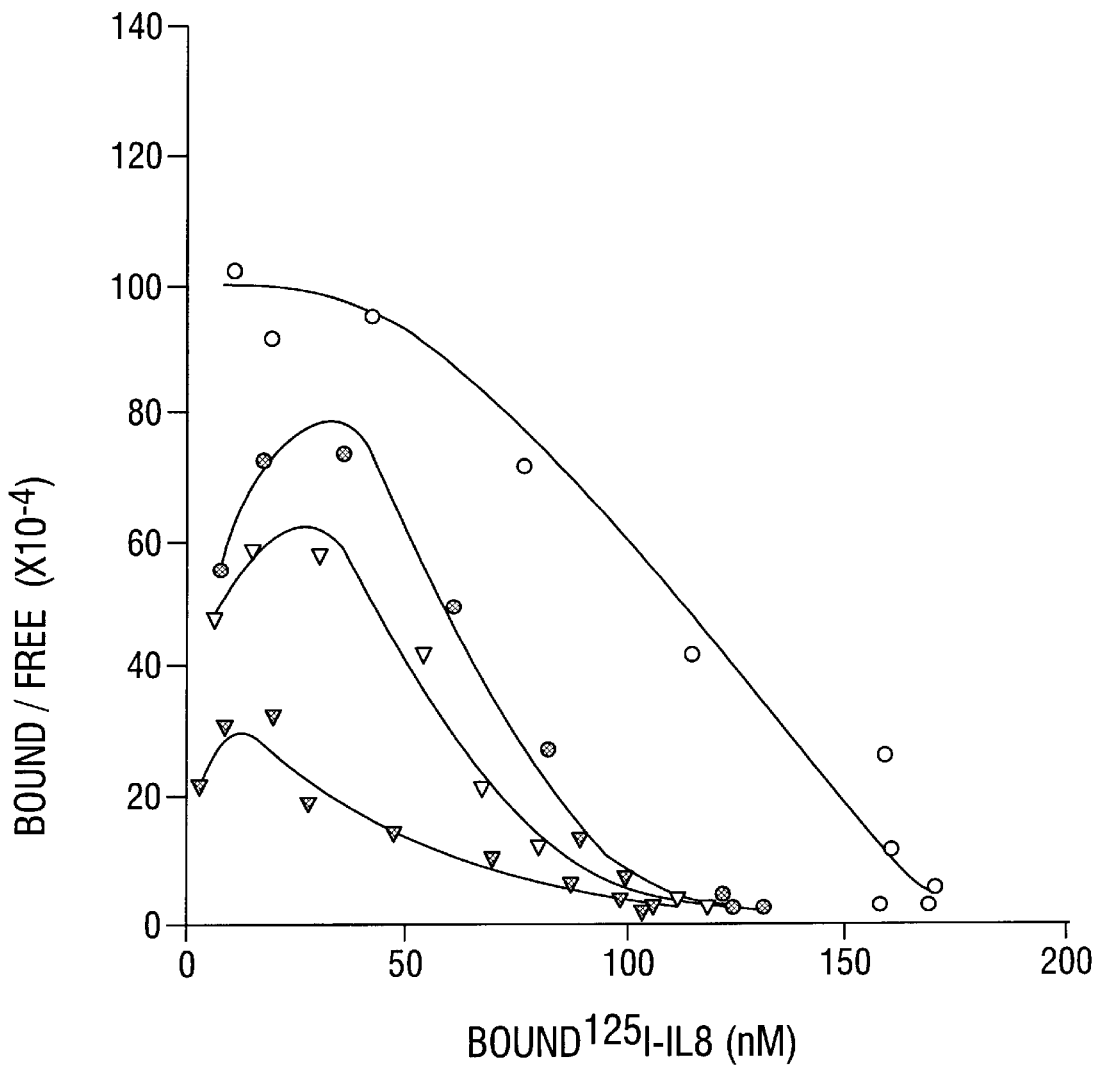
FIG. 3B. Saturation Studies in the Presence of Ac-RRWWCR-NH$_2$ (SEQ ID NO:1), Scatchard Plots. Binding assays were performed in the absence of the peptide (○) and in the presence of 10 μM (●), 20 μM (_), or 40 μM (▼) peptide with increasing concentrations of $^{125}$I-labeled IL-8.

The kinetics of IL-8 binding inhibition by RRWWCR (SEQ ID NO:1) were determined. IL-8 binding isotherms in the absence of Ac-RRWWCR-NH$_2$ and in the presence of three concentrations of the peptide are shown in FIG. 3A. The Scatchard plot in the absence of the peptide failed to show the IL-8 binding to two distinct receptors (FIG. 3B). The plots in the presence of Ac-RRWWCR-NH$_2$ (SEQ ID NO:1) were non-linear and were compatible with a two site model when they were analyzed using the Lundon I computer program. The estimated changes in Kd and Bmax are shown in Table 2. The data indicate that one group of IL-8 receptors decreased its affinity at 10 µM of the peptide and the other group decreased Bmax with increasing concentrations of the peptide.

Figure 4:
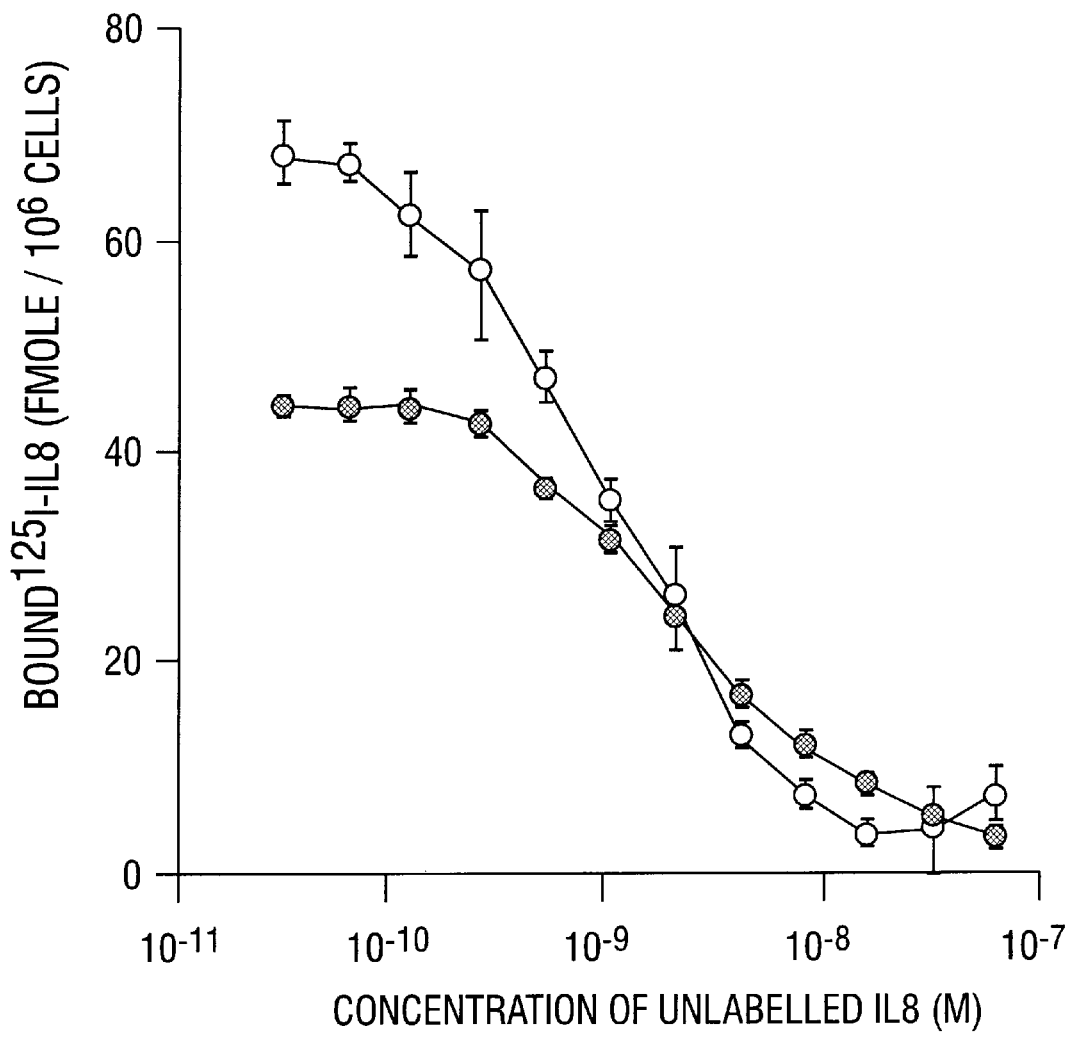
FIG. 4. Binding Inhibition Studies in the Presence of Ac-RRWWCR-NH$_2$ (SEQ ID NO:1). Neutrophils were incubated with 1 nM of $^{125}$I-labeled IL-8 and increasing concentration of unlabeled IL-8 in the presence (●) or the absence (○) of 10 μM Ac-RRWWCR-NH$_2$ (SEQ ID NO:1).

For further characterization of binding kinetics, a binding inhibition assay using non-labeled IL-8 in the presence of 10 µM Ac-RRWWCR (SEQ ID NO:1) was performed (FIG. 4). Both the binding inhibition curves in the presence and absence of Ac-RRWWCR (SEQ ID NO:1) were analyzed using Lundon II and shown to best fit a two-site model. There was no evidence for appearance of a low affinity state of the receptors. Estimated changes in Kd and Bmax indicate that only the high affinity sites decreased both their affinity and Bmax in the presence of 10 µM peptide (Table 3).

TABLE 2

Estimated values of binding parameters computed from binding isotherms using Lundon I

|  |  | 0 µM* | 10 µM⁺ | 20 µM⁺ | 40 µM⁺ |
|---|---|---|---|---|---|
| one-site model |  |  |  |  |  |
| Bmax | (fmole/10$^6$ cells) | 174.2 ± 4.5 |  |  |  |
| Kd | (nM) | 1.3 ± 0.2 |  |  |  |
| two-site model |  |  |  |  |  |
| Receptor 1 |  |  |  |  |  |
| Bmax | (fmole/10$^6$ cells) |  | 91.9 ± 9.2 | 90.9 ± 27.3 | 82.0 ± 25.4 |
| Kd | (nM) |  | 68.0 ± 93.7 | 42.8 ± 42.2 | 13.0 ± 83.6 |

TABLE 2-continued

Estimated values of binding parameters computed from binding isotherms using Lundon I

|  |  | 0 μM* | 10 μM+ | 20 μM+ | 40 μM+ |
|---|---|---|---|---|---|
| Receptor 2 |  |  |  |  |  |
| Bmax | (fmole/10⁶ cells) |  | 90.9 ± 9.7 | 76.2 ± 11.8 | 44.2 ± 30.0 |
| Kd | (nM) |  | 0.7 ± 0.2 | 0.8 ± 0.3 | 1.3 ± 1.1 |

*binding isotherm best fitted a one-site model.
+binding isotherm best fitted a two-site model.

TABLE 3

Estimated Values of Binding Parameters Computed from Binding Inhibition Curves Using Lundon II

|  |  | IL-8 alone | +10 μM Ac-RRWWCR |
|---|---|---|---|
| Receptor 1 |  |  |  |
| Bmax | (fmole/10⁶ cells) | 38.8 ± 0.6 | 11.2 ± 0.8 |
| Kd | (nM) | 0.03 ± 0.00 | 1.23 ± 0.39 |
| Receptor 2 |  |  |  |
| Bmax | (fmole/10⁶ cells) | 68.8 ± 0.7 | 75.6 ± 0.7 |
| Kd | (nM) | 0.67 ± 0.04 | 0.76 ± 0.03 |

EXAMPLE III

Specificity of RRWWCR To IL-8 Binding Inhibition

To examine the specificity of Ac-RRWWCR-NH$_2$ (SEQ ID NO:1) on ligand-receptor binding, the inventors tested whether the peptide reduced the binding of human $^{125}$I-C5a or $^3$H-leukotriene B$_4$ to human neutrophils.

Recombinant human fifth component of complement (C5a) (Sigma Chemical Co., St. Louis, Mo.) was radioiodinated enzymatically using Enzymobead (Bio Rad, Richmond, Calif.). Tritiated leukotriene B$_4$ was purchased from Du Pont Co., Wilmington, Del. Binding assays for C5a and leukotriene B$_4$ were performed as described for IL-8 binding in Example I, except that the buffers used were PBS containing 1 mM CaCl$_2$, 0.5 mM MgCl$_2$, 0.5% BSA, and HBSS containing 0.1% ovulabumin and 10 mM HEPES (pH7.3), respectively, as previously described (Braunwalder et al., 1992; Sherman et al., 1988). The radioactivity was measured with liquid scintillation counter for the leukotriene B$_4$ assay. The binding of both ligands were saturable and inhibited by the non-labeled agonists in dose dependent manners.

Figure 5:
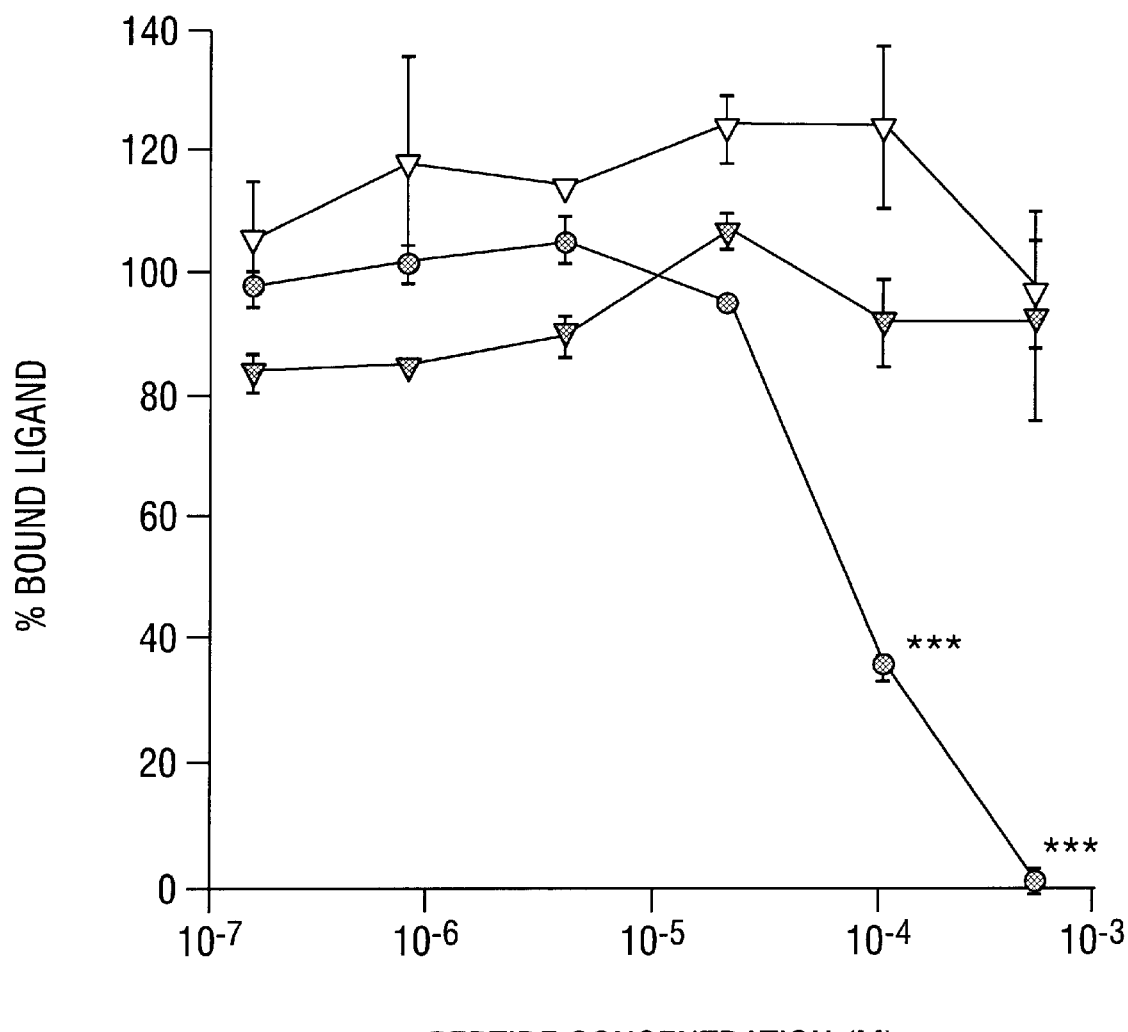
FIG. 5. Effect of Ac-RRWWCR-NH$_2$ (SEQ ID NO:1) on Binding of IL-8, C5a, and Leukotriene B$_4$ to Neutrophils. The bindings assays were performed with 1 nM $^{125}$I-labeled IL8 (●), 0.25 nM $^{125}$I-labeled C5a (▽), or 0.4 nM $^3$H-labeled leukotriene B$_4$ (▼) and increased concentration of Ac-RRWWCR-NH$_2$ (SEQ ID NO:1). Analysis of variance was used for multiple comparison. When there was significant difference, the differences between binding without the peptide and those with peptide were tested using Sheffés test; ***,p<0.001.

In these studies it was found that at 100 μM Ac-RRWWCR-NH$_2$ (SEQ ID NO:1) did not affect the binding of C5a nor leukotriene B$_4$, but that it suppressed the IL-8 binding significantly at a concentration of 100 nM (FIG. 5).

EXAMPLE IV

Cytotoxicity of RRWWCR To Neutrophils

The inventors next examined the cytotoxic capacity of Ac-RRWWCR-NH$_2$ (SEQ ID NO:1). This was achieved by measuring the amount of $^{51}$Cr released from neutrophils, as follows: The neutrophil preparation (2×10$^7$/ml) in RPMI-1640 media containing 10% donor's plasma was incubated with 500 μCi of Na$_2$$^{51}$CrO$_4$ (Du Pont Co.) for 60 min at 37° C. The cells were washed 3 times, resuspended in the media at the concentration of 1×10$^7$/ml, and then incubated for 30 min at 37° C. to allow spontaneous lysis of marginally viable cells. After washing twice, a 100 μl aliquot of the $^{51}$Cr-labeled neutrophils (5×10$^6$/ml) was mixed with 100 μl of Ac-RRWWCR-NH$_2$ (SEQ ID NO:1) in a siliconized microcentrifuge tube. The buffer and the conditions of incubation simulated either the binding assay or the chemotactic assay. After the incubation, the tubes were centrifuged at 300×g for 7 min at 4° C. and the radioactivity in the supernatant was then counted in a gamma radiation spectrometer. Triplicate tubes containing buffer alone or 2% SDS were used to determine spontaneous and maximum release, respectively. The percentage lysis was calculated by using the following formula:

$$\% \text{LYSIS} = \frac{(\text{EXPERIMENTAL CPM} - \text{SPONTANEOUS CPM}) \times 100}{(\text{MAXIMUM CPM} - \text{SPONTANEOUS CPM})}$$

Figure 6:
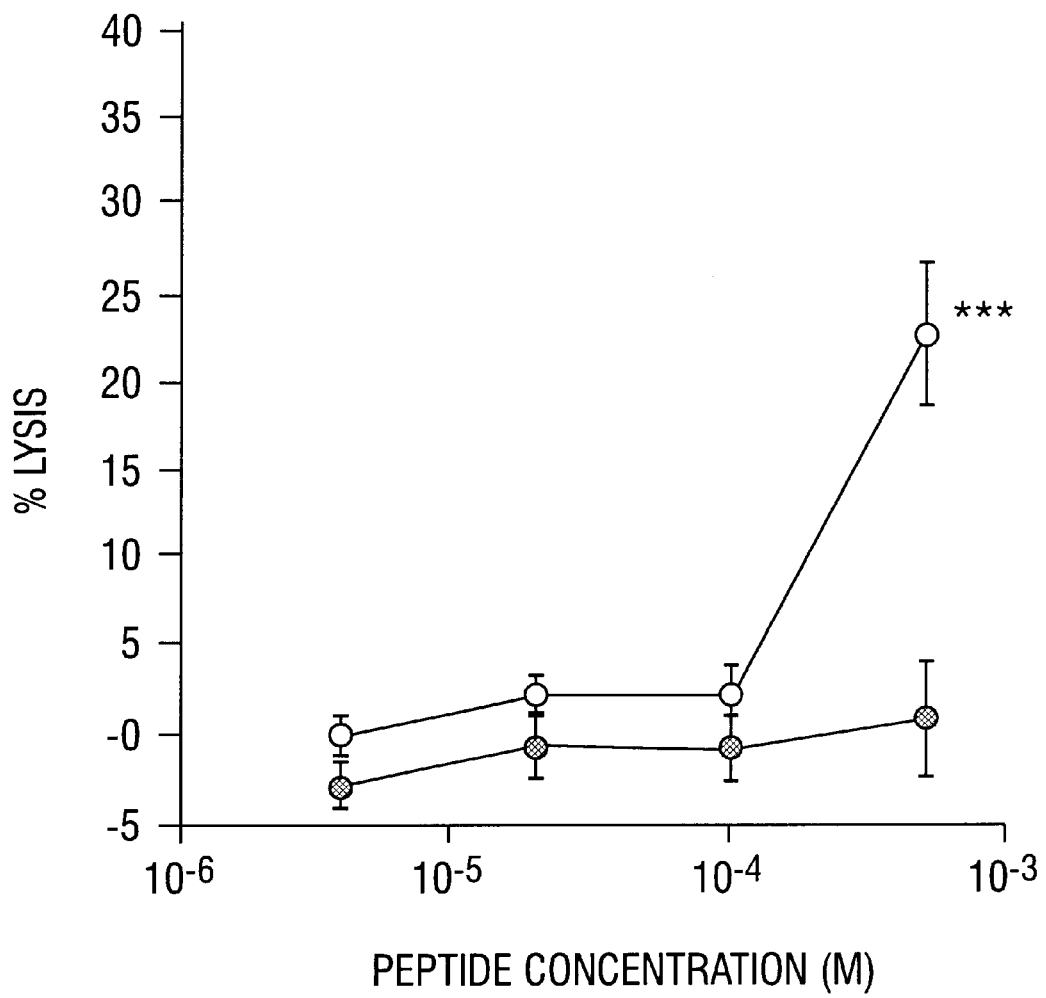
FIG. 6. Cytotoxicity Test. Chromium-labeled neutrophils were incubated with increasing concentrations of Ac-RRWWCR-NH$_2$ (SEQ ID NO:1) in PBS containing 0.1% BSA for 90 min at 4° C. (●) or in RPMI-1640 media containing 1% BSA for 30 min at 37° C. (○). Analysis of variance was used for multiple comparison. When there was significant difference, the differences between % lysis without the peptide and those with peptide were tested using Sheffés test; ***,p<0.001.

When chromium-labeled cells were incubated in PBS containing 0.1% BSA for 90 min at 4° C., it was found that the percentage of cells lysed remained near control level up to 500 μM of the peptide (FIG. 6). Under conditions used in chemotaxis, 100 μM of the peptide had no effect, however, 500 μM peptide damaged almost 25% of the cells.

EXAMPLE V

Effect of RRWWCR on Neutrophil Functions

The effect of RRWWCR on neutrophil chemotaxis and enzyme release was next examined.

A. Chemotaxis

Chemotaxis was performed using the leading front method as described by Zigmond and Hirsh (1973). IL-8 or controls were placed in the lower well of a Boyden chamber. A five micron pore size, 100 μm thick cellulose nitrate filter (Sartorius Filter, Inc., San Francisco, Calif.) was placed on the surface and the chamber was then assembled. A 200 μl aliquot of the neutrophil preparation (1×10$^6$ cells/ml) in RPMI-1640 media containing 1% BSA was added to the top of the filter and incubated at 37° C. for 30 min. The filter was then fixed, stained and mounted on a glass microscope slide. The leading front was determined by the position of the leading two cells. The distance that the leading two cells had moved through the filter was measured for six fields on each filter. The measurements were made with four filters for each set of conditions.

B. Neutrophil Enzyme Release

Neutrophil enzyme release was studied by a modification of the method of Goldstein and colleagues (Goldstein et al., 1973). Cytochalasin B (Sigma Chemical Co.) was stored in dimethyl sulfoxide at a concentration of 5 mg/ml and was diluted to a concentration of 50 μg/ml in Hank's Balanced Salt Solution (HBSS) immediately before use. Cytochalasin B, 200 μl, was added to 1 ml of suspension of neutrophils, 6.25×10$^6$ cells/ml in HBSS, to achieve a final cytochalasin B concentration of 10 μg/ml. The solution was then incubated in 96 well plates at room temperature for 10 min. The stimulant, 100 μl, was added, and this cell suspension was incubated for 30 min at 37° C. The plates were centrifuged and 100 μl of supernatant was removed. Aliquots of 40 μl of supernatant were mixed with 10 μl of 0.01M phenolphthalein-glucuronic acid (Sigma Chemical Co.) and 40 μl of 0.1M sodium phosphate pH 4.6 in 96-well plates for β-glucuronidase measurement. After 16 hr incubation at 37° C., 200 μl of 0.2M Glycine in 0.2M NaCl, pH10.4 was added to each well and ODS$_{40}$ was measured as the enzyme activity.

C. Results

It was found that the Ac-RRWWCR-NH$_2$ (SEQ ID NO:1) had no effect on neutrophil chemotaxis or enzyme release. A checkerboard analysis of cell movement indicated that it was not chemotactic for neutrophils (Table 4). In control studies shown in FIG. 7 and FIG. 8, the peptide had no effect on chemokinesis of neutrophils and did not stimulate β-glucuronidase release from the cells.

Figure 7:
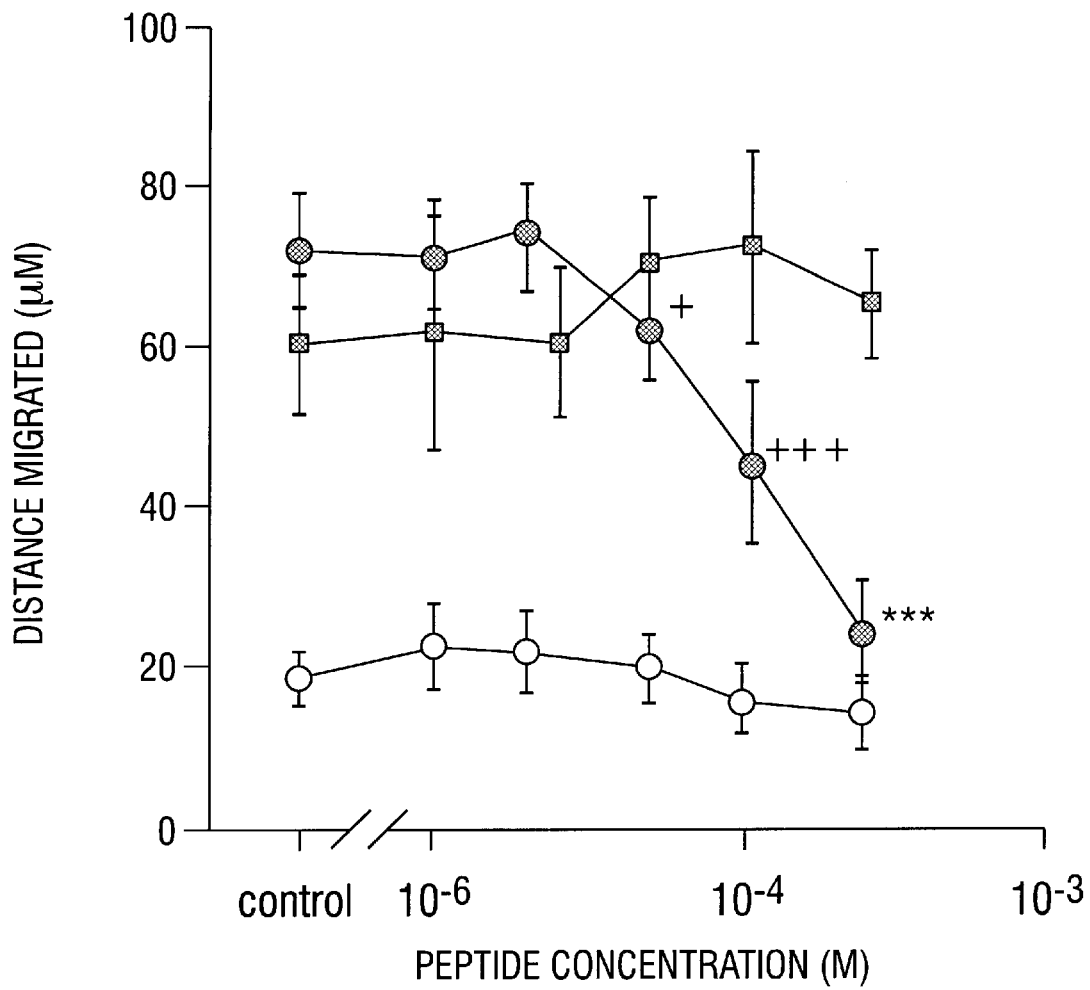
FIG. 7. The Effect of Ac-RRWWCR-NH$_2$ (SEQ ID NO:1) on Neutrophil Chemotaxis. Chemotaxis was performed in the presence of increasing concentration of Ac-RRWWCR-NH$_2$ (SEQ ID NO:1) in both upper and lower chamber. Stimulants added to lower chamber were 10 nM IL-8 (●), 10 nM fMLP (■), or media alone (○) as control. Analysis of variance was used for multiple comparison. When there was significant difference, the differences between distance migrated without the peptide and those with peptide were tested using Sheffés test; *,0.01<p<0.05, ***,p<0.001.
Figure 8:
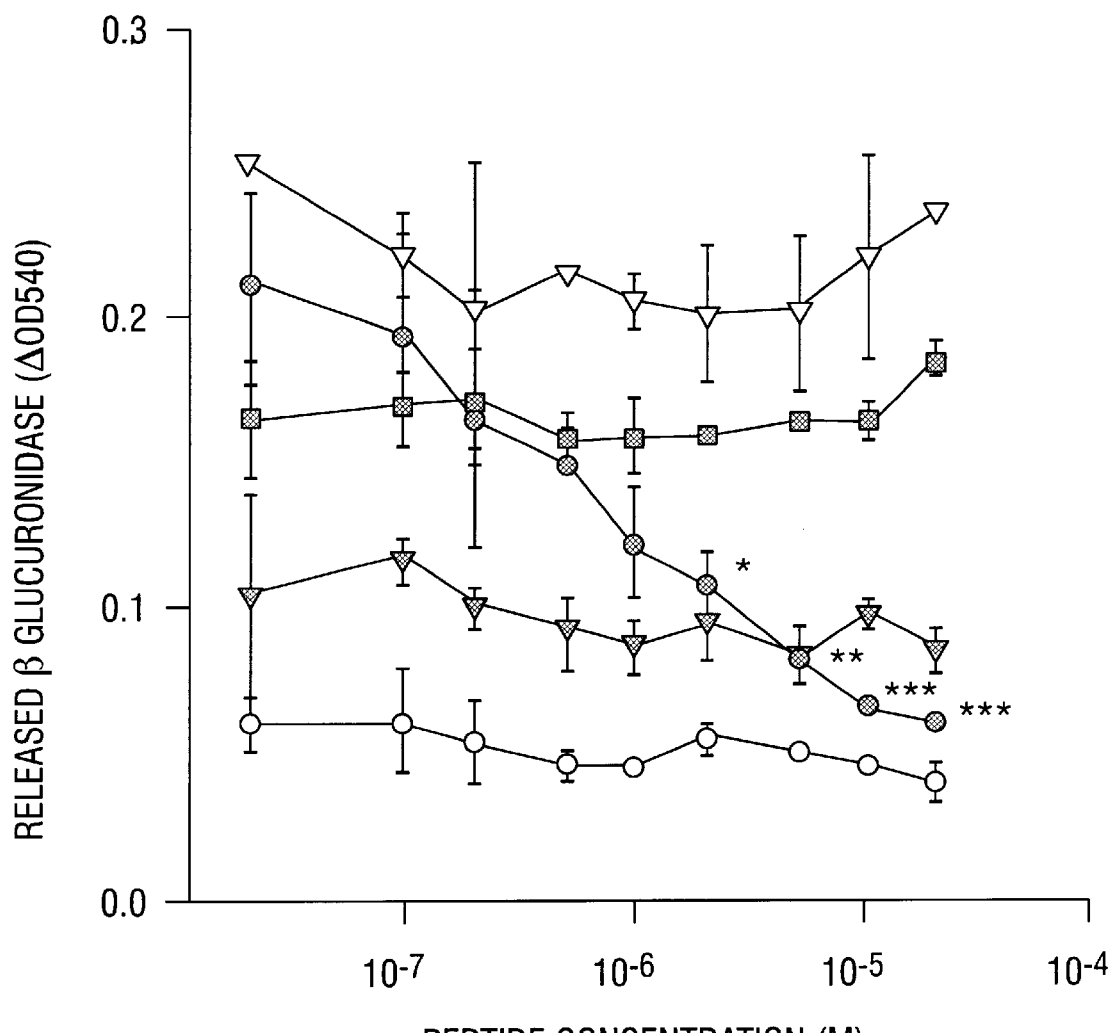
FIG. 8. The Effect of Ac-RRWWCR-NH$_2$ (SEQ ID NO:1) on β-glucuronidase Release. Neutrophils pretreated with cytochalasin B were incubated with 100 nM IL-8 (●), 100 nM fMLP (■), 100 nM C5a (_) or 100 nM leukotriene B4 (▼) or without any stimulant (○) in the presence of increasing concentration of Ac-RRWWCR-NH$_2$ (SEQ ID NO:1) for 30 min at 37° C. β-glucuronidase activity of supernatants were measured using phenolphthalein-glucuronic acid as substrate. Analysis of variance was used for multiple comparison. When there was significant difference, the differences between distance migrated without the peptide and those with peptide were tested using Sheffés test; *,p<0.05, ,p<0.01, *,p<0.001.

To confirm that the inhibition of IL-8 binding by Ac-RRWWCR-NH$_2$ is related to suppression of neutrophil activation by IL-8, the inventors examined the effects of the peptide on chemotaxis and β-glucuronidase release. Ac-RRWWCR-NH$_2$ (SEQ ID NO:1) significantly inhibited chemotaxis of neutrophils stimulated with 10 nM of IL-8 at a concentration of Ac-RRWWCR-NH$_2$ (SEQ ID NO:1) of 50 μM, whereas it had no effect on chemotaxis induced by formyl-L-Methionyl-L-Leucyl-L-Phenylalanine (fMLP) (FIG. 7). Ac-RRWWCR-NH$_2$ (SEQ ID NO:1) inhibited β-glucuronidase release stimulated by 100 nM of IL-8 at 2 μM, a lower concentration than required for inhibition of chemotaxis, however, it did not affect the enzyme release stimulated by fMLP, C5a or leukotriene B$_4$ (FIG. 8).

seventh amino acid. In the heptamer studies, twenty peptides were synthesized with the carboxyl-terminal residue of RRWWCRX (SEQ ID NO:2) being changed to each of the standard protein amino acids in turn. In the first set of heptamer studies, several of the peptides exhibited very strong inhibition of IL-8 binding, as shown in Table 5A and Table 5B. The information presented in Table 5A and Table 5B is the same data, with Table 5A being listed in order of % inhibition and Table 5B being listed in order of SEQ ID NO, to enable straightforward comparisons. It can be clearly seen that all heptamer peptides (SEQ ID NOs:3 through 22) have significant inhibitory activity under these conditions (Table 5A).

TABLE 5A

| PEPTIDE | SEQ ID NO: | % INHIB. |
| --- | --- | --- |
| RRWWCR | 1 | 112.2 |
| rrwwcrk | 11 | 113.1 |
| rrwwcrn | 14 | 110.8 |
| rrwwcrg | 8 | 108.0 |
| rrwwcrc | 4 | 107.7 |
| rrwwcrd | 5 | 107.0 |
| rrwwcrh | 9 | 107.0 |
| rrwwcrw | 21 | 106.3 |
| rrwwcrf | 7 | 105.6 |
| rrwwcrr | 17 | 102.8 |
| rrwwcre | 6 | 99.1 |
| rrwwcrl | 12 | 99.1 |
| rrwwcrm | 13 | 96.2 |
| rrwwcra | 3 | 95.3 |
| rrwwcri | 10 | 93.9 |
| rrwwcrq | 16 | 89.2 |
| rrwwcrv | 20 | 89.2 |
| rrwwcrp | 15 | 87.3 |
| rrwwcry | 22 | 85.4 |
| rrwwcrs | 18 | 70.4 |
| rrwwcrt | 19 | 56.3 |

TABLE 4

Checkerboard analysis for chemotactic activity of Ac-RRWWCR-NH$_2$ (SEQ ID NO: 1)

| peptide below filter (μM) | peptide above filter (μM) | | | | |
| --- | --- | --- | --- | --- | --- |
| | 0.0 | 1.0 | 5.0 | 12.5 | 25.0 |
| 0.0 | 26.7 ± 4.5 | | | | |
| 1.0 | | 27.8 ± 5.5 | 28.0 ± 4.7(29.1) | 25.6 ± 4.0(24.2) | 26.7 ± 6.3(24.3) |
| 5.0 | | 29.6 ± 6.3(28.0) | 29.3 ± 7.2 | 24.2 ± 5.4(23.7) | 25.9 ± 6.7(24.4) |
| 12.5 | | 27.0 ± 5.5(28.4) | 27.5 ± 4.8(28.5) | 22.9 ± 5.9 | 24.8 ± 5.8(24.5) |
| 25.0 | | 30.9 ± 4.7(28.4) | 27.5 ± 4.9(27.1) | 27.9 ± 4.8(23.1) | 24.7 ± 3.8 |

Figures without parentheses represent mean ± SD of the experimental observations in 20 different fields on 4 filters. Figures inside parentheses represent a calculation of migration expected if the cells were responding to the absolute concentration and not to the gradient.

EXAMPLE VI

Additional Peptide Inhibitors of IL-8

Further series of studies were carried out to determine whether other peptides related to Ac-RRWWCR-NH$_2$ (SEQ ID NO:1) would act as inhibitors of IL-8, and to determine their relative effectiveness. In the studies described in this Example, the same methodology as that detailed in Example I was employed.

A. Heptamer Peptides

In this series of studies, the inventors examined D-amino acid analogues of RRWWCR (SEQ ID NO:1) with an added

TABLE 5B

| PEPTIDE | SEQ ID NO: | % INHIB. |
| --- | --- | --- |
| RRWWCR | 1 | 112.2 |
| rrwwcra | 3 | 95.3 |
| rrwwcrc | 4 | 107.7 |
| rrwwcrd | 5 | 107.0 |
| rrwwcre | 6 | 99.1 |
| rrwwcrf | 7 | 105.6 |
| rrwwcrg | 8 | 108.0 |

TABLE 5B-continued

| PEPTIDE | SEQ ID NO: | % INHIB. |
|---|---|---|
| rrwwcrh | 9 | 107.0 |
| rrwwcri | 10 | 93.9 |
| rrwwcrk | 11 | 113.1 |
| rrwwcrl | 12 | 99.1 |
| rrwwcrm | 13 | 96.2 |
| rrwwcrn | 14 | 110.8 |
| rrwwcrp | 15 | 87.3 |
| rrwwcrq | 16 | 89.2 |
| rrwwcrr | 17 | 102.8 |
| rrwwcrs | 18 | 70.4 |
| rrwwcrt | 19 | 56.3 |
| rrwwcrv | 20 | 89.2 |
| rrwwcrw | 21 | 106.3 |
| rrwwcry | 22 | 85.4 |

Figure 9:
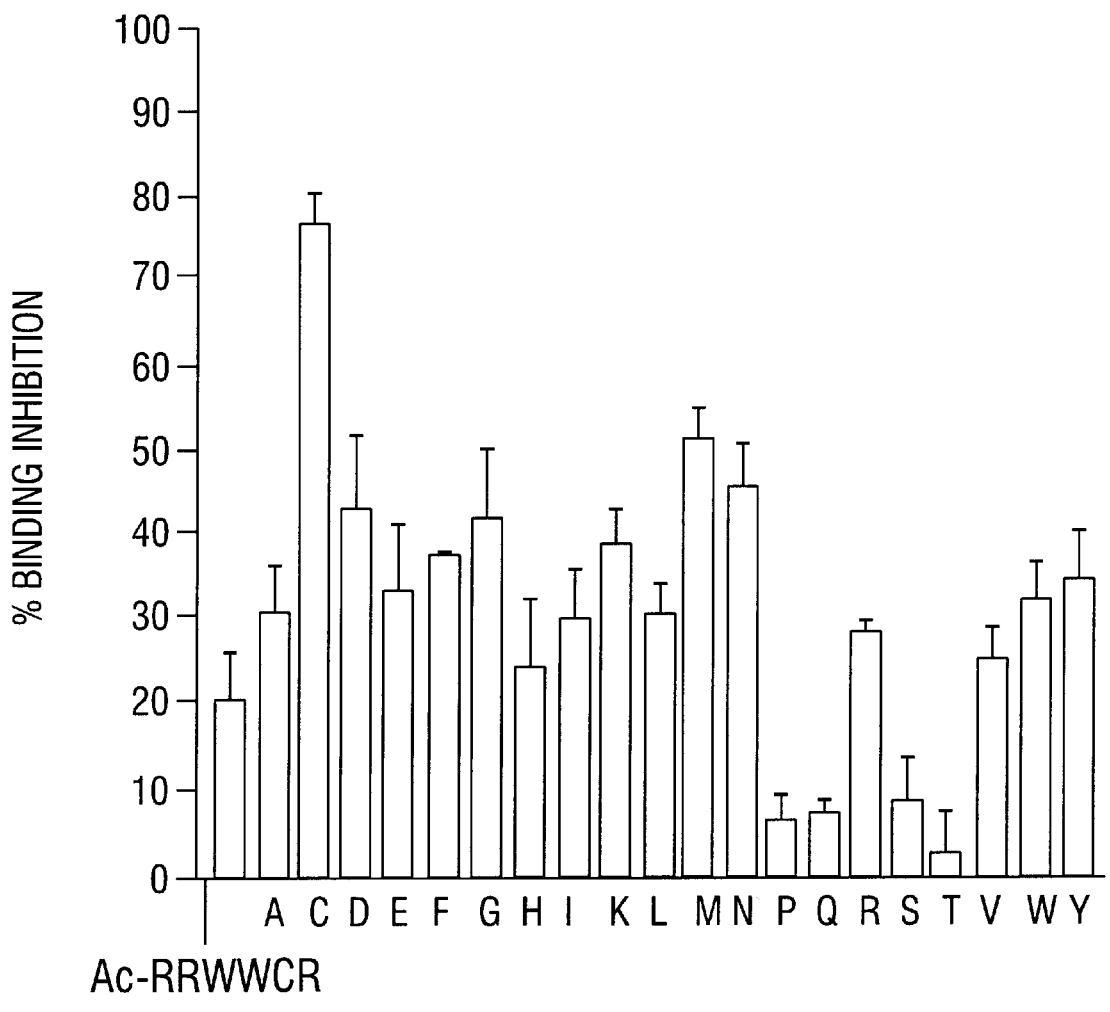
FIG. 9. Binding Inhibition by All D-amino Acid Ac-rrwwcrx-NH$_2$ (SEQ ID NO:2) Series. Ac-RRWWCR (SEQ ID NO:1) was synthesized using D-amino acids and added each of the 20 standard protein D-amino acids were added at the seventh position (SEQ ID NO:3 through 22). The notation on the x axis indicates the residue at the carboxyterminal position. The binding study was performed using 10 μM of each peptide. Ac-RRWWCR-NH$_2$ (SEQ ID NO:1) made with L-amino acids was used as a control.

In order to determine the relative effectiveness of the heptamers, their inhibitory effects were determined at lower concentrations. The peptide with D-cysteine present at the carboxyl-terminal end (RRWWCRC; SEQ ID NO:4) was found to be almost 56% more effective than the next best peptide in this group and to be more effective than Ac-RRWWCR-NH$_2$ (SEQ ID NO:1; FIG. 9). Ac-rrwwcrc-NH$_2$ (SEQ ID NO:4) prevented 80% of the binding of IL-8 to neutrophils as compared to 20% inhibition by the L-amino acid peptide Ac-RRWWCR-NH$_2$ (SEQ ID NO:1) at 10 μM.

B. Other Peptides

The inventors also tested several additional peptides which were either related to the amino terminal portion of IL-8 or were found in other proteins and had five of the six residues in RRWWCR (SEQ ID NO:1). The peptides ELRCQCIKTY, ELRSQSIKTY, ELRMQMIKTY, QIPRRSWCRFLF, and GWRRWWCDAVLY (SEQ ID NOs:49 through 53, respectively) were synthesized at The University of Texas Health Center at Tyler utilizing an 431 Peptide Synthesizer (Applied Biosystems, Foster City, Calif.), using the 9-fluorenylmethoxycarbonyl (fMOC) group to protect the α-amino group as described by Meienhofer and coworkers (Meienhofer et al., 1979) and Arshady et al. (1979). All synthetic peptides were purified on high performance liquid chromatography (HPLC) using a preparative C18 reverse phase column (Waters Co., New Bedford, Mass.). Peptides were eluted using a gradient from 0.1% trifluoroacetic acid (TFA) to 80% acetonitrile in 0.1% TFA. The composition of the peptides was confirmed by amino acid analysis and sequencing by the Protein Core facility at UTHC.

In this series of studies, only Ac-RRWWCR-NH$_2$ (SEQ ID NO:1) and QIPRRSWCRFLF (SEQ ID NO:52) inhibited binding of IL-8 to neutrophils (Table 6).

TABLE 6

Inhibition of IL-8 Binding to Neutrophils by Synthetic Peptides

| Peptide Tested | SEQ ID NO: | % Binding Inhibition |
|---|---|---|
| Ac-KELRCQ | 54 | −0.4 ± 11.8 |
| QIPRRSWCRFLF | 52 | 61.5 ± 1.0 |
| GWRRWWCDAVLY | 53 | −12.9 ± 2.9 |
| ELRCQCIKTY | 49 | 7.6 ± 2.1 |
| ELRSQSIKTY | 50 | 5.8 ± 3.9 |
| ELRMQMIKTY | 51 | −6.9 ± 3.0 |
| Ac-RRWWCR | 1 | 98.6 ± 0.9 |
| RXXXXX | 43 | 11.5 |
| XXXXXR | 44 | 5.8 |
| XRXXXX | 45 | 9.9 |

TABLE 6-continued

Inhibition of IL-8 Binding to Neutrophils by Synthetic Peptides

| Peptide Tested | SEQ ID NO: | % Binding Inhibition |
|---|---|---|
| XXWXXX | 46 | 1.4 |
| XXXWXX | 47 | 18.5 |
| XXXXCX | 48 | 7.1 |

EXAMPLE VII

Inhibition of GRO and MIP2B Neutrophil Binding

Ac-RRWWCX-NH$_2$ (SEQ ID NO:23) was also examined for the ability to inhibit other CXC intercrines. The present example demonstrates that, in addition to IL-8 inhibition, Ac-RRWWCX-NH$_2$ (SEQ ID NO:23) effectively inhibits GRO and MIP2β binding to human neutrophils.

MIP2β and GRO/MGSA were radioiodinated using Bolten Hunter reagent. The radioiodinated components were mixed with various concentration of the Ac-RRWWCX-NH$_2$ (SEQ ID NO:23) peptide and incubated at room temperature for 15 min. Neutrophil suspension (1×10$^6$ cells in 160 μl PBS containing 0.1% BSA) was added to 40 μl of the mixture and incubated for 90 min on ice. The radioactivity bound to the cells was separated from free radioactivity by centrifugation through an oil layer. The bound radioactivity is an indication of bound CXC intercrine peptide. The % binding inhibition in the presence of Ac-RRWWCX-NH$_2$ (SEQ ID NO:23) was calculated as follows:

$$\% \text{ binding inhibition} = 1 - \frac{B - NSP}{T - NSP} \times 100$$

where B is bound radioactivity in the presence of the peptide, T is bound radioactivity in the absence of the peptide, and NSP is bound radioactivity in the presence of excess nonlabeled ligand.

Figure 10:
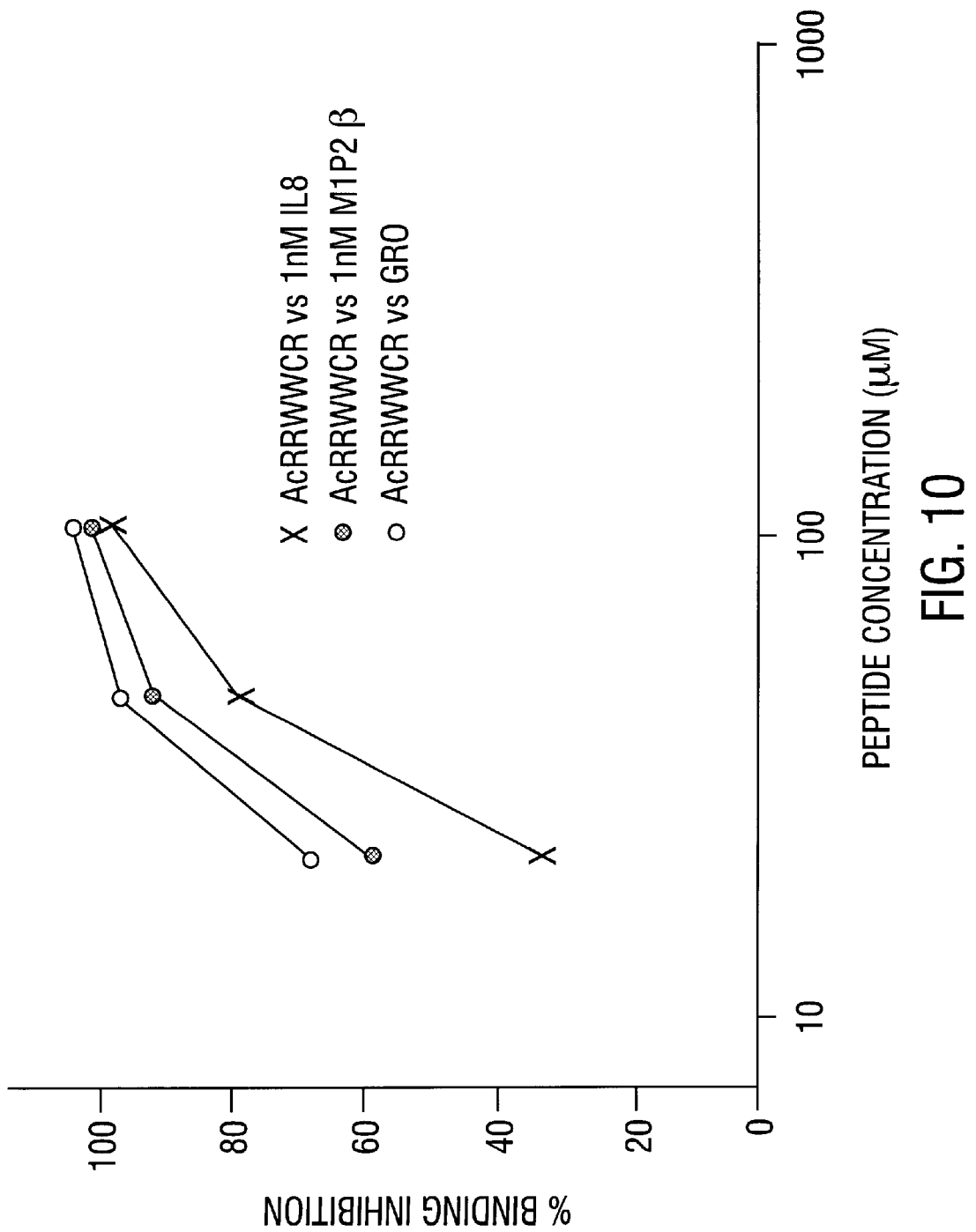
FIG. 10. Ac-RRWWCX (SEQ ID NO:23) Inhibits Binding of GRO and MIP2β to human neutrophils. Radioiodinated MIP2β and GRO/MGSA were mixed with various concentration of Ac-RRWWCR-NH$_2$ and incubated at room temperature for 15 min. Neutrophil suspension (1×10$^6$ cells in 160 μl PBS containing 0.1% BSA) was added to 40 μl of the mixture and incubated for 90 min on ice. The radioactivity bound to the cells was separated from free radioactivity by centrifugation through an oil layer. The % binding inhibition was calculated as follows.

In these studies, it was confirmed that Ac-RRWWCX-NH$_2$ (SEQ ID NO:23) inhibited binding of 1 nM IL-8 to neutrophils in a dose dependent manner, with an EC$_{50}$ of almost 25 μM (FIG. 10). Ac-RRWWCX-NH$_2$ (SEQ ID NO:23) was also found to effectively suppress the binding of 1 nM GRO and 1 nM MIP2β to neutrophils in a similar manner, as shown in FIG. 10.

EXAMPLE VIII

The following example illustrates the effect of a particular hexapeptide, RRWWCR, on binding of MGSA/GROα to melanoma cells.

In this study, the binding of α-chemokines to Hs 294T melanoma cell line was examined showing that MGSA/GROα but not IL-8 could bind to the cells. This finding is compatible with a previous study in which the presence of a receptor unique for MGSA/GROα on Hs 294T cells was indicated (Horuk et al., 1993). However, studies have shown that IL-8 receptor B is present in melanoma cells and plays a role in the cell growth (Mueller et al., 1994; Norgauer et al., 1996).

IL-8 receptor B messenger RNA and protein expression have been identified in various melanoma cell lines including Hs 294T. The antibody against IL-8 receptor B partially blocked specific binding of MGSA/GROα. Furthermore, addition of F(ab')$_2$ fragments of the anti-IL-8 receptor B or anti-MGSA/GROα monoclonal antibody inhibited serum-independent melanoma cell growth in vitro (Norgauer et al., 1996).

These results suggested that, at least a part of, binding of MGSA/GROα to the melanoma cells is mediated by IL-8 receptor B on the surface. As shown in Table 7, melanoma cell lines produced IL-8 at approximately 10 times higher concentration than MGSA/GROα. Therefore, the inability to see IL-8 binding to melanoma cells may result from two types of α-chemokine receptors on melanoma cells, IL-8 receptor B and a unique receptor for MGSA/GROα, while IL-8 receptor B is completely down-regulated by high concentration of IL-8. However, the presence of a putative receptor has yet to be confirmed. It is also possible that, although IL-8 receptor B rather than a unique MGSA/GROα receptor is expressed on melanoma cells, IL-8 in the culture renders IL-8 receptor B insensitive to IL-8 but not to MGSA/GROα via conformational changes in the receptor. The latter explanation is supported by a report that the interaction of IL-8 receptor B with its ligands is not homogeneous (Hayashi et al., 1995).

Methods

Peptide Synthesis

A hexapeptide, RRWWCR with acetylated N-terminus and amidated C-terminus (Antileukinate), was synthesized and purified by Houghten Pharmaceutical Inc. in San Diego as described in Example 1. In some studies, the Antileukinate was radioactively labeled by acetylating the amino terminus with tritiated anhydrous acetic acid. This procedure was carried out at Multiple Peptide Systems (San Diego, Calif.). The resulting specific radioactivity was 156 Ci/mole.

Cell Culture

Melanoma cell lines, Hs 294T and RPMI-7951, were purchased from American Type Culture Collection (Rockville, Md.). A liver cancer cell line, Hep G2, was obtained from M.-C Liu (University of Texas Health Center at Tyler). The cells were maintained in RPMI-1640 medium containing 10% fetal bovine serum (HyClone Laboratories Inc., Loan, Utah), 2 mM L-glutamine, 50 unit/ml of penicillin and 50 mg/ml of streptomycin.

Binding Assays

Recombinant human MGSA/GROα and IL-8 were purchased form Pepro Tech Inc. (Rocky Hill, N.J.) and radioactively labeled using $^{125}$I-labeled Bolton-Hunter reagent (DuPont-NEN, Wilmington, Del.) (Bolton and Hunter, 1973). The labeled proteins were isolated using Sephadex G-25 column (Column PD-10, Pharmacia) pre-equilibrated with PBS containing 0.1% gelatin and stored at −70° C. after the addition of 1% bovine serum albumin.

Binding studies with melanoma cell lines were performed by the method of Horuk and colleagues (Horuk et al., 1993). Briefly, the cells (1×10$^5$ cells/well) in 24-well plates were washed two times with Hank's Balanced Salt Solution and incubated with $^{125}$I-labeled MGSA/GROα or IL-8 in the buffer containing 1% bovine serum albumin at 4° C. for 3 hr. The incubation was terminated by vacuum aspiration of the supernatant. The cells were washed three times in binding buffer, solubilized by the addition of 200 μl of 1% SDS, and transferred to vials for counting. The non-specific binding was estimated by measuring the binding in the presence of 100-fold excess of non-labeled ligand. The binding parameters were calculated using the Lundon II computer program (Lundon Software Inc., Chagrin Falls, Ohio).

Measurement of MGSA/GROα and IL-8

HGSA/GROα in the culture supernatants was measured using an enzyme immunoassay (R and D Systems, Minneapolis, Minn.). IL-8 was measured with a sandwich enzyme immunoassay (Ko et al., 1992). Plates were coated with monoclonal anti-human IL-8 antibody grown and purified from hybridoma HB9647 which was obtained from Dr. E. J. Leonard (Immunopathology Section, Laboratory of Immunobiology, National Cancer Institute, Frederick, Md.). Samples were then added and IL-8 bound to the plates was detected with a two step incubation with rabbit polyclonal anti-human IL-8 antibody (Upstate Biotechnology, Lake Placid, N.Y.) and swine anti-rabbit immunoglobulins conjugated with horseradish peroxidase (DAKO Corp., Carpinteria, Calif.). Both immunoassays were specific for their antigen and did not cross-react with other members of the α-chemokine family.

Analysis of Antileukinate Breakdown

Hs 294T and Hep G2 cells, 2×10$^4$ cell/well, were cultured in 24 well tissue culture plates for 24 hr. Then the culture media were replaced with media containing tritiated Antileukinate, 0.2 μCi, mixed with 100 μM unlabeled peptide in each well. The cells were then cultured for the indicated periods. The supernatants were collected and stored at −70° C. until use. The breakdown of Antileukinate during the cell culture was analyzed on high performance liquid chromatography (HPLC) using an analytical C18 reversed phase column (Waters Co., New Bedford, Mass.). The peptides were eluted using a gradient from 0.1% trifluoroacetic acid (TFA) to 80% acetonitrile in 0.1% TFA. One milliliter fractions were collected and measured for their radioactivity content using a liquid scintillation counter.

Cell Growth Assays

The cell lines (2×10$^4$ cells/well) in 500 μl cell culture medium were grown in 24 well tissue culture plates. After the cells adhered to the plate, the supernatants were aspirated and 500 μl of media containing various concentrations of Antileukinate were added to the wells. The cells were cultured for period indicated in the text. The culture media were changed to fresh media every 24 hr. After incubation, the cells were detached with trypsin-EDTA solution (Life Technologies Inc., Gaithersburg, Md., containing 0.05% of trypsin and 0.53 mM of EDTA in Hanks Balanced Salt Solution without $Ca^{2+}$ and $Mg^{2+}$) and the cell number was counted using a hemocytometer.

Measurement of Cytotoxic Activity of the Peptide

The cell lines (4×10$^5$ cells/well) in RPMI-1640 medium containing 10% fetal bovine serum were incubated with 10 μCi of $Na_2^{51}CrO_4$ (DuPont NEN Co.) for 60 min at 37° C. in a 24 well tissue culture plate. The cells were washed 3 times and then incubated in cell culture medium for 30 min at 37° C. to allow spontaneous lysis of marginally viable cells. After washing twice, a 200 μl aliquot of the Antileukinate in cell culture medium was added to each well. The cells were cultured for 16 hr at 37° C. and then the radioactivity in the supernatants was counted in a gamma radiation spectrometer. Quadriplicate wells received cell culture medium alone or 2% SDS to determine spontaneous and maximum release, respectively. The percentage lysis was calculated by using the following formula:

$$\% \text{Lysis} = \frac{(\text{experimental cpm spontaneous cpm})}{(\text{maximum cpm} - \text{spontaneous cpm})} \times 100$$

Statistics

The data are expressed as the mean and standard deviation (S.D.) unless otherwise noted. Significance of differences between multiple groups was tested using the analysis of variance and Scheffe's Test.

Results

The effect of Antileukinate on autostimulatory growth of melanoma cell lines Hs 294T and RPMI-7951 was tested. Antileukinate significantly inhibited the binding of MGSA/GROα to these melanoma cell lines. Since Hs 294T and RPMI-7951 secreted MGSA/GROα into the supernatant, the effect of Antileukinate on the autostimulatory growth of the cells was examined. When the peptide was added to the culture of melanoma cells, it suppressed the cell growth almost completely at 100 $\mu$M. The peptide was more effective on Hs 294T cells than RPMI-7951 cells. The peptide did not affect the growth of the Hep G2 liver cancer cell line, which did not produce MGSA/GROα.

The melanoma cell growth inhibition by Antileukinate seemed to be associated with specific ability of the peptide to inhibit α-chemokine-receptor interaction rather than non-specific cell growth inhibition by itself or its metabolites. Antileukinate did not affect the growth of SP2/o mouse myeloma cell lines stimulated by murine interleukin-6. Antileukinate did not inhibit the growth of Hep G2 cells which metabolized the peptide in a similar way to Hs 294T cells. The cell viability of Hs 294T in the presence of 100 $\mu$M peptide was greater than 92% as assessed by trypan blue dye exclusion. The peptide did not cause cell lysis of either melanoma cell lines or Hep G2 cells. Furthermore, the removal of the peptide from Hs 294T cell culture or the addition of excess MGSA/GROα to the culture restored the cell growth. This suggested that MGSA/GROα is an essential autostimulatory growth factor for melanoma cells and Antileukinate inhibits their growth by preventing MGSA/GROα from binding to its receptors.

TABLE 7

IL-8 and MGSA/GROα in the Culture Supernatants

| origin of cell line | IL-8* (ng/ml) | MGSA/GROα* (ng/ml) |
|---|---|---|
| Hs 294T | melanoma | 178.3 ± 1.0 | 24.3 ± 0.8 |
| RPMI-7951 | melanoma | 138.2 ± 0.7 | 2.6 ± 0.1 |
| Hep G2 | liver | 2.0 ± 0.0 | <0.06 |

*The cells (5 × 10$^4$) were cultured in a 24 well plate for 48 hr. The supernatants were collected and the concentrations of chemokines were measured as described in the text.

TABLE 8

Cytotoxic Test of Antileukinate on Cultured Cell Lines

| Peptide Added | % cell lysis* | | |
|---|---|---|---|
| ($\mu$M) | Hs 294T | RPMI-7951 | Hep G2 |
| 0 | 0.0 ± 4.5 | 0.0 ± 2.7 | 0.0 ± 11.0 |
| 1 | −4.0 ± 5.2 | −0.8 ± 2.2 | −2.1 ± 7.5 |
| 5 | −3.2 ± 7.2 | −2.6 ± 3.7 | −0.8 ± 8.3 |
| 20 | −1.6 ± 3.7 | −3.4 ± 6.3 | 5.8 ± 8.3 |
| 100 | 2.4 ± 7.9 | 6.8 ± 11.1 | 0.9 ± 2.9 |

*The cells labeled with $^{51}$Cr were cultured in the presence of various concentrations of Antileukinate for 16 hr. Then the radioactivity in the supernatants was counted. The percentage cell lysis was calculated based on the amount of chromium released from the cells during the culture.

Effect of Antileukinate on Binding of MGSA/GROα to Melanoma Cells

Figures 1, 11B:
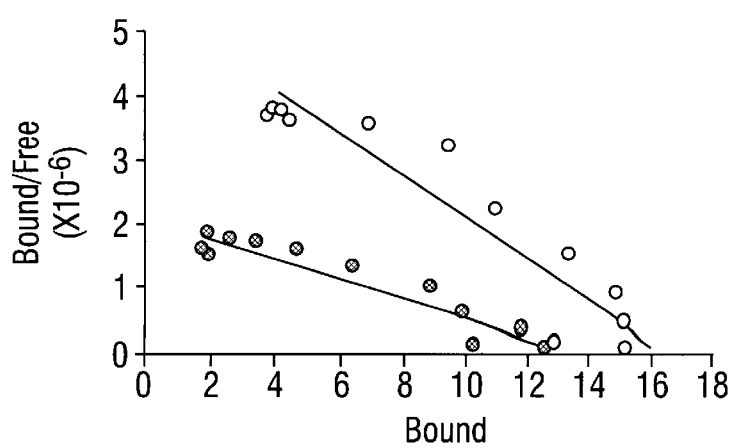

The binding of radiolabeled MGSA/GROα to melanoma cell lines was specific and saturable (FIG. 11). The Kd values calculated were approximately 6×10$^{-9}$M and 3×10$^{-9}$M for Hs 294T and RPMI-7951, respectively. The maximal binding ($B_{max}$) of MGSA/GROα to the melanoma cell lines was 11 fmole/10$^5$ cells and 15 fmole/10$^5$ cells respectively. Thus, the number of MGSA/GROα binding sites were estimated to be 70,000–100,000/a melanoma cell. There was, however, no specific binding of IL-8 to either cell line (FIG. 12).

Antileukinate inhibited the binding of MGSA/GROα to both of the melanoma cell lines. When the melanoma cell lines, Hs 294T and RPMI-7951, were incubated with $^{125}$I-labeled MGSA/GROα, 1 nM, in the presence of Antileukinate, the binding was inhibited by Antileukinate with an EC$_{50}$ of approximately (1 $\mu$M (FIG. 13).

The Production of α-chemokines form the Melanoma Cell Lines

The supernatants of melanoma cells cultured for 48 hr were tested for the presence of α-chemokines. The concentration of MGSA/GROα was 24.3±0.8 ng/ml in Hs 294T and 2.6±0.1 ng/ml in RPMI-7951 supernatants (Table 7). IL-8 was detected at much higher concentrations in the supernatants from both melanoma cell lines (Table 7). Liver cancer cell line, Hep G2, also produced detectable amounts of IL-8, however, the concentration was only a small fraction of that seen in the melanoma cell cultures. MGSA/GROα could not be detected in the supernatants of Hep G2 cells.

Effect of Antileukinate on Melanoma Cell Growth

Since Antileukinate inhibited the binding of MGSA/GROα to melanoma cell lines, the ability of Antileukinate to suppress auto-stimulatory growth of melanoma cells was tested. Prior to these studies, the time dependent breakdown of Antileukinate by Hs 294T melanoma cells and Hep-G2 liver cancer cells were examined. When the radiolabeled Antileukinate in RPMI-1640 medium was analyzed by HPLC, the major peak of the radioactivity was eluted at 50–51 ml (FIG. 14). After a 24 hr culture period, the major peak had decreased by more than 85% and there was a transient increase in the peek seen at 41–42 ml (FIG. 14). These findings showed that most Antileukinate in both cell cultures disappeared within 24 hr by a two step catabolic process. Therefore, in later studies the culture medium containing Antileukinate was exchanged every 24 hr to maintain the effect of Antileukinate.

Cell lines were cultured in the presence of various concentrations of Antileukinate for 72 hr and the number of cells in the well were counted. The growth of Hs 294T cells was significantly inhibited by 10 $\mu$M peptide (FIG. 15A) with an ED$_{50}$ of 18 $\mu$M. Antileukinate also suppressed the growth of RPMI-7951 melanoma cells with an ED$_{50}$ of 31 $\mu$M (FIG. 15B); however, it did not affect the growth of Hep G2 liver cancer cells (FIG. 15C).

The inhibition of Hs 294T growth was further characterized. It was reversed by the removal of Antileukinate from the culture media (FIG. 16A) and by the addition of 50 nM MGSA/GROα to the receptors on the Hs 294T cell surface.

Cytotoxicity of Antileukinate

To exclude the possible contribution of cytotoxicity of Antileukinate to the inhibition of melanoma cell growth, $^{51}$Cr-labeled cells were cultured in the presence of the peptide for 16 hr. Antileukinate did not cause cell lysis of either of the melanoma cell lines or Hep G2 cell line (Table 8). Measurements of cell viability by Trypan Blue exclusion also indicated that Antileukinate was not toxic to the cells (FIG. 17). The adhesivity of Hs 294T, RPMI-7951 and Hep G2 cells to the culture wells did not alter when Antileukinate was added.

Effect of Antileukinate on other Tumor Cells

Antileukinate was shown to inhibit the growth of a wide range of tumor cells in addition to melanoma cells. FIG. 18 illustrates a decrease in cell number of adenocarcinoma of prostate cells. The effect is dose dependent. Similar effects are observed at even lower concentrations of Antileukinate on squamous cell carcinoma cells (NCI-H292) from lung (see FIG. 19). FIG. 20 shows the effect of antileukinate on growth of A549 cells (from adenocarcinoma of the lung).

EXAMPLE IX

Therapeutic Formulations and Treatment Protocols

This example is directed to the techniques contemplated by the inventors for use in further characterizing the in vivo actions of the IL-8 inhibitors and their use in animal or human treatment protocols.

A. Effects of IL-8 Inhibitors on Inflammation In Vivo

Prior to animal model studies, in vitro stability examinations may be performed on the peptides including, for example, pre-incubation in human serum and plasma; treatment with various proteases; and also temperature- and pH-stability analyses. It is already known that D-amino acid peptides are active and that these would likely have enhanced stability in vivo.

The inventors propose to examine the in vivo properties and effects of the IL-8 peptide inhibitors in animal models prior to moving onto clinical trials. The most suitable form, dose and any possible toxicity of the peptides will be determined in animal studies, as is routinely employed in the art. For example, the bio-availability and half lives of the peptides administered in various ways may be determined using radioactively labeled peptides and examining their longevity and tissue distribution. If further stability enhancement was desired, the peptides could also be administered in the form of lipid-tailed peptides, surfactant-like micelles, peptide multimers or in semi-permeable drug release capsules.

The biological effects of the peptides may be determined in various models of human disease. For example, IL-8 has been shown to cause the accumulation of neutrophils and edema in rabbit skin (Rampart et al., 1989). Therefore, a rabbit dermal inflammation model will be employed to determine what dose of the peptides can effectively inhibit the neutrophil accumulation and edema. This model is useful because of the ease of assessment of inflammation. The most suitable route of peptide administration may be easily determined by comparative in vivo tests.

In one particular example, New Zealand albino rabbits may be injected with $^{125}$I-labeled human serum albumin through the lateral ear vein. Certain sites may then be injected intradermally with the test compounds, i.e., an agonist to attract neutrophils and an IL-8 inhibitor peptide; the agonist and a control peptide; and the agonist alone. About two hr later, full thickness skin samples 1 cm in diameter may be punched out, fixed and stained with Wright-Giemsa or for myeloperoxidase and the histology examined for neutrophil accumulation and edema or tissue damage. Other skin biopsies may be counted in a gamma counter to assess the amount of albumin flux into the injected skin. Skin inflammation after administration of the inhibitor can then be compared to the time-matched controls, ideally be performed in the same animal. At least 4 replicates for each experimental arm are recommended.

B. IL-8 Inhibitor Treatment of ARDS

The best human model of Adult Respiratory Distress Syndrome (ARDS) is probably the introduction of gram negative bacteria into the circulation of minipigs. This model will be employed to determine if IL-8 is the major neutrophil activator in this model of ARDS, as it is in human ARDS, using studies similar to those carried out in man. The effects of IL-8 administration through intravenous and intrapulmonary routes in minipigs will be assessed.

In the first step, the minipigs will be treated with IL-8 through the most appropriate route to cause neutrophil influx and enzyme release into the lungs as assessed above. The peptides of interest will be administered to determine appropriate doses for use in impeding these neutrophil functions, especially the dose with which the peptide suppresses enzyme release, but not the neutrophil influx.

In the next step, the acute lung damage model of minipigs caused by gram negative bacteria in the circulation will be employed. The peptides of interest will be administered to the animals and the effect of the peptides on the prevention of lung damage will be assessed. The number of neutrophils in bronchoalveolar fluids, the amount of enzyme released into lung parenchyma, and the degree of protein leakage from circulation to lung will be used as indicators in this study.

If IL-8 causes neutrophil influx, enzyme release into the lungs, and/or ARDS-like tissue damage to the lungs, as expected, the peptides of interest will be administered to determine the appropriate doses for use in impeding these neutrophil functions. In these studies, various intravenous doses of radioactively labeled peptides will be administered initially. Plasma concentrations and forms of the radioactivity will then be determined. From these data, plasma clearance, half life and steady state volume of distribution will be measured and used to determine the most effective dose ranges.

C. Treatment Protocols

Due to precautions which are necessarily attendant to every new pharmaceutical, the IL-8 peptide inhibitors and compositions of the present invention have not yet been tested in a clinical setting in human subjects. However, their clear in vitro activity in accepted models is believed to demonstrate the utility of the present invention as an anti-inflammatory agent. Clinical trials will be conducted in due course and, naturally, will be in accordance with the FDA procedures. The following embodiments represent the best modes currently contemplated by the present inventors for carrying out the practice of the invention in various clinical settings.

It is believed that pharmaceutical compositions which include peptide inhibitors of IL-8 will prove to be useful in the treatment of various conditions, including pulmonary disorders such as bronchial inflammation, cystic fibrosis, pleural effusions, asthma, bronchitis and ARDS; skin disorders such as psoriasis and dermatitis; diseases of the joints, including rheumatoid arthritis; and in the treatment of pseudogout, inflammatory bowel disease, reperfusion cardiac damage or even in the treatment of cancer and other diseases and disorders associated with increased cellular proliferation.

As these peptides are thought to be particularly suitable for the inhibition of pulmonary inflammation, such as occurs in ARDS, chronic bronchitis and cystic fibrosis, suitable treatment methods for these disorders will be described. For the treatment of ARDS or cystic fibrosis, one would preferably employ parenteral administration, such as by using intravenous, intramuscular or subcutaneous injections. However, one may also use aerosols or inhalants. The preparation of peptide formulations for parenteral administration, particularly those formulated as injectables, is described in detail in the Preferred Embodiments section of the present application. The following describes certain inhalant formulations, should one desire to use such methods in connection with the present invention.

Inhalations and inhalants are pharmaceutical preparations designed for delivering a drug or compound into the respiratory tree of a patient. A vapor or mist is administered and reaches the affected area to give relief from symptoms of bronchial and nasal congestion. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered dose of the inhalation is propelled into the respiratory tract of the patient.

Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

The intravenous administration of one, or a combination, of the anti-IL-8 peptides described in this application is contemplated to be capable of attenuating inflammation in ARDS and cystic fibrosis. The range of doses to be administered is estimated to be in the range of about 500 to about 1000 mg/day, or between about 0.83 mg/kg body weight/hour (mg/kg/hr) to about 16.56 mg/kg/hr.

Of course, one must not lose sight of the fact that various other pharmaceutical formulations of the IL-8 inhibitors may be prepared and used to treat many other disorders connected with neutrophil activation and inflammation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are incorporated in pertinent part by reference herein for the reasons cited above.

Arshady, Atherton, Gait, Lee, Sheppard, *J. Chem. Soc. Chem. Commun.*, 23:423–425, 1979.

Baggiolini, Imboden, Detmers, *In: Cytokines: Interleukin 8 (NAP-1) and Related Chemotactic Cytokines* (Gabbiolini, M. and Sorg, C., eds) Karger, Basel, pp. 1–17, 1992.

Baldwin, Weber, St. Charles, Xuan, Apella, Yamada, Matsushima, Edwards, Clore, Groenenbom, Wlodawer, *Proc. Natl. Acad. Sci. USA*, 88:502–506, 1991.

Balk and Bone, *Med. Clin. North Am.*, 67:685–700, 1983.

Bedard, McClure, Schiller, Francoeur, *Am. J. Respir. Cell. Mol. Biol.*, 9:455–462, 1993.

Besemer, Hujber, Kuhn, *J. Biol. Chem.*, 264:17409–17415, 1989.

Bolton and Hunter, "The labeling of proteins to high specific radioactivities by conjugation to a $^{121}$I-containing acylating agent: Application to the radioimmunoassay," *Biochem. J.*, 133:529–539, 1973.

Braunwalder, Musmanno, Galakatos, Garlick, Haston, Rediske, Wennogle, Siligmann, Sills, *Molec. Immun.*, 29:1319–1324, 1992.

Brennan, Zachariae, Chantry, Turner, Maini, Matsushima, Feldman, *Eur. J. Immunol.*, 20:2141–2144, 1990.

Cassatella, Aste, Calzetti, Constantin, Guasparri, Ceska, Rossi, *Biochem. Biophys. Res. Commun.*, 190:660–667, 1993a.

Cassatella, Guasparri, Ceska, Bazzoni, Rossi, *Immunol.*, 78:177–184, 1993b.

Cerretti, Kozlosky, Vanden Bos, Nelson, Gearing, Beckman, *Molec. Immun.*, 30:359–367, 1993.

Clark-Lewis, Schumacher, Baggiolini, Moser, *J. Biol. Chem.*, 266:23128–23134, 1991.

Clore and Gronenbom, *In: Cytokines: Interleukin 8 (NAP-1) and Related Chemotactic Cytokines,* (Baggiolini, M. and Sorg, C., eds) Karger, Basel, pp. 18–40, 1992.

Clore, Apella, Yamada, Matsushima, Gronenborn, *Biochem.*, 29:1689–1696, 1990.

Cohen, Miller, Nagao, Carr, U.S. Pat. No. 5,079,228, 1992.

Corbi, Garcia-Aguilar, Springer, *J. Biol. Chem.*, 265:2782–2788, 1990.

DeForge, Fantone, Kenney, Remick, *J. Clin. Invest.*, 90:2123–2129, 1992.

Dohlman, Caron, Lefkowitz, *Biochem.*, 26:2657–2664, 1987.

Gayle, Sleath, Srinivason, Birks, Weerawarna, Cerretti, Kozlosky, Nelson, Vanden Bos, Beckmann, *J. Biol. Chem.*, 268:7283–7289, 1993.

Goldstein, Hoffstein, Gallin, Weissman, *Proc. Natl. Acad. Sci. USA*, 70:2916–2920, 1973.

Goodman, Forstrom, Martin, *FASEB J.*, 5(4):A892, Abstract #3032, 1991.

Hayashi, Kurdowska, Miller, Albright, Girten, Cohen, "Synthetic hexa- and heptapeptides which inhibit IL-8 from binding to and activating human blood neutrophils," *J. Immunol.*, 154:814–824, YEAR.

Hayashi, Stevens, Miller, Kurdowska, Strieter, Walz, Cohen, "Characterization of the binding of epithelial neutrophil activating peptide-78 (ENA78) to interleukin-8 receptors," *FASEB J.*, 9:A247, 1995.

Herbert, Luscinskas, Kiely, Luis, Darbonne, Bennett, Liu, Obin, Gimbrone, Baker, *J. Immunol.*, 145:3033–3040, 1990.

Holmes, Lee, Kuang, Rice, Wood, "Structure and functional expression of a human interleukin-8 receptor," *Sci.*, 253:1278–1280, 1991.

Holmes, Lee, Kuang, Rice, Wood, *Sci.*, 253:1278, 1991.

Horuk, Yansura, Reilly, Spencer, Bourell, Henzel, Rice, Unemori, "Purification, receptor binding analysis, and biological characterization of human melanoma growth stimulating activity (MGSA)," *J. Biol. Chem.*, 268:541–546, 1993.

Houghten, Pinilla, Blondelle, Appel, Dooley, Cuervo, *Nature*, 354:84–86, 1991.

Hunter and Greenwood, *Nature*, 194:495–496, 1962.

Idell, Kucick, Fein, Kueppers, James, Walsh, Weinbaum, Colman, Cohen, *Am. Rev. Respir. Dis.*, 132:1098–1105, 1985.

Ko, Mukaida, Panyutich, Voitenok, Matsushima, Kawai, Kasahara, "A sensitive enzyme-linked immunosorbent assay for human interleukin-8," *J. Immunol. Meth.*, 149:227–235, 1992.

Koch, Polverini, Kunkel, Harlow, DiPietro, Elner, Elner, Strieter, *Sci.,* 258:1798–1801, 1992.

Kohler and Milstein, *Nature,* 256:495–497, 1975.

Kyte and Doolittle, *J. Mol. Biol.,* 157:105–132, 1982.

Lam, Klein, Lindley, In: *Chemotactic Cytokines. Biology of the inflammatory Peptide Supergene Family* (Westwick, J., Lindley, I.J.D., and Kinkel, S.L., eds) Plenum Press Inc., New York, pp. 175–176, 1990.

LaRosa, Thomas, Kaufmann, Mark, White, Taylor, Gray, Witt, Navarro, *J. Biol. Chem.,* 267:25402–25406, 1992.

Larsen, Anderson, Apella, Oppenheim, Matsushima, *Sci.,* 243:1464–1466, 1989.

Lawson, Thomas, Roy, Gordon, Chawla, Nixon, Richmond, "Preparation of a monoclonal antibody to a melanoma growth-stimulatory activity released into serum-free culture medium by Hs0294 malignant melanoma cells," *J. Cell. Biochem.,* 34:169–185, 1987.

Lee, Horuk, Rice, Bennett, Camerato, Wood, *J. Biol. Chem.,* 267:16283–16287, 1982.

McElvaney, Nakamura, Birrer, Hebert, Wong, Alphonso, Baker, Catalano, Crystal, *J. Clin. Invest.,* 90:1296–1301, 1992.

McGuire, Spragg, Cohen, Cochrane, *J. Clin., Invest.,* 69:543–553, 1982.

Meienhofer, Waki, Heimer, Lambros, Makofske, Chang, *Int. J. Peptide Protein Res.,* 13:35–42, 1979.

Miller and Brelsford, *J. Rheumatol.,* 20:1250–1252, 1993.

Miller and Idell, *Exp. Lung Res.,* 19:589–601, 1993.

Miller, Cohen, Nagao, Griffith, Maunder, Martin, Wiener-Kronish, Sticherling, Christophers, Matthay, *Am. Rev. Respir. Dis.,* 146:427–432, 1992.

Miller, Kurdowska, Nagao, Carr, Hayashi, Atkinson, Cohen, *Agents and Actions,* 1993.

Miller, Nagao, Cohen, *FASEB J.,* 4(5):A2117, Abstract #2452, 1990.

Mintz and Silvers, "Transgenic mouse model of malignant skin melanoma," *Proc. Natl. Acad Sci.* USA, 90:8817–8821, 1993.

Moser, Barella, Mattei, Schumacher, Boulay, Colombo, Baggiolini, "Expression of transcripts for two interleukin 8 receptors in human phagocytes, lymphocytes and melanoma cells," *Biochem. J.,* 294:285–292, 1993.

Moser, DeWald, Barella, Schumacher, Baggiolini, Clark-Lewis, *J. Biol. Chem.,* 268:7125–7128, 1993.

Mueller, Schraw, Richmond, "Melanoma growth stimulatory activity enhances the phosphorylation of the class II interleukin-8 receptor in non-hematopoietic cells," *J. Biol. Chem.,* 269:1973–1980, 1994.

Mulligan, Jones, Bolanowski, Baganoff, Deppeler, Meyers, Ryan, Ward, *J. Immunol.,* 150:5585–5595, 1993.

Murphy and Tiffany, "Cloning of complementary DNA encoding a functional human interleukin-8 receptor," *Sci.,* 253:1280–1283, 1991.

Murphy and Tiffany, *Sci.,* 253:1280–1283, 1991.

Nakamura, Yoshimura, McElvaney, Crystal, *J. Clin. Invest.,* 89:1478–1484, 1992.

Nanney, Mueller, Bueno, Peiper, Richmond, "Distributions of melanoma growth stimulatory activity of growth-regulated gene and the interleukin-8 receptor B in human wound repair," *Am. J. Pathol.,* 147;1248–1260, 1995.

Norgauer, Metzner, Schraufstatter, "Expression and growth-promoting function of the IL-8 receptor beta in human melanoma cells," *J. Immunol.,* 156:1132–1137, 1996.

Oppenheim, Zachariae, Mikaida, Matsushima, *Annu. Rev. Immunol.,* 9:617–648, 1991.

Oppenheim, Zachariae, Mukaida, Matsushima, "Properties of the novel proinflammatory supregene 'intercrine' cytokine family," *Annu. Rev. Immunol.,* 9:617–648, 1991.

Ovchinnikov, Gubanov, Khramtsov, Ischenko, Zagranichny, Nuradov. Shuvaeva, Lipkin, *FEBS Lett.,* 223:169–173, 1987.

Peveri, Walz, DeWald, Baggiolini, *J. Exp. Med.,* 167:1547–1559, 1988.

Rampart, Van Damme, Zonnekeyn, Herman, *Am. J. Pathol.,* 135:21–25, 1989.

Richman-Eisenstat, Jorens, Hebert, Ueki, Nadel, *Am. J. Physiol.* (*Lung Cell Mol. Physiol*), 264:L413-L418, 1993.

Richmond and Thomas, "Purification of melanoma growth stimulatory activity," *J. Cell. Physiol.,* 129:375–384, 1986.

Richmond, Balentien, Thomas, Flaggs, Barton, Spiess, Borkoni, Francke, Derynck, "Molecular characterization and chromosomal mapping of melanoma growth stimulatory activity, a growth factor structurally related to beta-thromboglobulin," *EMBO J.,* 7:2025–2033, 1988.

Richmond, Fine, Murray, Lawson, Priest, "Growth factor and cytogenetic abnormalities in cultured nevi and malignant melanomas," *J. Invest. Dermatol.,* 86:295–302, 1986.

Richmond, Lawson, Nixon, "Release of an autostimulatory growth activity by human malignant melanoma cells," Cold Spring Harbor Conference: Cell Proliferation, 9:855–897, 1982.

Richmond, Lawson, Nixon, Chawla, "Characterization of auto stimulatory and transforming growth factors from human melanoma cells," *Cancer Research,* 1985.

Richmond, Lawson, Nixon, Stevens, Chawla, "Extraction of a melanoma growth-stimulatory activity from culture medium conditioned by the Hs0294 human melanoma cell lines," *Cancer Research,* 43:2106–2112, 1983.

Sambrook et al., Molecular cloning: A laboratory manual, Cold Spring Harbor Laboratory, Cold Spring Harbor, N.Y., 1989.

Schadendorf, Moller, Algermissen, Worm, Sticherling, Czarnetzki, "IL-8 produced by human malignant melanoma cell in vitro is an essential autocrine growth factor," *J. Immunol.,* 151:2667–2675, 1993.

Schmid and Weissmann, *J. Immunol.,* 139:250–256, 1987.

Schroder, Mrowietz, Christophers, *J. Immunol.,* 140:3534–3540, 1988.

Schumacher, Clark-Lewis, Baggiolini, Moser, *Proc. Natl. Acad. Sci.,* 89:10542–10546, 1992.

Seitz, DeWald, Gerber, Baggiolini, *J. Clin. Invest.,* 87:463–469, 1991.

Sherman, Goetzl, Koo, *J. Biol. Chem.,* 140:3900–3904, 1988.

Singh, Gutman, Radinsky, Bucana, Fidler, "Expression of interleukin 8 correlates with metastatic potential of human melanoma cells in nude mice," *Cancer Research,* 54:3242–3247, 1994.

Standiford, Kunkel, Mark, Evanoff, Allen, Strieter, *Am. J Respir. Cell Mol. Biol.,* 6:75–81, 1992.

Standiford, Strieter, Kashahara, Kunkel, *Biochem. Biophys. Res. Commun.,* 171:531–536, 1990.

Stewart and Young, In: *Solid Phase Peptide Synthesis,* W.H. Freeman and Co., San Francisco, pp. 1–26, 1969.

Strieter, Chensue, Basha, Standiford, Lynch, Baggiolini, Kunke, *Am. J Respir. Cell Mol. Biol.,* 2:321–326, 1990.

Strieter, Phan, Showell, Remick, Lynch, Genord, Raiford, Eskandari, Marks, Kunkel, *J. Biol. Chem.,* 264:10621–10626, 1989.

Togo, Burch, DeHaas, Connor, Steranka, *Peptides,* 10:109–112, 1989.

Van Zee, DeFirge, Fischer, Marano, Kenney, Remick, Lowry, Moldawer, *J. Immunol.,* 146:3478, 1991.

Venner, Sauder, Feliciani, Mckenzie, "Interleukin-8 and melanoma growth-stimulating activity are induced by ultraviolet B radiation in human keratinocyte cell lines," *Exp. Dermatol.,* 4:138–145, 1995.

Weiland, Davis, Holter, Mohammed, Dorinsky, Gadek, *Amer. Rev. Respir. Dis.,* 133:218–225, 1986.

Wu, LaRosa, Simon, *Sci.,* 261:101–103, 1993.

Yoshimura, Matsushima, Tanaka, Robinson, Appella, Oppengeim, Leonard, *Proc. Natl. Acad Sci.* USA, 84:9233–9237, 1987.

Yoshimura, Robinson, Apella, Matsushima, Showalter, Skeel, Leonard, *Molec. Immun.,* 26:87–93, 1989.

Zigmond and Hirsch, *J. Exp. Med.,* 137:387–410, 1973.

What is claimed is:

1. A method of inhibiting binding of an α-chemokine to a tumor cell, comprising administering to said cell an amount of a peptide comprising the sequence of SEQ ID NO:1 effective to inhibit binding of said α-chemokine.

2. The method of claim 1 wherein the tumor cell is identified as a melanoma cell line.

3. The method of claim 2 wherein the melanoma cell line is further identified as Hs 294T, RPMI-7951, A375P, A375SM, C8161 or WM115.

4. The method of claim 1 wherein the tumor cell is identified as an adenocarcinoma cell.

5. The method of claim 4 wherein the adenocarcinoma cell is further identified as lung adenocarcinoma cell A549, NCI-H441 or SK-LU-1.

6. The method of claim 1 wherein the tumor cell is a squamous lung cancer cell.

7. The method of claim 6 wherein the squamous cell lung cancer cell is further identified as NCI-H292.

8. The method of claim 4 wherein the adenocarcinoma cell is selected from the group consisting of stomach AGS, stomach Hs746T, breast cell MCG-7, prostate DU145 and colon Caco-2.

9. A method of inhibiting growth of a melanoma cell, comprising inhibiting binding of MGSA/Groα to said cell with an effective amount of a peptide having the amino acid sequence of Arg Arg Trp Trp Cys Arg (SEQ ID NO:1).

10. The method of claim 9 wherein the growth inhibiting is in vitro.

11. The method of claim 10 wherein the in vitro growth inhibiting effective amount is defined as between about 40 to about 125 μM the peptide having the amino acid sequence of SEQ ID NO:1.

12. The method of claim 11 wherein the effective amount is further defined as between about 50 μM and about 100 μM of the peptide having the amino acid sequence of SEQ ID NO:1.

13. The method of claim 1 wherein the tumor cell is identified as an endothelial cell.

14. The method of claim 13 wherein the endothelial cell is identified as a human umbilical vein endothelial cell.

* * * * *

UNITED STATES PATENT AND TRADEMARK OFFICE
CERTIFICATE OF CORRECTION

PATENT NO.    : 6,110,889
DATED         : August 29, 2000
INVENTOR(S)   : Miller, et al.

It is certified that error appears in the above-identified patent and that said Letters Patent is hereby corrected as shown below:

In Column 2, line 34, delete "bum" and replace --burn--therefor.

Signed and Sealed this

Fifteenth Day of May, 2001

Attest:

NICHOLAS P. GODICI

Attesting Officer

Acting Director of the United States Patent and Trademark Office